United States Patent [19]

Hudon et al.

[11] Patent Number: 5,460,178
[45] Date of Patent: Oct. 24, 1995

[54] ULTRASONIC TRANSMISSION IMAGING APPARATUS AND METHOD

[75] Inventors: Roméo Hudon, Longueuil; Alain Ross, Boisbriand; Pierre Isabelle, St-Hubert; Réal Archambault, Terrebonne; Pierre Gauthier, Boisbriand, all of Canada

[73] Assignee: Centre de Recherche Industrielle du Québec, Quebec, Canada

[21] Appl. No.: 381,651

[22] Filed: Jan. 31, 1995

[51] Int. Cl.⁶ .................................................. A61B 8/00
[52] U.S. Cl. .................................. 128/660.07; 73/607
[58] Field of Search ........................ 128/660.01, 660.06, 128/660.07, 660.08, 661.01, 661.02, 663.01; 73/602, 606, 607, 626, 620

[56] References Cited

U.S. PATENT DOCUMENTS

| | | |
|---|---|---|
| 3,805,596 | 4/1974 | Klahr . |
| 3,937,066 | 2/1976 | Green et al. . |
| 4,179,936 | 12/1979 | Bennett et al. . |
| 4,553,437 | 11/1985 | Luthra et al. . |
| 4,730,495 | 4/1988 | Green . |
| 4,744,131 | 5/1988 | Hartmann et al. . |
| 5,299,576 | 4/1994 | Shiba ................ 128/660.07 |
| 5,345,939 | 9/1994 | Engeler et al. ........... 128/661.01 |
| 5,349,262 | 9/1994 | Grenon et al. ........... 128/663.01 |

Primary Examiner—George Manuel
Attorney, Agent, or Firm—Swabey Ogilvy Renault

[57] ABSTRACT

A new ultrasonic transmission imaging apparatus is disclosed, which uses a new imaging method providing image focusing capability. The apparatus comprises an ultrasonic emitter producing substantially continuous coherent ultrasonic waves toward an object to be inspected. The apparatus further comprises an ultrasonic detectors array comprising a plurality of ultrasonic detectors receiving the object traversing ultrasonic waves to produce a plurality of series of electrical signals coming from the ultrasonic detectors, the electrical signals characterizing transmission of the ultrasonic waves through the object and being associated with series of image elements. The apparatus further comprises a signal vector components detector detecting signal vector components for each of the electrical signals. The apparatus further comprises a computer for controlling the apparatus and for receiving pairs of first and second signal vector component digital signals coming from the signal vector components detector. The computer has a memory for storing the pairs of first and second signal vector component digital signals and for storing focusing function data, which is used by the computer to produce corresponding pairs of first and second resulting signal vector component digital signals forming a focused digital image representation of the object traversing ultrasonic waves.

70 Claims, 18 Drawing Sheets

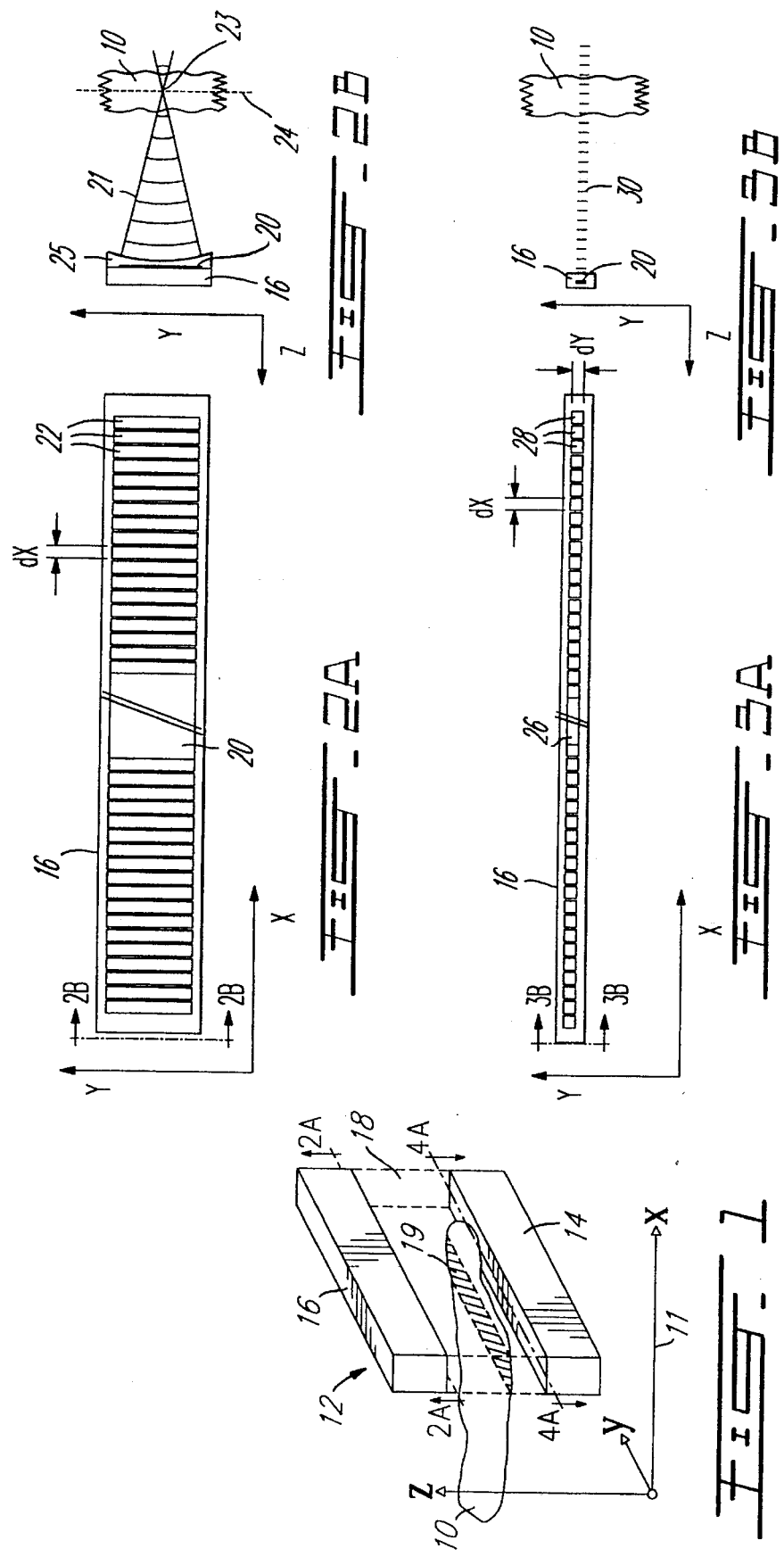

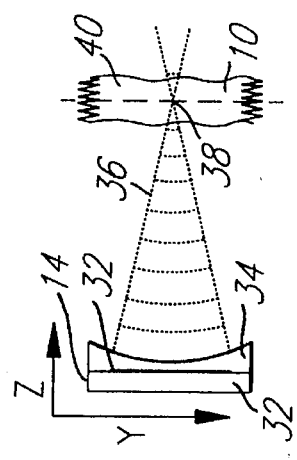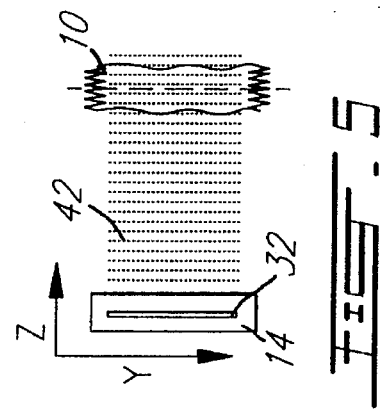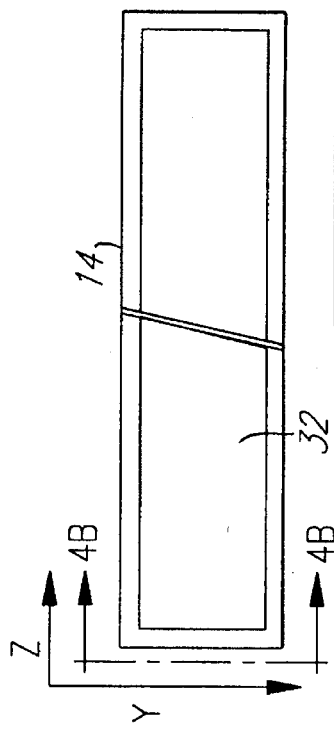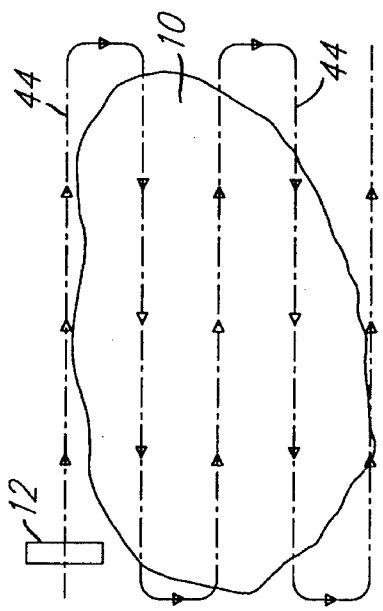

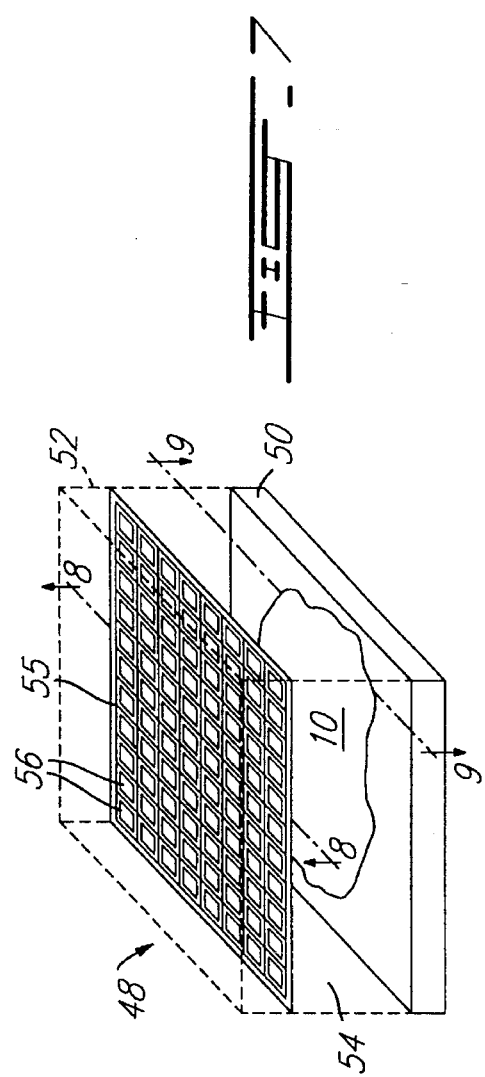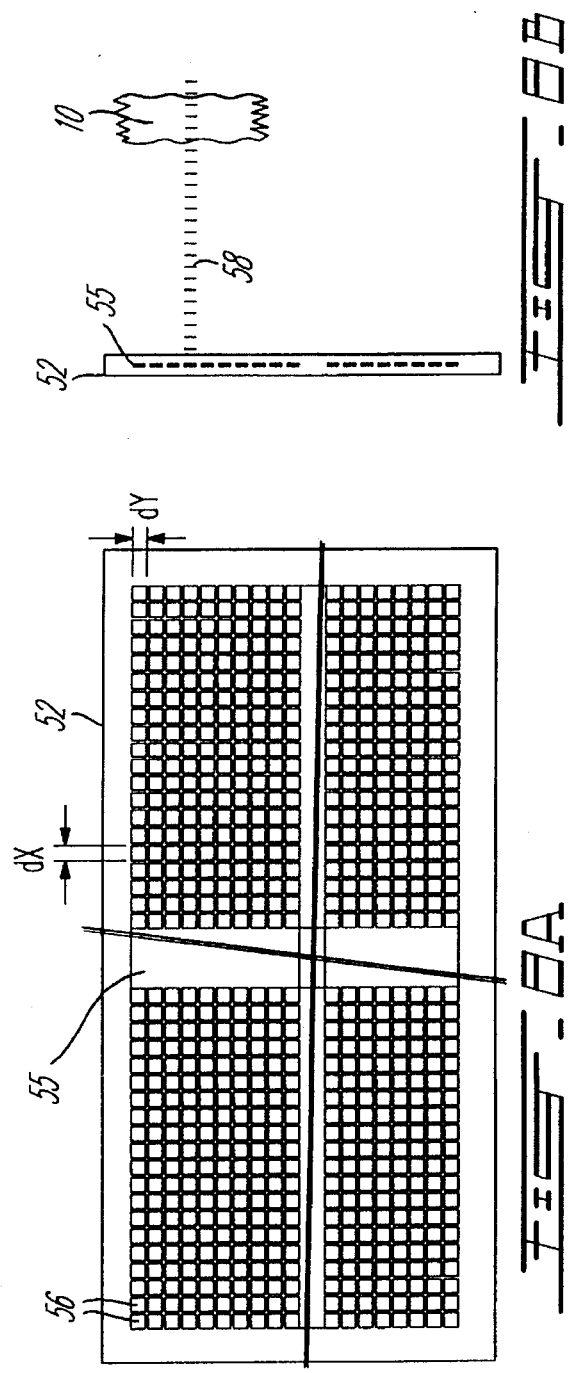

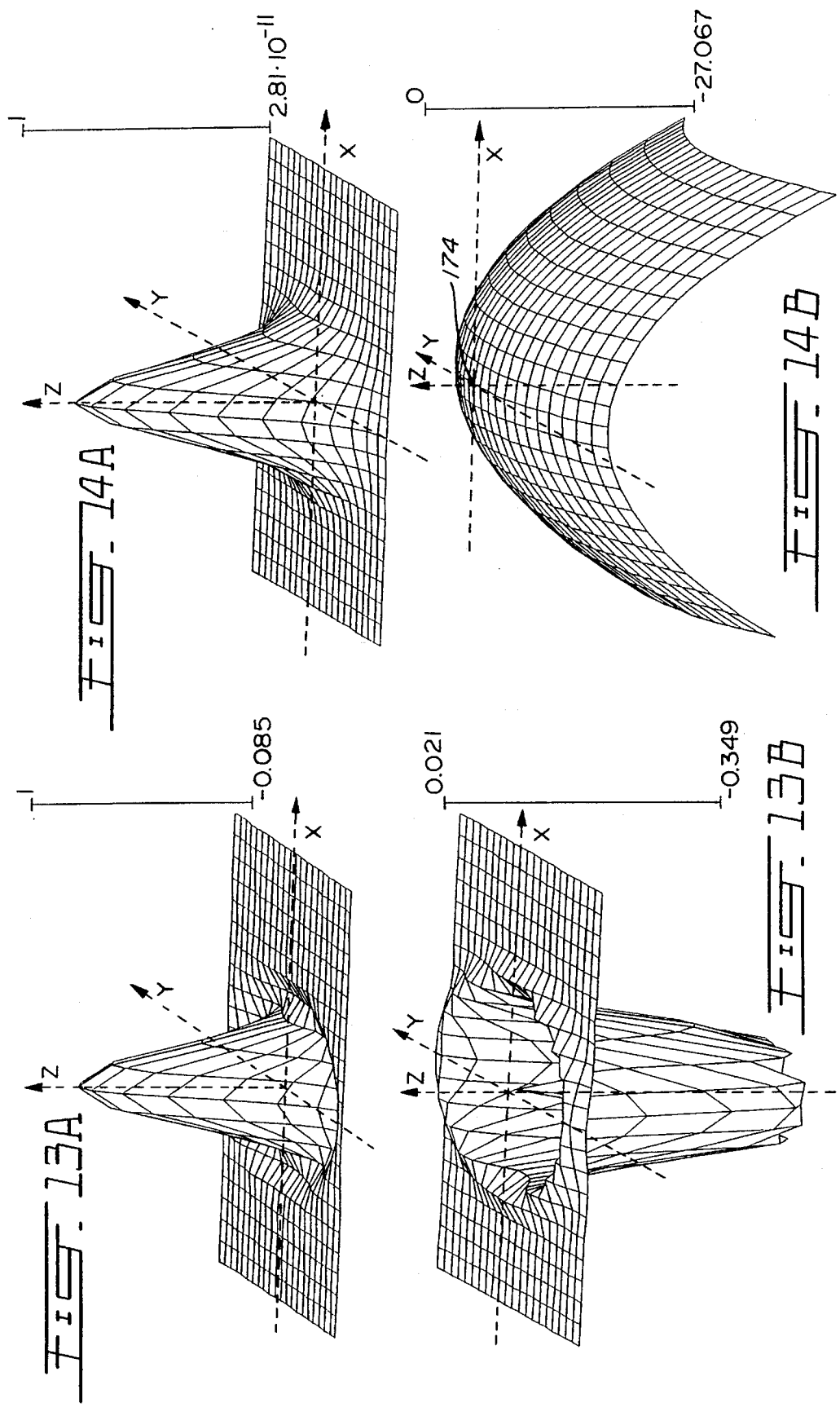

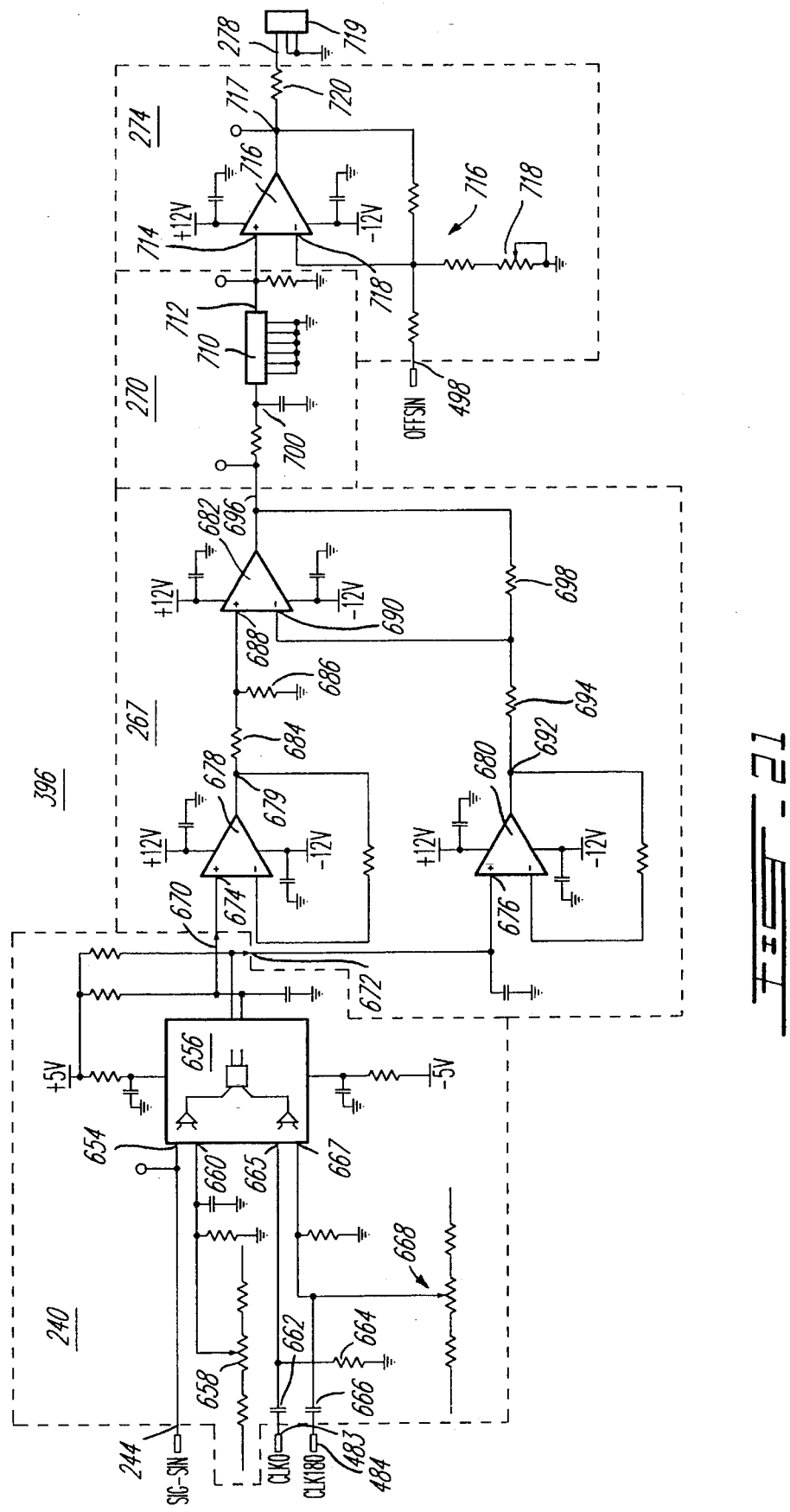

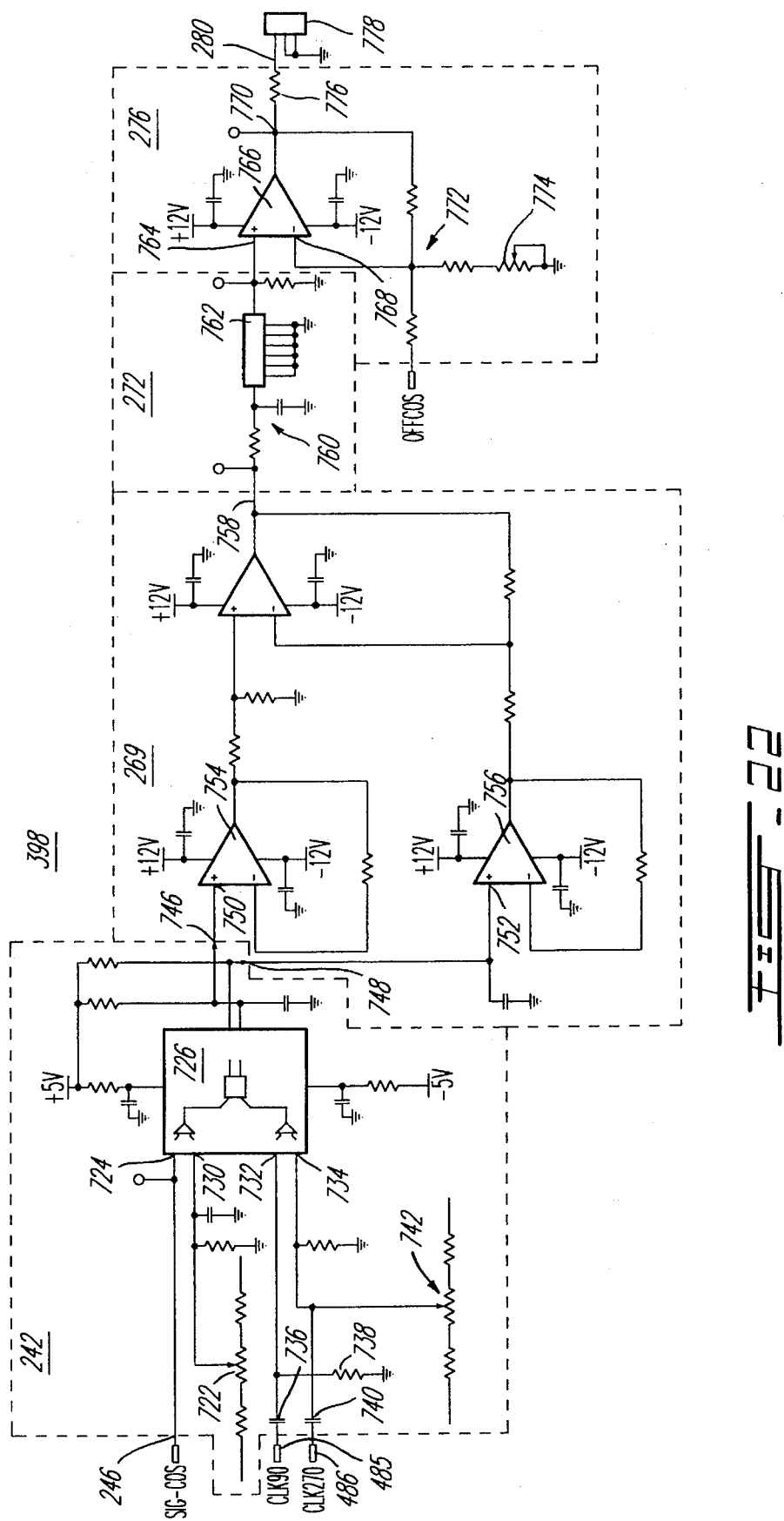

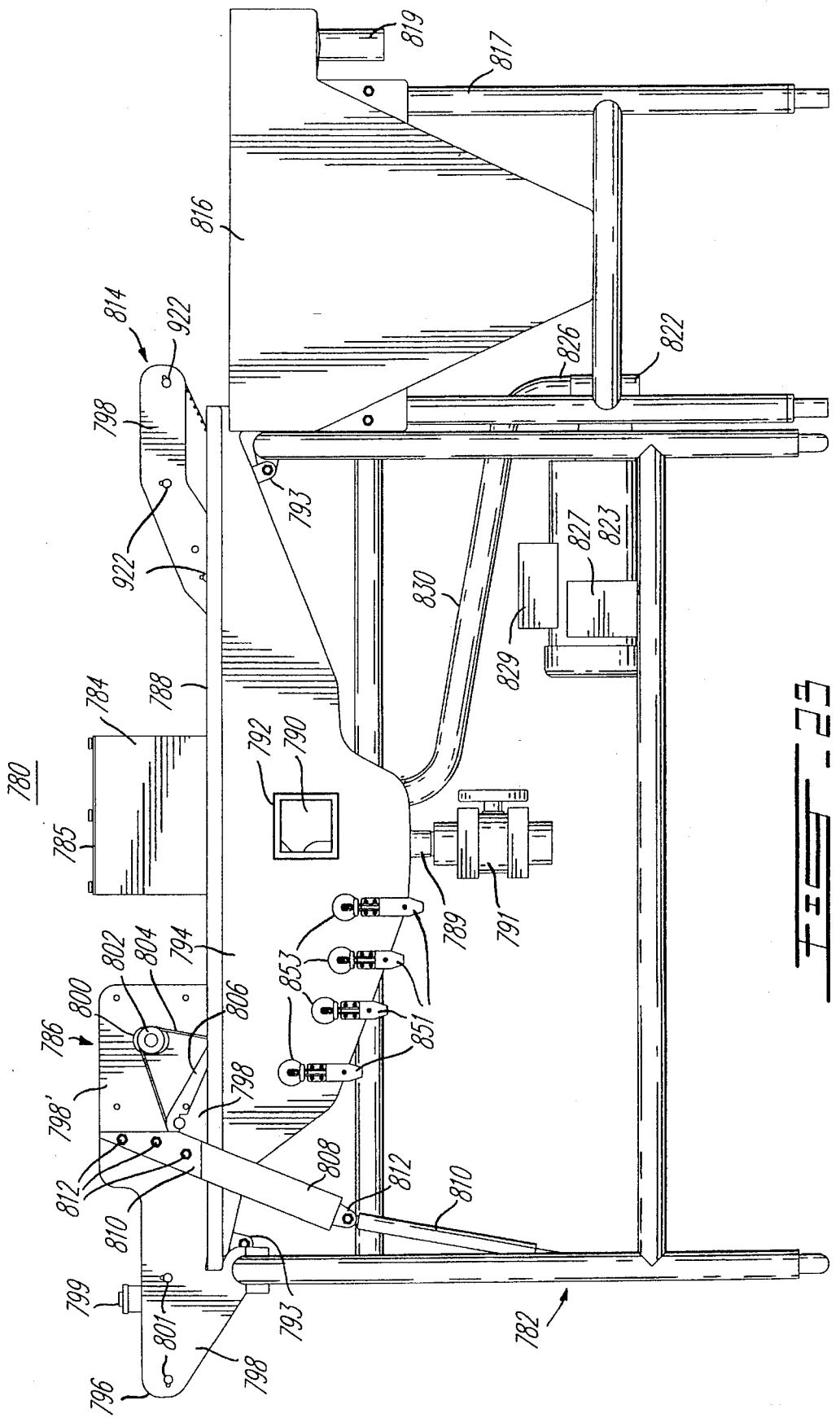

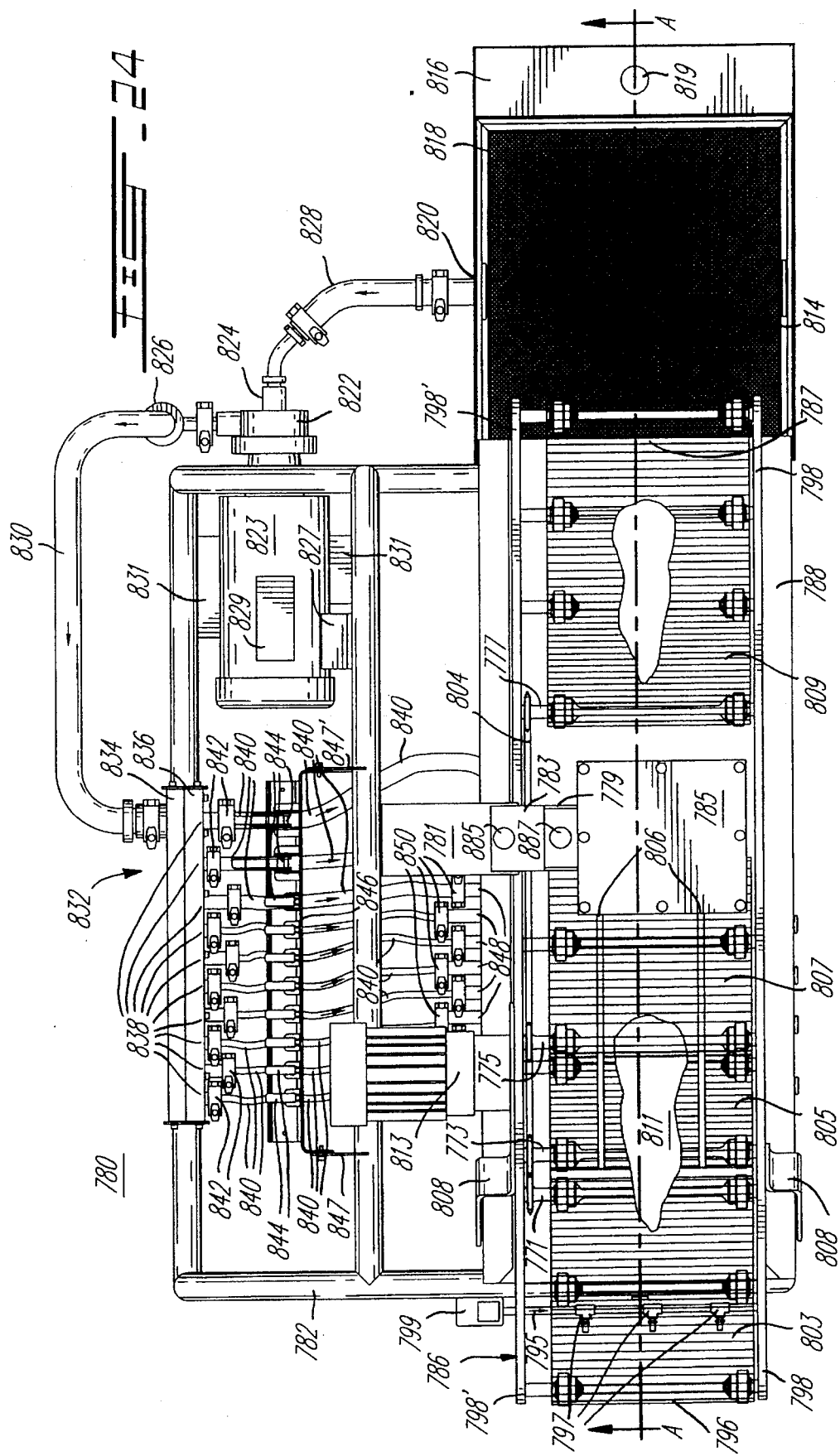

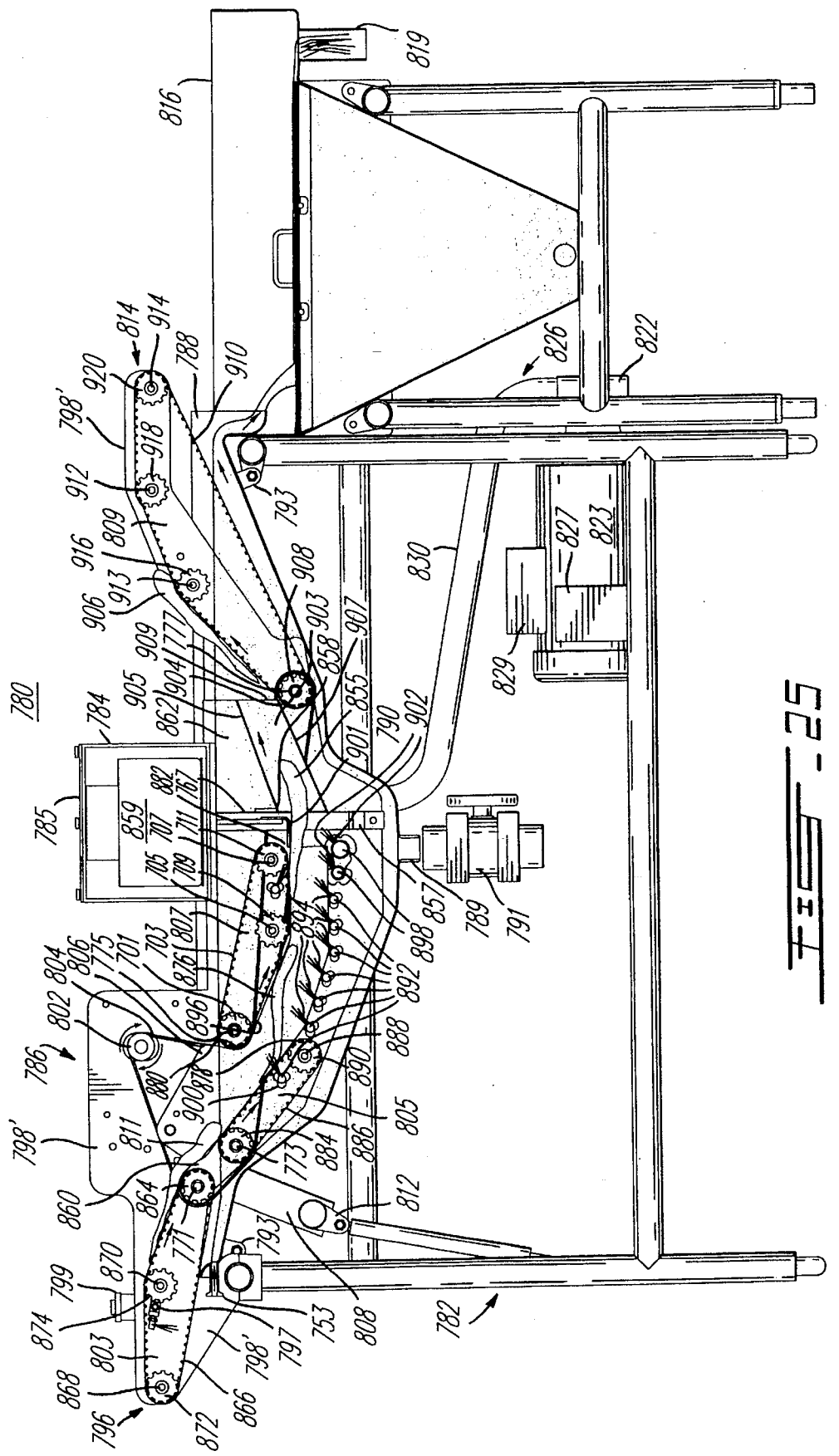

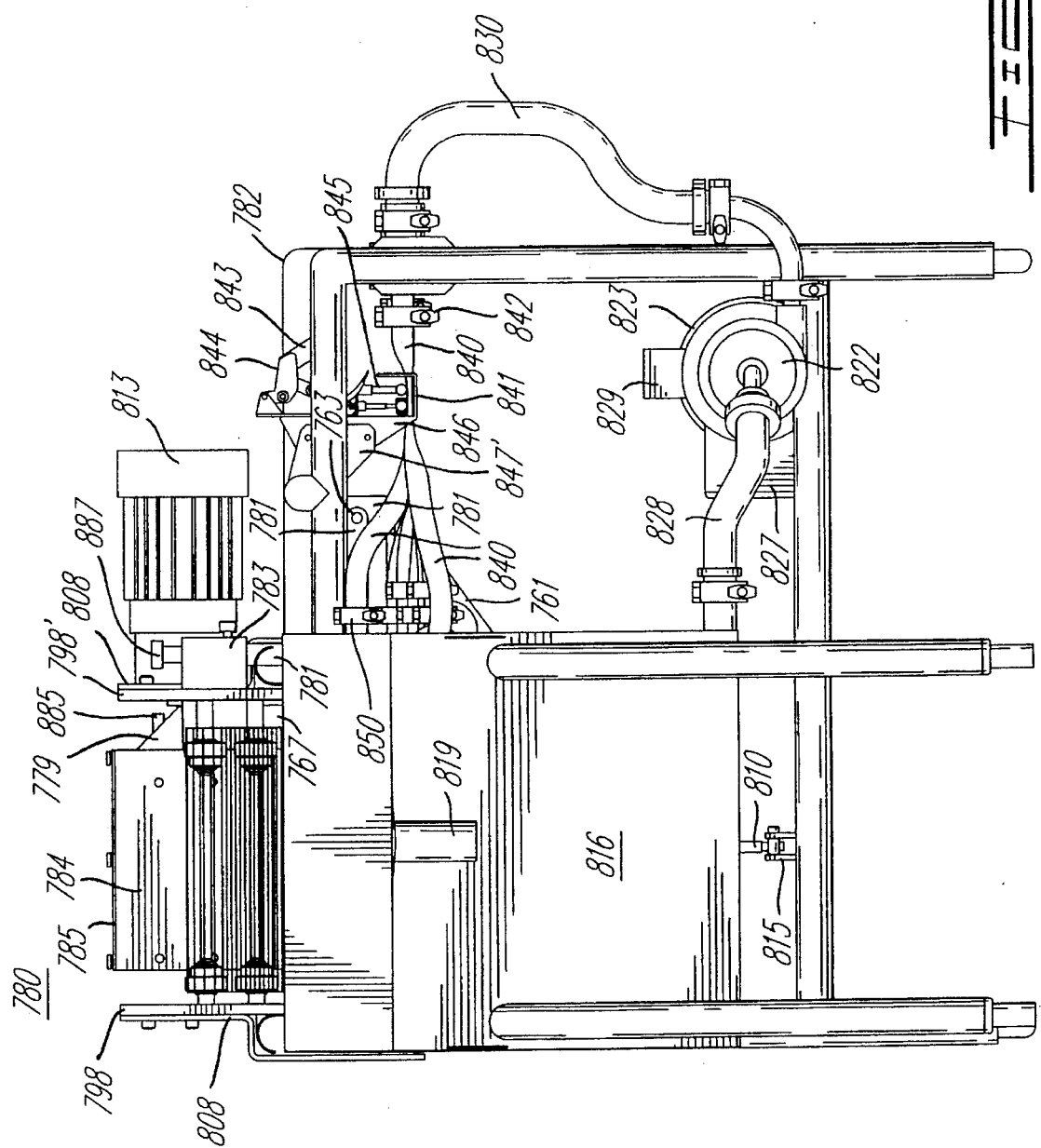

ULTRASONIC TRANSMISSION IMAGING APPARATUS AND METHOD

FIELD OF THE INVENTION

The present invention relates to ultrasonic imaging apparatus and method for producing focused acoustic images of objects or portion of objects using transmitted ultrasonic waves, and relates more particularly to an imaging apparatus used for fish fillet inspection.

DESCRIPTION OF PRIOR ART

In the field of acoustic imaging, two main imaging principles have been heretofore used in imaging apparatus for medical or industrial purposes, namely acoustic echo imaging and acoustic transmission imaging.

Typically, acoustic echo imaging apparatus comprise an array of ultrasonic transducers which are used to successively produce a beam of acoustic waves toward an object or subject's body part under examination and to receive a corresponding reflected wave. Acoustic echo imaging apparatus generally produce B-scan images which lie in a plane containing the propagating waves, through successive electrical excitation of the transducers forming the array in a sweeping mode. Furthermore, it is well known in the art that in a case where a phased array is used, a dynamic focusing of the ultrasonic acoustic beam can be obtained either during emission or reception of the ultrasonic waves. In dynamic emission focusing, each of the transducers comprised in the phased array is activated by the ultrasonic generator through a delay circuit, whereby wave amplitude of the ultrasonic beams coming from all transducers of the array adds up at a given point on a focal plane at the surface of or within the object or human body's part to which ultrasonic beams are directed. In dynamic reception focusing, reflected waves propagating back from a given point at the surface of or within the object or subject's body part are sensed by the transducers of the array which have been previously switched to a receiving mode. A delay circuit comprising a plurality of delay lines respectively connected to array transducers outputs, which delay lines providing proper delays depending upon the distance between a given target reflexion point and the respective transducers. Such dynamic reception focusing is employed in Acoustic echo imaging apparatus as disclosed in U.S. Pat. No. 4,730,495 to Green and in U.S. Pat. No. 4,553,437 to Luthra et al. Alternately, emission or reception dynamic focusing can be provided in acoustic echo imaging through detection of amplitude and phase information carried by reflected waves, followed by proper signal phase shifting and adding, as disclosed in U.S. Pat. No. 3,805,596 to Klahr.

Previously known ultrasonic transmission imaging apparatus producing C-scan images, such as those disclosed in U.S. Pat. No. 4,179,936 to Bennet et al. and in U.S. Pat. No 3,937,066 to Green et al., generally use conventional optical ultrasonic focusing techniques, which do not provide dynamic focusing capabilities yielding to high image resolution within minimum processing time, as required in many applications, such as medical diagnostic, nondestructive testing or fish fillet inspection.

The goal of marketing quality fish products has made detection of parasites in fish fillets an essential procedure for the fish processing industry. In the past years, light candling tables such as the one disclosed in U.S. Pat. No. 4,744,131 to Hartmann et al. have been extensively used in the fish processing industry. In these light candling tables, fish fillets are guided to a light emitter by means of a conveyer belt which is made of a material which allows light to pass therethrough. However, light candling tables inspection apparatus have an important drawback. In penetrating through the flesh, optical dispersion and other unwanted optical side effects occurs, which tend to limit image resolution and quality required to accurately detect parasites. Therefore, light candling tables generally allow accurate parasite detection limited to the fish fillet surface. Although images produced by a light candling table can be captured by a digital camera connected to an image processing system, image quality cannot be sufficiently enhanced to provide either visual of automated accurate parasite detection. Alternately, the ultrasonic echo imaging principle has been proposed, as in the ultrasonic fish fillet inspection apparatus disclosed in Canadian patent application No. 2058895 to Lemon et al. With such an ultrasonic echo imaging inspection apparatus, unwanted side effects such as ultrasonic waves dispersion occurs at an negligible level in a homogenous transmission medium such as water or flesh. However, with a foreign body showing round surface being embedded within the flesh, such as a fish parasite, only a small portion of incoming ultrasonic waves is effectively reflected back by a limited area of the foreign body toward the ultrasonic emitter/receiver unit, in a direction parallel to the incoming wave direction. The main portion of the incoming waves is reflected by an adjacent area on the foreign body surface, and dispersed in a plurality of substantially radial directions around the foreign body surface. As a result, reflected waves generally do not yield an accurate representation of the exact characteristic shape of a foreign body, and the relatively low level intensity of the reflected ultrasonic waves tends to accordingly limit the signal-to-noise ratio.

SUMMARY OF INVENTION

It is thus a feature of the present invention to provide an ultrasonic transmission imaging apparatus and method showing dynamic focusing capabilities.

Another feature of the present invention is to provide an ultrasonic transmission imaging apparatus and method producing good image resolution within a minimum processing time.

Another feature of the present invention is to provide an ultrasonic imaging apparatus and method used for real time fish fillet inspection.

According to the above features, from a broad aspect, the present invention provides an ultrasonic transmission imaging apparatus comprising an ultrasonic emitter for producing substantially continuous coherent ultrasonic waves toward an object to be inspected positioned in a detecting zone and surrounded by an ultrasonic coupling medium in contact with the object on opposed sides thereof, for providing transmission of the ultrasonic waves thereto, transfer of the ultrasonic waves therethrough, and transmission of object traversing ultrasonic waves out of the object. The apparatus further comprises an ultrasonic detectors array comprising a plurality of ultrasonic detectors for receiving the object traversing ultrasonic waves to a plurality of series of electrical signals coming from the ultrasonic detectors, the electrical signals characterizing transmission of the ultrasonic waves through the object. The series of electrical signals respectively characterize transmission of the ultrasonic waves through the object in a plurality of transmission planes substantially defined by the ultrasonic array, the series of electrical signals being respectively associated with a series of image elements. The apparatus further comprises a signal vector component detector adapted to receive the electrical signals, this signal vector component detector detecting signal vector components for each of the electrical signals, to produce pairs of first and second signal vector component signals corresponding to the electrical signals. There is also provided an analog-to-digital converter adapted to receive the pairs of first and second signal vector component signals for producing corresponding pairs of first and second signal vector component digital signals. The apparatus further comprises a computer for controlling the apparatus which is connected to the analog-to-digital converter for receiving the pairs of first and second signal vector component digital signals. The computer has a memory for storing the pairs of first and second signal vector component digital signals and for storing focusing function data establishing, for each image element comprised in a focusing aperture comprising a plurality of juxtaposed image elements of the series of image elements, a phase displacement value relative to a reference phase value associated with a focal line passing through a focus point and a center of the aperture. The computer uses the focusing function data to produce corresponding pairs of first and second resulting signal vector component digital signals forming a focused digital image representation of the object traversing ultrasonic waves.

Coherent in this context means that the ultrasonic wavefront is evenly in phase, whether the emitter is a single piece or made up of a number of component emitters.

According to a further aspect of the present invention, the apparatus is used as a fish fillet imaging apparatus, the object to be inspected being a fish fillet. The coupling medium is a mass of water traversing the detecting zone and surrounding the fish fillet to be inspected. The device for creating a scanning relative movement between the object to be inspected and the ultrasonic emitter and scanning ultrasonic detectors array is a fish fillet transport unit for immersing the fish fillet to be inspected in the water mass and in the detecting zone and for bringing an inspected fish fillet out of the water mass toward an output provided on the transport unit. The apparatus further comprises a frame on which are mounted the ultrasonic emitter, the scanning ultrasonic detectors array and the fish fillet transport unit. There is also provided a main tank mounted on the frame containing the detecting zone and filled with the water mass. The ultrasonic emitter and scanning ultrasonic detectors array are immersed in the water mass and are adjustably secured to the frame so as to be maintained in a stationary position within the main tank.

According to a still further broad aspect of the present invention, there is provided an ultrasonic transmission imaging method comprising the steps of: (i) producing substantially continuous coherent ultrasonic waves toward an object to be inspected positioned in a detecting zone; (ii) providing transmission of the ultrasonic waves to the object to be inspected, transfer of the ultrasonic waves therethrough and transmission of object traversing ultrasonic waves out of the object; (iii) receiving the object traversing ultrasonic waves and producing a plurality of series of electrical signals characterizing transmission of the ultrasonic waves through the object in a plurality of transmission planes, the series of electrical signals being respectively associated with a series of image elements; (iv) detecting signal vector components for each of the electrical signals and producing pairs of first and second signal vector component signals corresponding to the electrical signals; (v) digitally converting the pairs of first and second signal vector component signals and producing corresponding pairs of first and second signal vector component digital signals; (vi) providing focusing function data establishing, for each image element comprised in a focusing aperture comprising a plurality of juxtaposed image elements of the series of image elements, a phase displacement value relative to a reference phase value associated with a focal line passing through a focus point and a center of the aperture; and (vii) using the focusing function data to produce corresponding pairs of first and second resulting signal vector component digital signals forming a focused digital image representation of the object traversing ultrasonic waves.

BRIEF DESCRIPTION OF DRAWINGS

A preferred embodiment of the present invention will be now described with reference to the accompanying drawing in which:

FIG. 1 is a schematic three-dimensional view of an ultrasonic unit comprised of an emitter head and scanning detectors array head, with an object to be inspected being in relative movement therebetween, according to a first example of the present invention.

FIG. 2A is an underside partial view of the ultrasonic scanning detectors array along line 2A—2A of FIG. 1, showing rectangular ultrasonic detectors.

FIG. 2B is a partial side view along line 2B—2B of FIG. 2A showing physical focusing along the Y axis of the received ultrasonic waves.

FIG. 3A is an underside partial view of the ultrasonic scanning detectors array along line 2A—2A of FIG. 1, showing square detector cells.

FIG. 3B is a partial side view along line 3B—3B of FIG. 3A, showing direct receiving of ultrasonic waves without physical focusing.

FIG. 4A is an underside partial view of the ultrasonic emitter along line 4—4 of FIG. 1.

FIG. 4B is a partial side view along line 44 of FIG. 4A, schematically showing physical focusing along Y axis of the emitted ultrasonic waves.

FIG. 5 is a partial side view along line 4—4 of FIG. 4A schematically showing direct emission of plane ultrasonic waves without physical focusing.

FIG. 6 is a schematic view of a scanning path for the ultrasonic emitter and scanning detectors array unit which are shown in relative displacement with reference to a large object to be inspected.

FIG. 7 is a schematic three-dimensional view of a stationary ultrasonic unit comprised of an emitter head and a two-dimensional detectors array head respectively having emitting and detecting surface dimensions greater than the corresponding surface of an object to be inspected positioned therebetween, according to a second example of the present invention.

FIG. 8A is an underside partial view of the ultrasonic two-dimensional detectors array along line 8—8 of FIG. 7.

FIG. 8B is a side view of the ultrasonic two-dimensional detectors array as shown in FIGS. 7 and 8A, showing direct receiving of ultrasonic waves without physical focusing.

FIG. 13A is a three-dimensional plot of the focusing function first vector component data on the Z axis, with respect to position coordinates along directions parallel and perpendicular to the aperture as shown in FIG. 12, respectively represented by X and Y axis, according to a complex domain representation of the focusing function.

FIG. 13B is a three-dimensional plot of the focusing function second vector component data on the Z axis, with respect to position coordinates along directions parallel and perpendicular to the aperture as shown in FIG. 12, respectively represented by X and Y axis, according to a complex domain representation of the focusing function.

FIG. 14A is a three-dimensional plot of the focusing function amplitude data on the Z axis, with respect to position coordinates along directions parallel and perpendicular to the aperture as shown in FIG. 12, respectively represented by X and Y axis, according to a polar representation of the focusing function.

FIG. 14B is a three-dimensional plot of the focusing function phase data on the Z axis, with respect to position coordinates along directions parallel and perpendicular to the aperture as shown in FIG. 12, respectively represented by X and Y axis, according to a polar representation of the focusing function.

FIG. 21 is an electronic circuit diagram of a first (SIN) synchronous detection circuit section provided on the circuit as shown in FIG. 17A.

FIG. 22 is an electronic circuit diagram of a second and quadrature phased (COS) signal vector component detection device provided on the circuit as shown in FIG. 17A.

FIG. 23 is a front view of a fish fillet ultrasonic imaging apparatus embodying the present invention.

FIG. 24 is a plan view of the fish fillet ultrasonic inspection apparatus as shown in FIG. 23.

FIG. 25 is a cross-sectional view along line A—A of FIG. 24.

FIG. 26 is a side view of the output end of the apparatus as shown in FIG. 23.

DESCRIPTION OF PREFERRED EMBODIMENTS

Figures 9A, 9B:
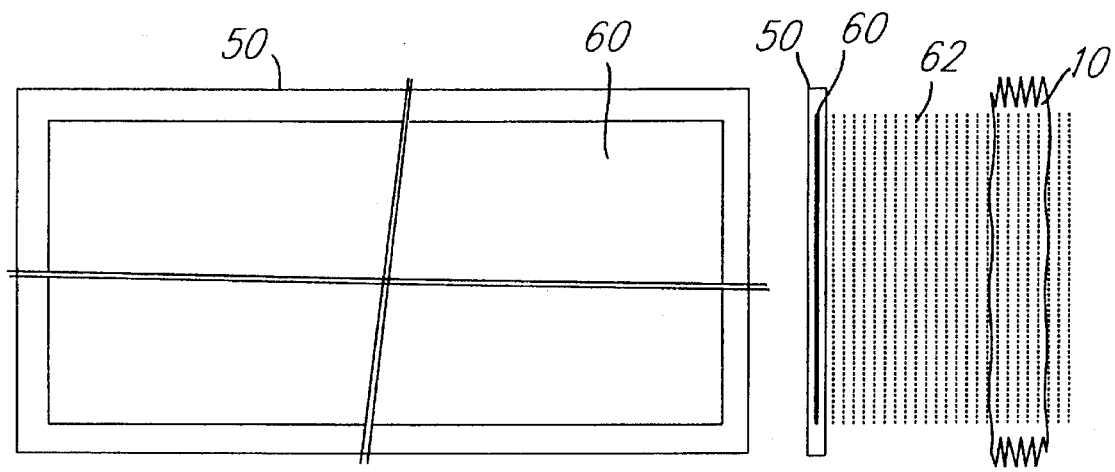
FIG. 9A is an underside partial view of the ultrasonic emitter along line 9—9 of FIG. 7.
FIG. 9B is a side view of the ultrasonic emitter as shown in FIGS. 7 and 9A, showing direct emission of plane ultrasonic waves without physical focusing.

Referring now to FIG. 1, according to a first example of the present invention, an object 10 to be inspected, or a subject's body part, is shown as being in relative movement along an X axis 11 with reference to an ultrasonic unit generally designated at numeral 12, which is comprised of an ultrasonic emitter head 14 and a scanning detector head 16. The emitter head 14 and scanning detector head 16 are immersed in an ultrasonic coupling medium and are mutually aligned in a spaced parallel relationship so as to form a detection zone 18 therebetween traversed by ultrasonic beam which intersects a moving inspection portion 19 of the object as it is displaced relative to the ultrasonic unit, whereby the entirety of the object is being inspected.

Turning now to FIG. 2A, according to a preferred ultrasonic unit configuration, the ultrasonic detectors head 16 comprises a linear array 20 of rectangular ultrasonic detectors 22 which are aligned side by side with respect to their length. The detector width dx is chosen as small as possible so as to provide high imaging resolution in a direction parallel to X axis, while minimizing mutual coupling between adjacent detectors. An ultrasonic piezoelectric detectors array, typically having detector width under 0.3 mm, which is currently available on the market, can generally provide image resolution as required by many usual applications.

Turning now to FIG. 2B, the detector head 16 preferably comprises an ultrasonic lens 25 covering ultrasonic detectors linear array 20 and showing a concave profile in the X-Z plane so as to provide physical focusing of the received ultrasonic waves along both Y and Z axis as represented by a wave cone 21 coming from a focal point 23 comprised in a focal plane 24 traversing the inspected object 10. Alternately, a curved ultrasonic detector linear array (not shown) can be used to provide physical focusing along Y and Z axis. As will be later explained in more detail, such physical focusing is proposed as an additional feature when dynamic focusing according to the present invention is mainly performed in a single main direction, after having dynamically set the position of focal point 23 along the Z axis, which main direction is parallel to X axis in an example as shown in FIG. 2B. Although unidirectional dynamic focusing would be suitable in most imaging applications, bidirectional dynamic focusing can be implemented as well, especially with a linear array configuration as shown in FIG. 3A, where the ultrasonic detectors head 16 comprises a linear array 26 of substantially square ultrasonic detectors 28 which are aligned side by side along the ultrasonic detector head 16. Detector dimensions dx and dy are chosen as small as possible so as to provide high imaging resolution in both directions respectively parallel to X and Y axis. Dynamic focusing as applied for both directions eliminates a need for physical focusing, the linear array 20 directly receiving from a given area of the object 10 substantially flat ultrasonic waves 30 traversing therethrough, as shown in FIG. 3B.

Referring now to FIG. 4A, the ultrasonic emitter head 14 comprises an ultrasonic transducer 32 having preferably at least the same area as the detectors linear arrays as shown in FIG. 2A or 3A, whereby the detection zone is entirely traversed by a substantially uniform emitted ultrasonic wave beam produced by the ultrasonic transducer 32. Either a monopiece ultrasonic transducer or a composite transducer formed by an assembly of several discrete transducers can be used, provided each transducer is driven by essentially a same electrical signal whose characteristics will be presented later in detail.

Turning now to FIG. 4B, the ultrasonic emitter head 14 preferably comprises an ultrasonic lens 34 covering the transducer 32 and showing a concave profile in the Y-Z plane so as to provide physical focusing of the received ultrasonic waves along both Y and Z axis as represented by a wave cone 36 coming from a focal point 38 comprised in a focal plane 40 traversing the inspected object 10. As mentioned earlier, a curved ultrasonic linear detector array (not shown) can alternately be used to provide physical focusing along Y and Z axis. In cases where physical focusing at emission in not required, the emitter transducer 32 directly produces toward the object 10 to be inspected substantially flat ultrasonic waves 42, as shown in FIG. 5.

Referring now to FIG. 6, there is schematically shown a scanning path 44 along with the ultrasonic unit 12 as earlier mentioned with respect to FIG. 1 is in relative displacement with reference to a large object 10 to be inspected, so as to ensure that the entirety thereof is inspected.

Referring now to FIG. 7, according to a second example of the present invention, there is schematically shown an ultrasonic unit 48 comprised of an emitter head 50 and a two-dimensional detectors array head 52 respectively having emitting and detecting surface dimensions greater than a corresponding surface of an object 10, or subject's body part, to be inspected positioned therebetween. The emitter head 50 and detectors array head 52 are immersed in an ultrasonic coupling medium and are mutually aligned in a spaced parallel relationship so as to form a detection zone 54 therebetween traversed by ultrasonic beam which intersects the entirety of the object 10, for complete inspection thereof. The detector head 52 is provided with a two-dimensional array 55 of substantially square ultrasonic detectors 56, as can be better seen in FIG. 8A. It is pointed out that image acquisition can be carried out either for a stationary or moving object 10. In the latter case, the speed of the object should be limited to a maximum value which depends upon the acquisition time of the apparatus. Detector dimensions dx and dy are chosen as small as possible so as to provide high imaging resolution in both directions respectively parallel to X and Y axis. As earlier mentioned with reference to FIG. 3B, dynamic focusing as applied for both directions eliminates a need for physical focusing, the two-dimensional detectors array 55 directly receiving from a given area of the object 10 substantially flat ultrasonic waves 58 traversing therethrough, as shown in FIG. 8B.

Referring now to FIG. 9A, the ultrasonic emitter head 50 comprises an ultrasonic transducer 60 having preferably at least the same area as the detectors two-dimensional array as shown in FIG. 8A, whereby the detection zone is entirely traversed by an emitted ultrasonic wave beam produced by the ultrasonic transducer 60. As earlier mentioned with reference to FIG. 4A, either a monopiece ultrasonic transducer or a composite transducer formed by the assembly of several discrete transducers can be used, provided each transducer is driven by essentially a same electrical signal whose characteristics will be presented later in detail. The emitter transducer 60 directly produces toward the object 10 to be inspected substantially flat ultrasonic waves 62, as shown in FIG. 9B.

Figure 10:
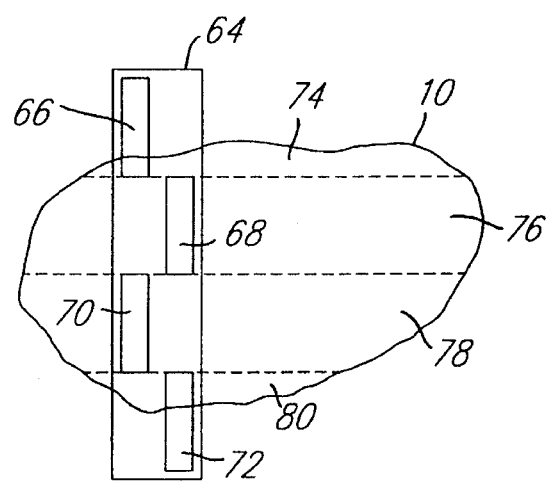
FIG. 10 is a schematic plan view of a composite ultrasonic emitter and detectors array unit which is comprised of a plurality of ultrasonic sub-units including detectors arrays a those shown in FIGS. 2A, 3A or 8A and the corresponding emitter transducers as those shown in FIG. 4A or 9A.

Referring now to FIG. 10, there is schematically shown a composite ultrasonic emitter and detectors array unit 64 which is comprised of a plurality of ultrasonic sub-units 66, 68, 70 and 72 which include ultrasonic detector arrays as those shown in FIGS. 2A, 3A or 8A and corresponding emitter transducers as those shown in FIG. 4A or 9A. During the scanning relative displacement of a large object 10 to be inspected, detection zone portions associated with sub-units 66, 68, 70, and 72 sweep object's complementary portions 74, 76, 78 and 80 respectively, whereby the entirety of object 10 is inspected.

Figure 11:
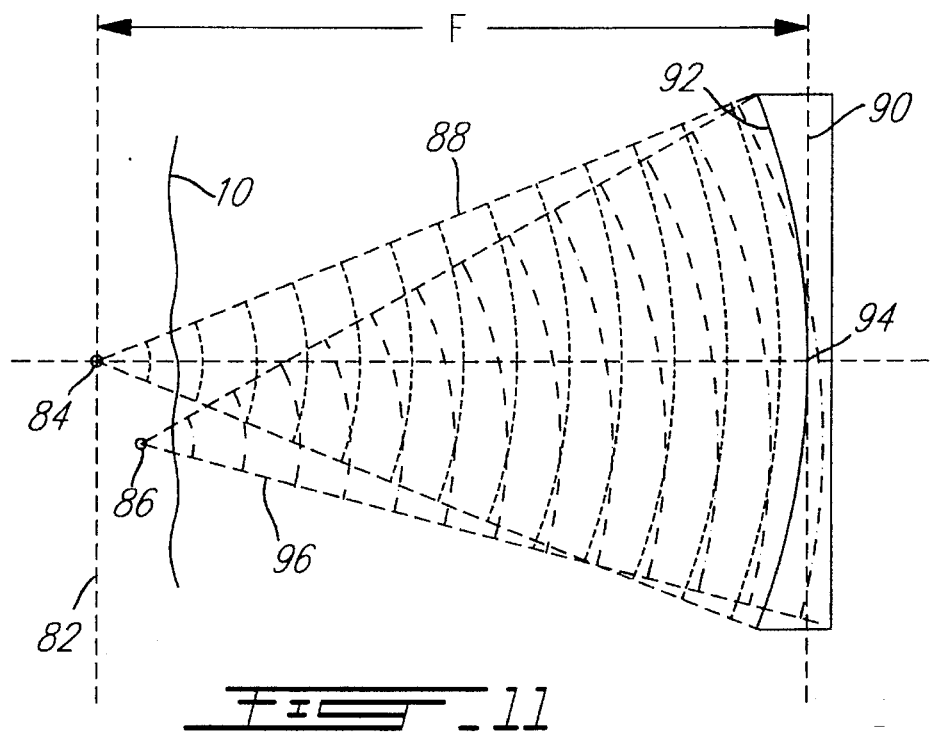
FIG. 11 is a schematic diagram illustrating the physical principle underlying focusing capabilities of the present invention.

Referring to FIG. 11, the physical principle underlying focusing capabilities of the present invention will be now explained, with reference to an hypothetical physical focusing detector. In FIG. 11, there is shown two points 84 and 86 positioned within an object 10 under ultrasonic inspection. The point 86 is comprised in an object imaging plane perpendicular to the wave transmission plane and represented by dotted line 82. The point 84 emits transmitted ultrasonic waves, schematically represented by a waves cone 88, toward an hypothetical detector 90 whose detecting surface 92, having its center point 94 being perpendicularly aligned with point 84, shows a circular arc profile characterized by a same radius at a distance F from the point 84 as the corresponding radius of the wavefront arriving at the surface 92. As a consequence, all points of the wavefront reach the surface 92 exactly in phase, thereby additively contributing to a resulting signal to be produced by the detector 90. At the same time, as opposed to transmitted ultrasonic waves coming from the point 84, transmitted ultrasonic waves coming from the point 86, as schematically represented by a waves cone 96, intersect the surface 92 of the detector 90 according to a continuous phase range. Mutually destructive effects of opposed phased waves yield to an overall negligible contribution on the resulting signal produced by the detector 90. Similar results can be basically obtained by dynamic focusing as proposed in the present invention, as will be now explained with reference to FIG. 12. A point 98, which is positioned within an object 10 under ultrasonic inspection, is comprised in an object imaging plane perpendicular to the wave transmission plane which is represented by a dotted line 100. The point 98 emits transmitted ultrasonic waves, which are partially represented by waves portions propagating along first and second propagation directions lines 102 and 103. Associated transversal amplitude waveforms 105 and 106 are respectively superimposed on the direction lines 102 and 103, as will be hereunder explained in more detail. An ultrasonic detectors array 101, which could be either a linear or a two-dimensional array, comprises a plurality of ultrasonic detectors 107 to 121 adapted to receive the object traversing ultrasonic waves for producing at an output provided on the array 101, which output being represented as a plurality of detectors outputs 122 to 136, a plurality of series of electrical signals coming from the ultrasonic detectors 107 to 121, these electrical signals characterizing transmission of the ultrasonic waves through the object 10. More specifically, in a case where a scanning ultrasonic linear detectors array is used, by means of a scanning relative movement between the object to be inspected and the ultrasonic emitter and scanning ultrasonic detectors array, the series of electrical signals are successively produced. These series of electrical signals respectively characterizes transmission of the ultrasonic waves through the object in a plurality of transmission planes substantially defined by the scanning ultrasonic detectors array and a direction perpendicular thereto and to the emitter, as the object to be inspected is being displaced relative to the ultrasonic emitter and scanning ultrasonic detectors array. These series of electrical signals are respectively associated with corresponding series of image elements. Alternately, in a case where a two-dimensional ultrasonic detectors array is used, the array comprises a plurality of rows of ultrasonic detectors disposed in a parallel relationship and adapted to receive the object traversing ultrasonic waves for producing at an output thereof a plurality of corresponding series of electrical signals coming from the ultrasonic detectors. These series of electrical signals respectively characterizes transmission of the ultrasonic waves through the object in a plurality of transmission planes substantially defined by the rows of ultrasonic detectors and a direction perpendicular thereto and to the emitter. The series of electrical signals are respectively associated with corresponding series of image elements.

Figure 12:
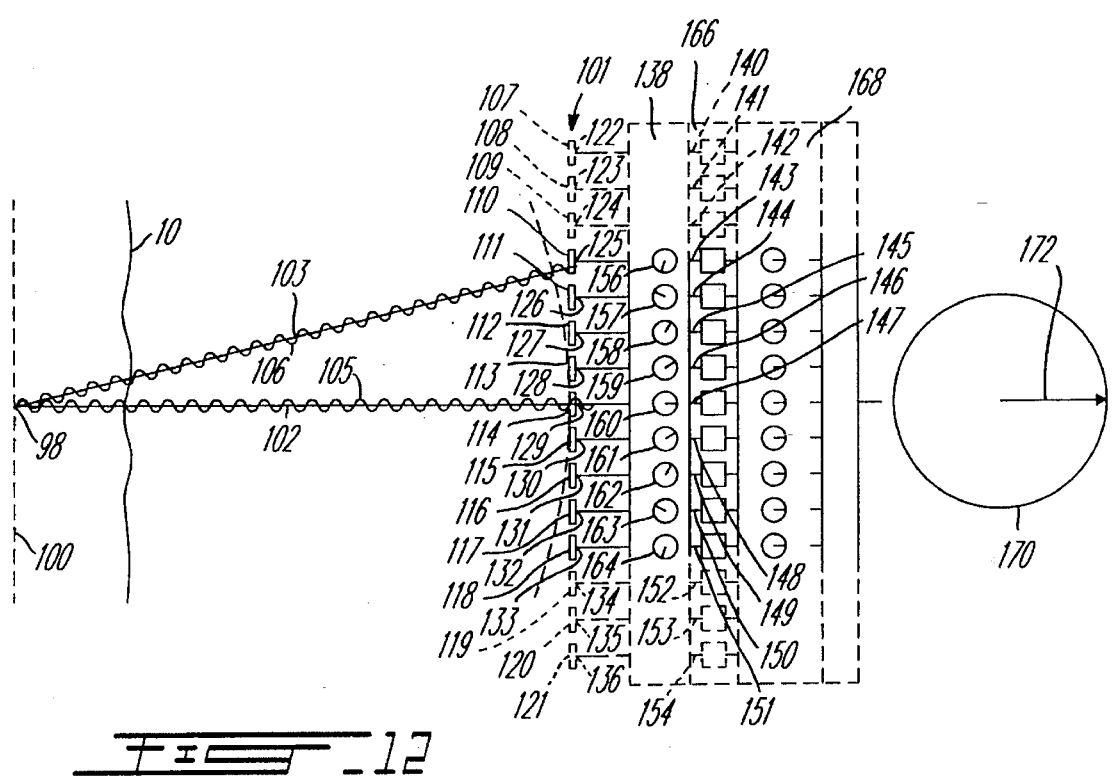
FIG. 12 is a schematic diagram of a focusing aperture provided in the present invention, showing the basic dynamic focusing principle used.

Returning to FIG. 12, a signal vector components detector device 138 is coupled to the output of the ultrasonic detectors array 101 for receiving the electrical signals. The signal vector components detector device 138 detects signal vector components for each of the electrical signals, to produce at an output thereof, represented as a plurality of outputs 140 to 154, a plurality of pairs of first and second signal vector component signals corresponding to the electrical signals. On circles 156 to 164 are graphically shown a polar representation of some vector signals, wherein only phase displacement are shown. However, amplitude displacement can also be considered in the processing to yield best results. An analog to digital converter 166 adapted to receive the pairs of first and second signal vector component signals is provided for sending to a computer 168 corresponding pairs of first and second signal vector component digital signals. Apart from a control function of the imaging apparatus, the computer 168 receives the pairs of first and second signal vector component digital signals and stores these signals in a memory (not shown). In a case where a scanning ultrasonic linear detectors array is used, the computer memory also contains focusing function data establishing, for each image element comprised in a focusing aperture comprising a plurality of juxtaposed image elements of the series of image elements, as the aperture formed by detectors 100 to 118 in an example as shown in FIG. 12, phase and amplitude displacement values relative to reference phase and amplitude values associated with a focal line, passing through a focus point and a center of the aperture. It is to be understood that image elements ca also be associated with electrical signals successively produced, during repetitive scanning acquisition steps, by one of the ultrasonic detectors 107 to 121. Alternately, in a case where a two-dimensional ultrasonic detectors array is used, the computer memory also contains focusing function data establishing, for each image element comprised in a focusing aperture comprising a plurality of juxtaposed image elements of the series of image elements, as the aperture formed by detectors 100 to 118 in an example as shown in FIG. 12, phase and amplitude displacement values relative to reference phase and amplitude values associated with a focal line passing through a focus point and a center of the aperture. It is to be understood that juxtaposed image elements can also be associated with electrical signals produced by adjacent ultrasonic detectors which are aligned in a direction perpendicular to the rows of ultrasonic detectors. It is pointed out that, depending upon the required resulting signal strength and processing time, for a given focus point positioned in the object 10, either all signals coming from the detectors 107 to 121 or a sub-group thereof, say the detectors 110 to 118 as shown in FIG. 12, could be chosen so as to form an aperture for the given focus point. In the latter case, a proposed method for establishing an aperture for each focus point positioned within or at the surface of the object, consists in positioning the center of aperture in alignment with each focus point and selecting a sub-group of detectors accordingly. As an example, an given focus point (not shown) which would be adjacent to focus point 98 could be associated with an aperture formed by detectors 109 to 117. The computer 168 uses the focusing function data to produce corresponding pairs of first and second resulting signal vector component digital signals. One of these pairs of first and second resulting signal, which corresponds to the focus point 98, is graphically represented on circle 170 in FIG. 12 as a polar vector 172. As a result, all pairs of first and second resulting signals form a digital image representation of the object traversing ultrasonic waves which is focused in the transmission planes or in transverse planes perpendicular to the transmission planes. Focalization can be simultaneously performed in both planes using focusing function data associated with all position coordinates intersecting a three-dimensional focusing aperture, as will be later explained in more detail with reference to FIGS. 13A to 14B. This digital representation can be further processed using usual image processing method, or being displayed on a display connected to the computer, after proper conversion of the pairs of first and second resulting signals into resulting amplitude signals which have to be compatible with gray levels of the display, as well known in the art.

Some functional details regarding the operation of the present invention will be now explained, with reference to FIG. 12 to 14B. In a case where a scanning ultrasonic linear array is used, the computer 168 detects the presence of an object 10 to be inspected, which is apparently moving in the detecting zone, prior to producing the corresponding pairs of first and second resulting signal vector component digital signals forming the digital image representation of the object traversing ultrasonic waves. Such a detection is performed by deriving a mean intensity value for consecutive pairs of first and second signal vector component digital signals corresponding to at least one of the successive series of electrical signals coming from the ultrasonic detectors, and by comparing this mean intensity value with a predetermined presence threshold value stored in the memory of the computer 168. For example, if detected intensity values stay lower than the predetermined presence threshold value more than a minimum given number of occurrences, that confirms to the computer the presence of an object to be inspected. A predetermined number of sample pairs of first and second signal vector component signals as produced by the signal vector components detector device 138, which signals correspond to series of electrical signals produced by the ultrasonic detectors 107 to 121 prior to the detection of an object passing into the detecting zone, are stored in the memory of the computer 168, for deriving correction parameter values, as will be later described in more detail. These parameter values are used by the computer 168, prior applying the focusing function, to compensate for detector sensitivity variation among ultrasonic detectors 107 to 121. When a set of proper correction parameters values is used for correcting an image produced while the detecting zone is empty of any object, each image element of the corrected image, as a target image, would be characterized by uniform amplitude and phase. Alternately, in a case where a two-dimensional detectors array is used, the computer 168 still detects the presence of an object 10 to be inspected in the detecting zone prior producing the corresponding pairs of first and second resulting signal vector component digital signals, by deriving a mean intensity value for a plurality of the pairs of first and second signal vector component digital signals corresponding with a plurality of electrical signals coming from the ultrasonic detectors, and then by comparing the mean intensity value with a predetermined presence threshold value stored in the memory of the computer 168. Similarly to the prior case, a predetermined number of sample pairs of first and second signal vector component signals as produced by the signal vector components detector device 138, which signals correspond to series of electrical signals produced by all rows of ultrasonic detectors 107 to 121 of the two-dimensional array prior to the detection of an object passing into the detecting zone, are stored in the memory of the computer 168, for deriving correction parameter values, as will be later described in more detail. These parameter values are used by the computer, prior applying the focusing function, to compensate for detector sensibility variation among rows of ultrasonic detectors 107 to 121. In an apparatus according to the present invention using either a linear or two-dimensional array, whenever the presence of an object in the detection zone is detected, the computer 168 commands the signal vector components detector 138 to produce a predetermined number of pairs of first and second signal vector component signals sufficient to form at least one complete image frame, which signals are being stored in the computer memory after digital conversion by the A/D converter 166. As to the correction parameter discussed earlier, in a preferred embodiment of the present invention, the computer 168 compares correction parameter values with a predetermined correction threshold value to detect corresponding unusable detectors among ultrasonic detectors 107 to 121. The computer 168 then substitutes for first and second signal vector component signals corresponding with all unusable ultrasonic detectors respective first and second signal vector component signals corresponding to proximate usable ultrasonic detectors, which have been previously tested.

Referring now to FIGS. 13A and 13B, there are respectively shown in a graphic representation an example of focusing function first and second vector components data on z axis, which data is plotted with respect to position coordinates along directions parallel and perpendicular to the aperture as shown in FIG. 12, respectively represented by X and Y axis, according to a complex domain representation of the focusing function.

Turning now to FIG. 14A and 14B, there are shown respectively in a graphic representation the same focusing function as represented in FIG. 13A and 13B, but in terms of focusing function amplitude and phase data on Z axis, which data is plotted with respect to position coordinates along directions parallel and perpendicular to the aperture as shown in FIG. 12, respectively represented by X and Y axis, according to a polar representation of the focusing function. It can be seen from FIG. 14B that an electrical signal coming from an ultrasonic detector which is aligned with a given focus point will be associated with a null phase displacement value at an initial time or phase, as shown at numeral 174 on FIG. 14b. In a preferred embodiment of the present invention using convolution computation in the time domain, the first and second signal vector component digital signals are respectively associated in the complex domain with a real component value I and an imaginary component value Q, and the focusing function is defined accordingly, as shown in FIGS. 13A and 13B. Thus we have for a given signal vector B in complex cartesian notation:

$$B = I + iQ \quad (1)$$

which corresponds to the following expressions in polar coordinates:

$$B = A e^{i\phi} \quad (1)$$

with $$A = \sqrt{I^2 + Q^2} \quad (2)$$

$$\phi = \arctan\left(\frac{Q}{I}\right)$$

and with $$B = A\cos(\phi) + iA\sin(\phi) \quad (3)$$

wherein A and $\phi$ are respectively amplitude and phase of the signal vector $B = Ae^{i\phi}$. It is to be understood that either cartesian or polar coordinates can be used to derive signal vector B, focusing function data and correction parameter values.

In a general case, for an image frame consisting of K×L image elements, the correction parameter values can be derived from the following mathematical expressions:

$$A_{k,l} = AI_{k,l} + iAQ_{k,l} = \frac{T}{M_{k,l}} \quad (4)$$

$$M_{k,l} = \frac{i}{J} \sum_{j=0}^{J-1} S_{j,k,l} \quad (5)$$

$$S_{j,k,l} = SI_{j,k,l} + iSQ_{j,k,l} \quad (6)$$

wherein k and l are primary coordinates according to first and second axis X and Y of a cartesian reference system for the ultrasonic detector array and associated image elements, with k=0,K−1 and l=0,L−1;

$A_{k,l}$ is the correction parameter associated with one of the image elements having coordinates k and l, this correction parameter compensating for detector sensibility variation among corresponding ones of the ultrasonic detectors, as earlier mentioned;

$AI_{k,l}$ is a real component value of the correction parameter associated with one of the image elements having coordinates k and l;

$AQ_{k,l}$ is an imaginary component value of the correction parameter associated with one of the image elements having coordinates k and l;

T is a target parameter being characterized by a target uniform amplitude and phase values corresponding to a reference target image;

$M_{k,l}$ is a mean value of sample pairs of first and second signal vector component signals associated with one of the image elements having coordinates k and l, prior detecting the presence of an object apparently moving in the detecting zone;

J is a predetermined number of said sample pairs of first and second signal vector component signals;

$S_{j,k,l}$ is the signal vector of a sample j associated with one of the image elements having coordinates k and l; $SI_{j,k,l}$ is a real component value associated with the first signal vector component digital signals and corresponds to a real component value of the signal vector of a sample j associated with one of the image elements having coordinates k and l;

$SQ_{j,k,l}$ is an imaginary component associated with the second signal vector component digital signals and corresponds to an imaginary component value of the signal vector of a sample j associated with one of the image elements having coordinates k and l.

Through multiplication of the first and second signal vector component signals by vector components values of the corresponding correction parameter, a corrected signal vector is produced, as defined in the followings mathematical expressions:

$$C_{k,l} = A_{k,l} B_{k,l} = CI_{k,l} + iCQ_{k,l} \quad (7)$$

$$B_{k,l} = BI_{k,l} + iBQ_{k,l} \quad (8)$$

wherein $C_{k,l}$ is a corrected signal vector associated with one of the image elements having coordinates k and l;

$CI_{k,l}$ is a real component value associated with the first corrected signal vector component digital signals and corresponds to a real component value of the corrected signal vector associated with one of the image elements having coordinates k and l;

$CQ_{k,l}$ is an imaginary component value associated with the second corrected signal vector component digital signals and corresponds to an imaginary component value of the corrected signal vector associated with one of the image elements having coordinates k and l;

$B_{k,l}$ is a signal vector associated with one of the image elements having coordinates k and l;

$BI_{k,l}$ is a real component value associated with the first signal vector component digital signals and corresponds to a real component value of the signal vector associated with one of the image elements having coordinates k and l;

$BQ_{k,l}$ is an imaginary component value associated with the second signal vector component digital signals and corresponds to an imaginary component value of the signal vector associated with one of the image elements having coordinates k and l.

In a particular case where a linear detectors array is used, mathematical expressions (3) to (8) applied with choosing l=0 and L=0.

The computer uses the focusing function data to produce corresponding pairs of first and second resulting signal vector component digital signals, forming a digital image representation the object traversing ultrasonic waves which is focused in the transmission planes or in transverse planes perpendicular to the transmission planes.

Different approaches can be implemented in the computer to produce a focused digital image representation using focusing function data according to the present invention. A first preferred approach, which can be particularly suitable when the total number of image elements considered in the focused computation is relatively limited, consist in applying a convolution technique, which can be mathematically expressed according to the following mathematical relations:

$$D_{k,l} = \sum_{m=-M}^{M} \sum_{n=-N}^{N} C_{k-m,l-n} L_{m,n} = DI_{k,l} + iDQ_{k,l} \quad (9)$$

$$C_{k-m,l-n} = A_{k-m,l-n} B_{k-m,l-n} \quad (10)$$

$$B_{k-m,l-n} = BI_{k-m,l-n} + iBQ_{k-m,l-n} \quad (11)$$

-continued $$L_{m,n} = \frac{F_{m,n}}{L_{norm}} = LI_{m,n} + iLQ_{m,n} \quad (12)$$

$$F_{m,n} = FI_{m,n} + iFQ_{m,n} \quad (13)$$

$$L_{norm} = LI_{norm} + iLQ_{norm} \quad (14)$$

wherein:

m and n are secondary coordinates according to first and second axis X and Y of the cartesian reference system for the ultrasonic detector array and associated image elements, with m=−M,M and n=−N,N, the size of the focusing function data being equal to (2M+1)(2N+1);

$D_{k,l}$ is a resulting signal vector associated with one of the image elements having coordinates k and l;

$DI_{k,l}$ is a real component value of the first resulting signal vector component digital signals and corresponds to a real component value of the resulting signal vector associated with one of the image elements having coordinates k and l;

$DQ_{k,l}$ is an imaginary component value of the second resulting signal vector component digital signals and corresponds to an imaginary component value of the resulting signal vector associated with one of the image elements having coordinates k and l;

$C_{k-m,l-n}$ is a corrected signal vector associated with one of the image elements having coordinates k-m and l-n;

$A_{k-m,l-n}$ is the correction parameter associated with one of the image elements having coordinates k-m and l-n, $B_{k-m,l-n}$ is a signal vector associated with one of the image elements having coordinates k-m and l-n;

$BI_{k-m,l-n}$ is a real component value associated with the first signal vector component digital signals and corresponds to a real component value of the signal vector associated with one of the image elements having coordinates k-m and l-n;

$BQ_{k-m,l-n}$ is an imaginary component value associated with the second signal vector component digital signals and corresponds to an imaginary component value of the signal vector associated with one of the image elements having coordinates k-m and l-n;

$L_{m,n}$ is a normalized focusing function data corresponding to one of the image elements having coordinates m and n;

$LI_{m,n}$ is a real component value of the normalized focusing function data corresponding to one of the image elements having coordinates m and n;

$LQ_{m,n}$ is an imaginary component value of the normalized focusing function data corresponding to one of the image elements having coordinates m and n;

$L_{norm}$ is a focusing function normalization parameter;

$LI_{norm}$ is a real component value of the focusing function normalization parameter;

$LQ_{norm}$ is an imaginary component value of the focusing function normalization parameter;

$F_{m,n}$ is the focusing function data corresponding to one of the image elements having coordinates m and n;

$FI_{m,n}$ is a real component value of the focusing function data corresponding to one of the image elements having coordinates m and n;

$FQ_{m,n}$ is an imaginary component value of the focusing function data corresponding to one of the image elements having coordinates m and n.

So as to ensure that the resulting signal vector component digital signals are produced at a proper level, the focusing function data is preferably normalized prior to the computation of these digital signals. A preferred normalization parameter $L_{norm}$ can be expressed as follows:

$$L_{norm} = \sqrt{\sum_{m=-M}^{M} \sum_{n=-N}^{N} (F_{m,n} F_{m,n})} \quad (15)$$

which represent the square root of the self-scalar product of the focusing function.

In a particular case where the focusing computation is chosen to be carried out only according to a single axis, say axis X, mathematical expressions (9) to (15) applied with choosing l=0, L=0, N=0 and N=0.

A second focusing computation approach, according to the present invention, uses mathematical analysis techniques in the spatial frequency domain, such as Fourier transform techniques. Well known basic DFT (direct Fourier transform) or FFT (fast Fourier transform) algorithms such as those disclosed in "DFT/FFT Convolution Algorithmns" by Burrus and Parks, John Wiley and Sons, 1985, can be adapted to be used for the purposes of the present invention, which publication is herein incorporated by reference. The computer uses the same correction parameter as defined in equations (4) to (6) and normalized focusing function as defined in equation (12) to (14) hereabove set out. The computer applies a first DFT or FFT operation on the normalized focusing function data according to coordinates k or l to produce transformed focusing function data in the spatial frequency domain. A second DFT or FFT operation is then performed to values of the pairs of first and second corrected signal vector component digital signals according to coordinates k or l, to produce transformed signal vector component values in the spatial frequency domain. Then, the computer performs a multiplication of corresponding values of the transformed focusing function data and the transformed signal vector component values, followed by an inverse DFT or FFT operation on the result thereof to produce the corresponding pairs of first and second resulting signal vector component digital signals forming the digital image representation of the object traversing ultrasonic waves, which image representation is focused in the transmission planes or in transverse planes perpendicular to the transmission planes according to the following mathematical expression:

$$D_{k,l} = DI_{k,l} + iDQ_{k,l} \quad (16)$$

wherein:

$D_{k,l}$ is a resulting signal vector associated with one of the image elements having coordinates k and l;

$DI_{k,l}$ is a real component value of the first resulting signal vector component digital signals and corresponds to a real component value of the resulting signal vector associated with one of the image elements having coordinates k and l;

$DQ_{k,l}$ is an imaginary value of the second resulting signal vector component digital signals and corresponds to an imaginary component value of the resulting signal vector associated with one of the image elements having coordinates k and l.

It is pointed out that the DFT and FFT methods are particularly adapted to consider, for each focus point of an object to be inspected, a maximum aperture which would be formed by ultrasonic detectors 107 to 121 in the example as shown in FIG. 12.

Several focusing functions showing proper characteristics establishing phase displacement values, can be proposed in accordance to the present invention. Moreover, as earlier mentioned, some focusing function consider both amplitude and phase displacement. A preferred focusing function $F_{m,n}$, which is more specifically a filter function, can be expressed as follows:

$$FI_{m,n} = FI(x_m, y_n, \omega, \lambda, z) = \quad (17)$$

$$e^{-(x_m^2 + y_n^2) K(\omega,\lambda,z)} \cos\left[-\frac{\lambda z}{\pi \omega^2} (x_m^2 + y_n^2) K(\omega,\lambda,z)\right]$$

$$FI_{m,n} = FI(x_m, y_n, \omega, \lambda, z) = \quad (17)$$

$$e^{-(x_m^2 + y_n^2) K(\omega,\lambda,z)} \cos\left[-\frac{\lambda z}{\pi \omega^2} (x_m^2 + y_n^2) K(\omega,\lambda,z)\right]$$

$$K(\omega,\lambda,z) = \frac{\pi^2 \omega^2}{\lambda^2 z^2 + \lambda^2 \omega^4} \quad (19)$$

$$x_m = mdx \quad (20)$$

$$y_m = ndy \quad (21)$$

wherein:

$x_m$ and $y_n$ are physical position coordinates according to first and second axis X and Y of the cartesian reference system for the ultrasonic detectors array and associated image elements, and associated with one of the image elements having coordinates m and n;

$K(w,\lambda,z)$ is a wave propagation damping factor;

dx is physical dimension along X axis of the image elements dy is physical dimension along Y axis of the image elements w is a desired image resolution;

$\lambda$ is the wavelength of the ultrasonic waves;

z is the distance between the focus point and a nearest one of the ultrasonic detectors.

A hereabove mentioned, in the particular case as where the focusing computation is chosen to be carried out only according to a single axis, say axis X, mathematical expressions (13) to (16) applied with choosing n=0, N=0 and $y_n$=0.

Figure 15:
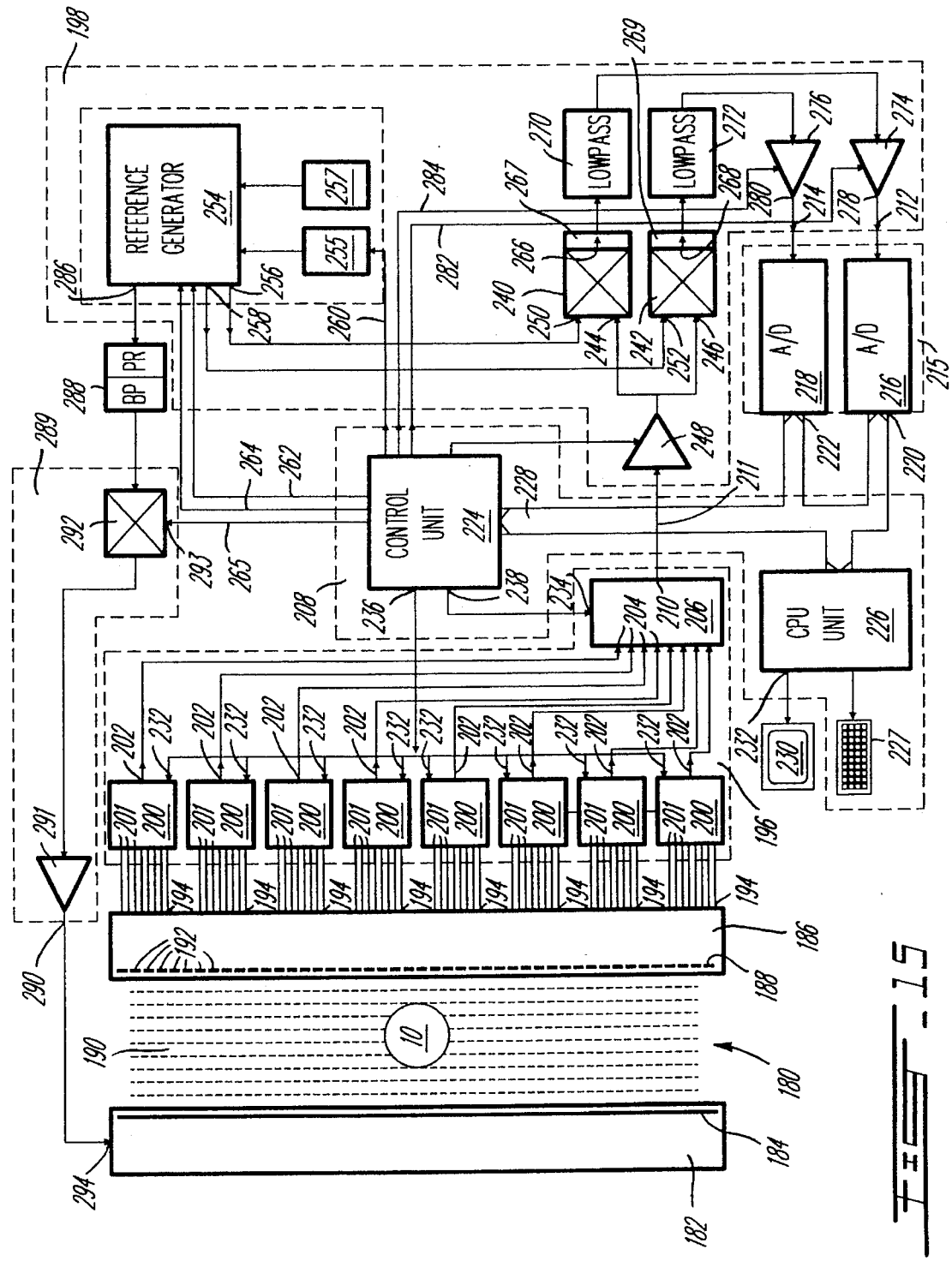
FIG. 15 is a schematic block diagram of the apparatus according to a first hardware embodiment of the present invention.

Referring now to FIG. 15, there is schematically shown a first hardware embodiment of the apparatus according to present invention, using a shared processing approach for the detection of signal vector components. An ultrasonic unit 180 comprises an ultrasonic emitter head 182 at the surface of which is mounted an ultrasonic emitter transducer 184, which could be either linear or two-dimensional, as earlier mentioned with reference to FIGS. 1 and 7. Facing the emitter head 182 in a parallel spaced relationship is an ultrasonic detector head 186, defining an inspecting zone 190 therebetween. At the surface of the ultrasonic detector head is mounted an ultrasonic detectors array 188, which could be either linear or two-dimensional as earlier mentioned with reference to FIGS. 1 and 7, which array 188 comprises a plurality of ultrasonic detectors 192. For the particular case of a two-dimensional array, there is provided a plurality of rows of ultrasonic detectors disposed in a parallel relationship. The emitter transducer 184 produces substantially continuous coherent ultrasonic waves toward an object 10 to be inspected positioned in the detecting zone 190. An ultrasonic coupling medium in contact with the object 10 at least on opposed sides thereof, provides transmission of the ultrasonic waves thereto, transfer of the ultrasonic waves therethrough, and transmission of object traversing ultrasonic waves out of the object 10.

For the particular case where a scanning linear detectors array is used, the ultrasonic detectors 192 are adapted to receive the object traversing ultrasonic waves for producing at an array output 194 a plurality of successive series of electrical signals coming from the ultrasonic detectors 192, which electrical signals characterizing transmission of the ultrasonic waves through the object 10. A scanning relative movement is created through the use of a suitable mechanical device (not shown) between the object 10 and the ultrasonic emitter head 182 and scanning ultrasonic detector head 186, whereby the series of electrical signals respectively characterizes transmission of the ultrasonic waves through the object 10 in a plurality of transmission planes substantially defined by the scanning ultrasonic detectors array 188 and a direction perpendicular thereto and to the emitter transducer 184 as the object 10 is being displaced relative to the ultrasonic emitter transducer 184 and scanning ultrasonic detectors array 188. The series of electrical signals are respectively associated with series of image elements.

For the alternate case where a two-dimensional ultrasonic detectors array is used, the ultrasonic detectors 192 are adapted to receive the object traversing ultrasonic waves for producing at the output 194 a plurality of corresponding series of electrical signals coming from the ultrasonic detectors, which series of electrical signals respectively characterizing transmission of the ultrasonic waves through the object in a plurality of transmission planes substantially defined by the plurality of rows of ultrasonic detectors and a direction perpendicular thereto and to the emitter transducer 184. The series of electrical signals are respectively associated with corresponding series of image elements.

A signal vector components detector circuit 198 is coupled through a multiplexer unit 196 to the output 194 of the ultrasonic detectors array 188 for receiving the electrical signals, and for detecting signal vector components for each of the electrical signals, to produce at outputs 212 and 214 provided on the signal vector components detector circuit 198, pairs of first and second signal vector component signals corresponding to the electrical signals. The multiplexer 196 preferably comprises a first stage of multiplexers 200, which stage typically comprises eight 64/1 multiplexers in a case where a scanning linear array of 512 ultrasonic detectors is used. The multiplexers 200 are provided with a plurality of inputs 201 respectively fed by each one of the electrical signals. Respective outputs 202 are provided on the multiplexers 200, which outputs are connected to a series of inputs 204 provided on an output multiplexer 206, which is a 8/1 multiplexer in a case where a scanning linear array of 512 ultrasonic detectors is used. Through a main output 210 provided on the output multiplexer 206, the electrical signals are sequentially transferred to the signal vector components detector circuit 198 through a line 211. The output multiplexer 206 is preferably provided with a preamplifier stage for amplifying each one of the electrical signals prior transferring thereof to the signal vector components detector circuit 198. An analog to digital converter unit 215 consisting of first and second A/D converters 216 and 218 are adapted to receive the pairs of first and second signal vector component signals for producing at outputs 220 and 222 thereof corresponding pairs of first and second signal vector component digital signals. A computer, generally designated at numeral 208, basically comprising a controller unit 224 interconnected through a main line bus 228 with a CPU 226 unit having a memory and a keyboard 227, controls the operation of the apparatus, and is connected through the main line bus 228 to the analog to digital converter unit 215 for receiving the pairs of first and second signal vector component digital signals as produced at the outputs 220 and 222, and for storing thereof in the computer memory. The computer memory also stores focusing function data in accordance to the present invention, the computer 208 using the focusing function data to produce corresponding pairs of first and second resulting signal vector component digital signals forming a digital image representation of the object traversing ultrasonic waves, as earlier explained in detail. So as to produce a visual display of the digital image representation of the object traversing ultrasonic waves, the apparatus may comprise a display 230 connected to the CPU unit 226 via a video output 232 provided thereon, for receiving amplitude signals produced by the CPU unit 226 and corresponding to the pairs of first and second resulting signal vector component digital signals. The computer 208 is connected to respective inputs 232 and 234 provided on the multiplexers 202 and 206 respectively through control outputs 236 and 238. In a preferred circuit configuration, the signal vector components detector circuit is a synchronous detector circuit comprising first and second multipliers 240 and 242 having respective signal inputs 244 and 246 coupled to the main multiplexer output 210 via the line 211 and an input amplifier 248. The multipliers 240 and 242 have respective reference inputs 250 and 252. The synchronous detector circuit 198 further comprises a reference signals generator 254 having first and second outputs 256 and 258 respectively connected to respective reference inputs 250 and 252 provided on the first and second multipliers 240 and 242, to respectively sent thereto a first synchronous reference signal and a second synchronous reference signal in phase quadrature with the first synchronous reference signal, and having calibration and reference oscillators 255 and 257, whose operation will be described in more detail with reference to FIGS. 17A and 18. It is pointed out that the synchronous reference signals may be sinusoidal or square waves reference signals, as will be later explained in more detail. The control unit 224 of the computer 208 is connected to the reference signals generator through lines 260, 262 and 264 for control thereof, as will be also later explained in detail with reference to FIGS. 17A and 18. The multipliers 240 and 242 further have respective outputs 266 and 268 for respectively producing, at a common operating frequency, a first signal comprising a primary signal vector component and a second signal comprising a secondary quadrature phased signal vector component. The synchronous detector circuit 198 further comprises first and second lowpass filters 270 and 272 respectively coupled to multipliers outputs 266 and 268 through intermediate amplifiers 267 and 269, and in series with respective first and second output amplifiers 274 and 276 for producing at first and second outputs 278 and 280 thereof the pairs of first and second signal vector component signals corresponding to the electrical signals coming from the ultrasonic detectors 192. The control unit 224 of the computer 208 is connected to the output amplifiers 274 and 276 respectively through control lines 282 and 284 for control thereof, as will be later explained in more detail with reference to FIGS. 17A to 22. The apparatus is further provided with an amplifier section 289 coupled to a third reference output 286 provided on the reference signal generator through a preamplifying and bandpass filtering section 288, to produce at an output 290 of a power amplifier 291 provided on the amplifier section 289 an amplified driving reference signal at the operating frequency. The third reference output 286 is adapted to sent a driving reference signal having the same operating frequency as the synchronous reference signals but with any phase characteristics, as will be hereunder explained in more detail. The control unit 224 of the computer 208 is connected through the line 265 to a second input 293 of a multiplier 292 provided on the amplifier section 289 for control thereof, as will be later explained in more detail with reference to FIG. 19. The ultrasonic emitter transducer 184 receives the amplified driving reference signal through an input 294 provided in the emitter head 182, for producing the required continuous coherent ultrasonic waves.

Mathematical basis for synchronous detection will be now explained. Suppose that the reference signal generator 254 is adapted to produce a sinusoidal driving reference signal at its third output 286, which driving reference signal is mathematically expressed as a time-dependent function r(t) defined as follows:

$$r(t) = \sin(\omega t) \qquad (22)$$

The ultrasonic wave signal as produced by the ultrasonic detectors array is a time-dependent function s(t) defined as follows:

$$s(t) = A \sin(\omega t + \phi) \qquad (23)$$

One can shows that:

$$s(t) = A \sin(\omega t + \phi) = A \cos\phi \sin(\omega t) + A \sin\phi \cos(\omega t) \qquad (24)$$

which is equivalent to express s(t) as a sum of two components in a form according to the following relations:

$$s(t) = I\sin(\omega t) + Q\cos(\omega t) \qquad (25)$$

$$I = A\cos\phi \qquad (26)$$

$$Q = A\sin\phi \qquad (27)$$

$$A = \sqrt{I^2 + Q^2} \qquad (28)$$

$$\phi = \arctan\left(\frac{Q}{I}\right) \qquad (29)$$

wherein I and Q are amplitudes of components of s(t) which are in phase quadrature, I being amplitude of a component of s(t) which is in phase with respect to the driving reference signal r(t) in the particular example as chosen. According to the synchronous detection technique, if s(t) is multiplied with a sin(ωt) signal, with the multiplier 240 in the example as shown in FIG. 15, we obtain:

$$\begin{aligned} s(t)\sin(\omega t) &= I\sin^2(\omega t) + Q[\cos(\omega t)\sin(\omega t)] \qquad (30)(31)(32)\\ &= \frac{I}{2}[-\cos(2\omega t) + 1] + \frac{Q}{2}\sin(2\omega t)\\ &= \frac{I}{2} + \frac{1}{2}[Q\sin(2\omega t) - I\cos(2\omega t)] \end{aligned}$$

since the first term of expression (32) is constant, while the second term is dependent upon (2ωt), the lowpass filter 270 essentially eliminates the latter term so as to only keep the constant term I/2. Therefore, whe obtain, after lowpass filtering, the first signal vector component signal expressed as follows:

$$B_1(t) = \frac{I}{2} \qquad (33)$$

If s(t) is now multiplied with a cos(ωt) signal, with the multiplier 242 in the example as shown in FIG. 15, we obtain:

$$\begin{aligned} s(t)\cos(\omega t) &= I\sin(\omega t)\cos(\omega t) + Q\cos^2(\omega t)\\ &= I\left[\frac{1}{2}\sin(2\omega t)\right] + Q\left[\frac{1}{2}[\cos(2\omega t) + 1]\right] \qquad (34)\\ &= \frac{Q}{2} + \frac{1}{2}[I\sin(2\omega t) + Q\cos(2\omega t)] \qquad (35) \end{aligned}$$

$$(36)$$

Here again, since the first term of expression (32) is constant, while the second term is dependent upon (2ωt), the lowpass filter 272 essentially eliminates the latter term so as to only keep the constant term Q/2. Therefore, whe obtain, after lowpass filtering, the second signal vector component signal expressed as follows:

$$B_2(t) = \frac{Q}{2} \qquad (37)$$

For practical purposes, square waves signals being easier to produce with available digital integrated circuits, reference signals may be square wave reference signals, provided phase characteristics as earlier defined are present. In such a case, it can be seen through Fourier series development that DC components of resulting $B_1(t)$ and $B_2(t)$ are still proportional to I and Q respectively.

Figure 16:
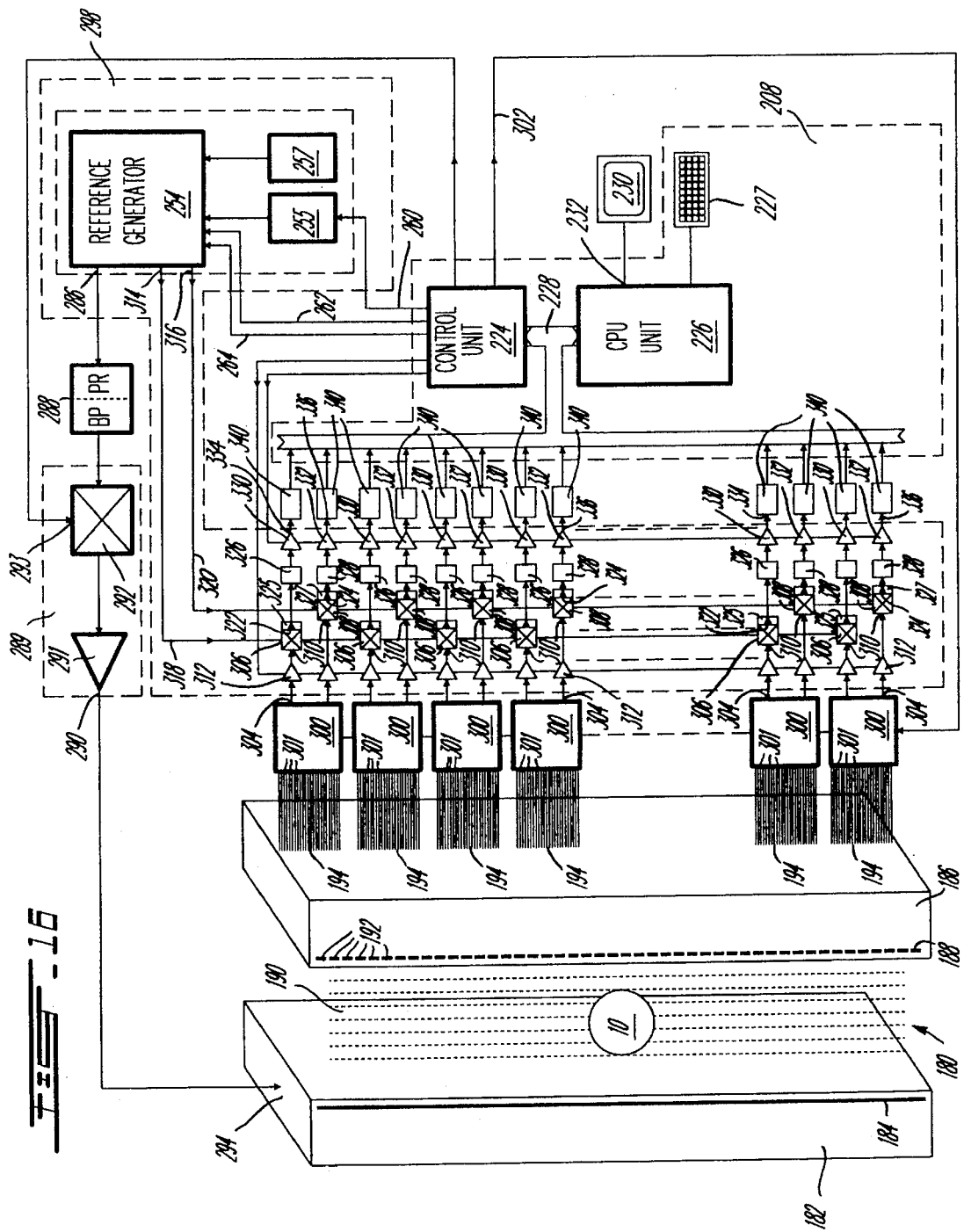
FIG. 16 is a schematic block diagram of the apparatus according to a second hardware embodiment of the present invention.

Referring now to FIG. 16, there is schematically shown a second hardware embodiment of the apparatus according to present invention, using a parallel processing approach for the detection of signal vector components. The apparatus as shown in FIG. 16 comprises essentially the same elements as those earlier described with reference to FIG. 15, except for the multiplexer, the signal vector components detector circuit and the analog to digital converter. Therefore, all details heretofore provided regarding these common elements, which are designated with same numerals in FIGS. 15 and 16, are relevant to the description of the apparatus as shown in FIG. 16, and need not to be repeated here. It can be seen from FIG. 16 that the signal vector components detector circuit 298 is coupled through a plurality of multiplexers 300 to the output 194 of the ultrasonic detectors array 188 for receiving the electrical signals, and for detecting signal vector components for each of the electrical signals. The control unit 224 of the computer 208 is connected to each of the multiplexers 300 through a plurality of control lines schematically represented as line 302 in FIG. 16, for control thereof. Each of the multiplexers 300 is provided with a plurality of inputs 301 respectively fed by a plurality of the electrical signals, and is further provided with a respective output 304 through which each electric signal comprised in the corresponding plurality of electrical signals is sequentially transferred to the signal vector components detector circuit 298. As a result, combined multiplexers 300 parallely transfer corresponding series of electrical signals to the signal vector components detector circuit 298. Each of the multiplexers 300 is preferably provided with a preamplifier stage (not shown) for amplifying each electrical signal prior its transfer to the signal vector components detector circuit 298. The signal vector components detector circuit 298 is comprised of a plurality of synchronous detector circuits comprising first and second multipliers 306 and 308 having respective signal inputs 310 coupled to respective ones of the multiplexer through a respective input amplifier 312 connected to the control unit 224 of the computer 208 for control purposes. Each input amplifier amplifies an incoming electrical signals prior its transfer to a corresponding multiplier 306 or 308. The signal vector components detector circuit 298 further comprises a reference signals generator 254 having first and second outputs 314 and 316 respectively connected, through a pair of series of parallel lines which are schematically represented as lines 318 and 320, to the respective reference inputs provided on the first and second multipliers 306 and 308, so as to respectively sent thereto a first synchronous reference signal and a second synchronous reference signal in phase quadrature with the first synchronous reference signal. The reference signals generator 254 further has calibration and main reference oscillators 255 and 257, whose operation will be described in more detail with reference to FIGS. 17A and 18. The control unit 224 of the computer 208 is connected to the reference signals generator 254 through lines 260, 262 and 264 for control thereof, as will be also later explained in detail with reference to FIGS. 17A and 18. The first and second multipliers 306 and 308 further have respective outputs 322 and 324 for respectively producing, at a common operating frequency, a first signal comprising a primary signal vector component and a second signal comprising a secondary quadrature phased signal vector component. Each of the synchronous detector circuits further comprises respective first and second lowpass filters 326 and 328 respectively coupled to corresponding multiplier outputs 322 and 324 through intermediate amplifiers 325 and 327, and in series with first and second output amplifiers 330 and 332 for producing at first and second outputs 334 and 336 thereof the pairs of first and second signal vector component signals associated with a corresponding electrical signal. The control unit 224 of the computer 208 is connected to the output amplifiers 330 and 332 for control thereof. The pairs of first and second signal vector component signals are converted in corresponding digital signals through respective analog to digital converters 340 connected to the output amplifiers 330 and 332. The CPU unit 226 of the computer 208 is connected through the main line bus 228 to the analog to digital converters 340 for receiving therefrom the pairs of first and second signal vector component digital signals, and for storing thereof in the computer memory. The computer memory also stores focusing function data in accordance to the present invention, the computer 208 using the focusing function data to produce corresponding pairs of first and second resulting signal vector component digital signals forming a digital image representation of the object traversing ultrasonic waves, as earlier explained in detail.

Figure 17:
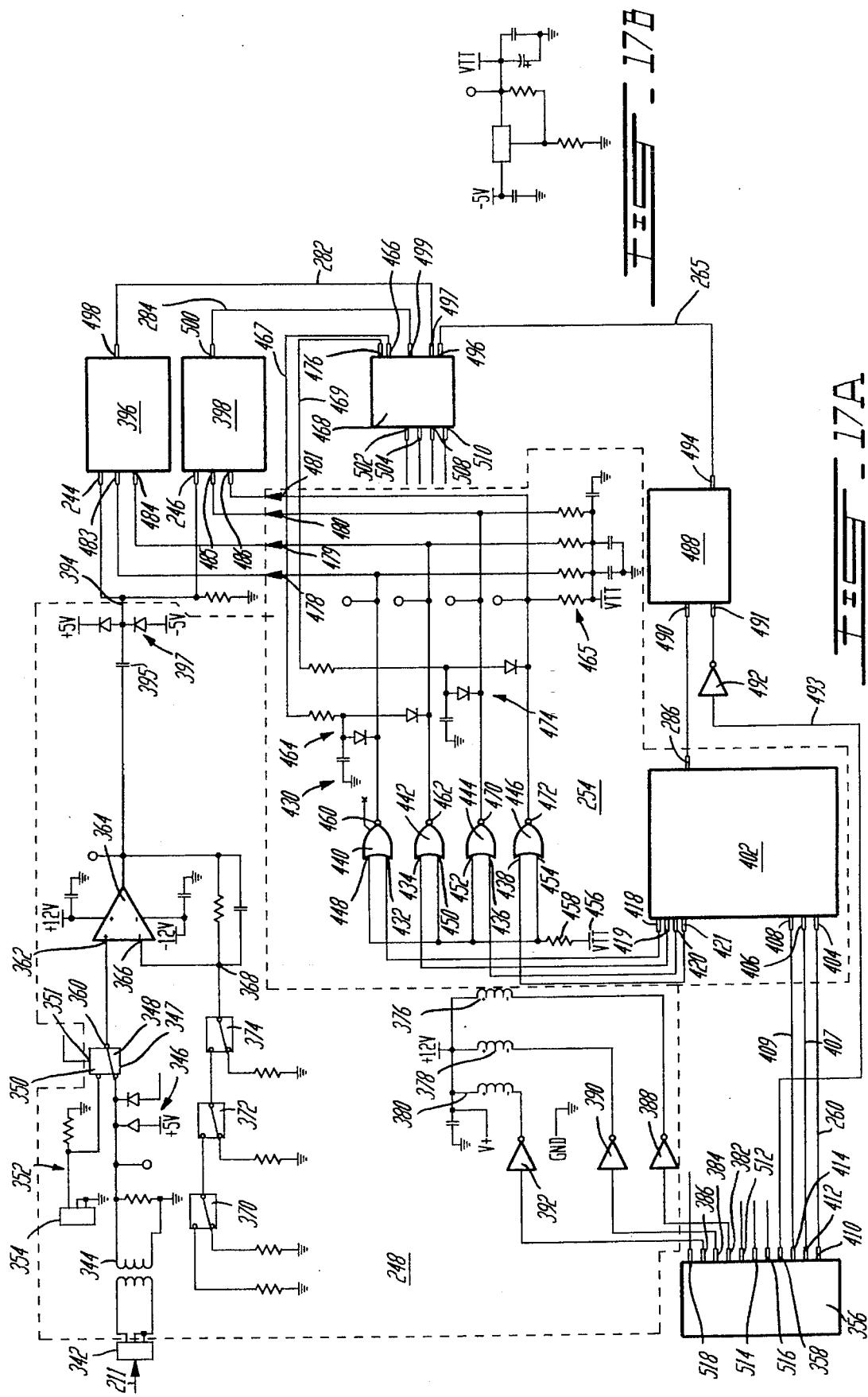
FIG. 17A, is a main electronic circuit diagram showing principal elements of the apparatus as shown in FIG. 15.
FIG. 17B is a power supply configuration for the input amplifier section as shown in FIG. 17A.

A detailed description of the apparatus as shown in FIG. 15 will be now presented with reference to FIGS. 17A to 22. In these latter figures, a same element will be generally designated with the same numeral as used in FIGS. 15. Referring to FIG. 17A, a main electronic circuit diagram showing principal elements of the apparatus is shown. The input amplifier 248 receives through the line 211 and terminal 342, successive series of electrical signals coming from the ultrasonic detectors. Passing through an isolation transformer 344 and with proper bias provided by a supply circuit 346, the electrical signals are fed to a first input port 347 of a controlled switch 350, having a second input port connected to a calibration signal input circuit 352 receiving a calibration signal through a connector 354 provided thereon. By feeding a calibration signal having known frequency and amplitude characteristics to the signal vector components detector circuit, proper gain and offset setting for the detector circuit can be verified by the computer through comparison with theoretical values of characteristic parameters, prior to receive electrical signals from the ultrasonic detectors array. The switch 350 is activated according to an inverted digital control signal $\overline{\text{OSCCAL2}}$ received at a control input 351 from an output 358 provided on a CPU bus 386 as part of the control unit of the computer (not shown). The resulting electrical signals are fed to a first port 362 of a differential amplifier 364, having a second port 366 connected to the output 368 of a programmable gain switching circuit comprising switches 370, 372 and 374 whose primary coils 376, 378 and 380 are respectively fed by inverted control signals coming from respective outputs of inverters 388, 390 and 392 respectively receiving digital control signals GAIN5, GAIN2 and GAIN1 coming from the CPU bus outputs 382, 384 and 386. Depending upon the values given to these three control signals by the computer, a predetermined gain value for the amplifier 364 is set. The computer can be programmed to set the gain according to amplitude level of electrical signals coming from the ultrasonic detectors array, which depends upon the ultrasonic transmissivity variations among different objects to be inspected. For the calibration operation, the gain is arbitrarily set to unity. The amplified electrical signals after being filtered by a high pass capacitor filter 395 and directed through a protection diodes circuit 397 are produced at an output 394 provided on the input amplifier 248 and parallely sent to the multiplier inputs 244 and 246 respectively provided on first (SIN) and second quadrature phased (COS) synchronous detection circuit sections 396 and 398, which sections will be later described with reference to FIGS. 21 and 22. The reference signals generator 254 comprises an oscillator circuit section 402, which will be later described with reference to FIG. 18, receiving at a first input 404, through the line 260 and from the output 410 provided on the CPU bus 356, a control digital TTL signal OSCCAL/T for enabling and disabling the calibration mode of the apparatus. The oscillator circuit section 402 further comprises second and third inputs 406 and 408 for receiving through lines 407 and 409, which schematically correspond to the common line 264 in FIG. 15, and from outputs 412 and 414, digital control signals OSCA and OSCB. Depending upon values given to these two control signals by the computer, the signal characteristics of the driving reference signal OSCOUT, as produced at the third output 286 provided on the reference signals generator 254, can be selected, as will be later explained in more detail. The apparatus further comprises an oscillator output circuit section 488 receiving the driving reference signal from the output 286 at a first input 490 thereof, and receiving at a second input 491 thereof a digital control signal OSCCAL2 produced by the inverter 492 which is fed through a line 493 by an initial digital control signal $\overline{\text{OSCCAL2}}$ produced by the CPU bus output 358. The oscillator output circuit section 488 is further provided with a third input 494 receiving through the line 265 a gain control signal GAIN+from an output 496 provided on the DC control circuit section 468, as will be later described with reference to FIG. 20. The oscillator circuit section 402 further comprises first and second pairs of outputs 418, 419 and 420, 421 respectively producing pairs of square wave clock signals CLKSIN, $\overline{\text{CLKSIN}}$ and CLKCOS, $\overline{\text{CLKCOS}}$, as will be later explained with reference to FIG. 18, which square wave clock signals are respectively sent to gates inputs 432, 434, 436 and 438 of a variable attenuator circuit generally designated at numeral 254, which comprises four NOR gates 440, 442, 444 and 446 having gate inputs 448, 450, 452 and 454 being coupled to a supply voltage VTT 456 through a resistor 458, which supply voltage is produced with the power supply circuit as shown in FIG. 17B. In-phase and complementary 180° phased reference signals are respectively produced at outputs 460 and 462 provided on NOR gates 440 and 442, which reference signals have gain being varied through the diode based circuit 464 coupled to an ECL termination circuit 465, which circuit 464 being fed through the line 467 by a control signal GAINSIN produced at an output 466 of the DC control circuit section 468 provided on the control unit of the computer, which will be described with reference to FIG. 20. Resulting in-phase and 180° phased reference signals are respectively produced at a first pair of outputs 478 and 479, which corresponds to the first output 256 of the reference signals generator 254 as shown in FIG. 15, and then sent to a pair of inputs 483 and 484 provided on the first (SIN) synchronous detection circuit section 396, which pair of inputs corresponds to the input 250 as shown in FIG. 15. Similarly, quadrature phased and complementary 270° phased signals are respectively produced at outputs 470 and 472 provided on NOR gates 444 and 446, which reference signal have respective gain being varied through the diode based circuit 474 coupled to an ECL termination circuit 465, which circuit 474 being fed through the line 469 by a control signal GAINCOS produced at an output 476 of the DC control circuit section 468. It is pointed out that the lines 467 and 469 are schematically represented as the common line 262 in FIG. 15. Resulting quadrature phased and 270° phased reference signals are respectively produced at a second pair of outputs 480 and 481, which corresponds to the second output 258 of the reference signals generator 254 as shown in FIG. 15, and then sent to a pair of inputs 485 and 486 provided on the second quadrature phased (COS) synchronous detection circuit section 398, which pair of inputs corresponds to the input 252 as shown in FIG. 15. The first (SIN) synchronous detection circuit and second quadrature phased (COS) synchronous detection circuit sections are respectively fed through inputs 498 and 500 and the lines 282 and 284 by controls signals OFFSIN and OFFCOS respectively produced at outputs 497 and 499 provided on the DC Control circuit section 468, for enabling the computer to apply an offset compensation according to the calibration step as earlier mentioned. The DC control circuit section 468 is further provided with a series of four inputs 502, 504, 506 and 508 for respectively receiving from corresponding outputs 512, 514, 516 and 518 provided on the CPU bus 356, digital control signals $\overline{\text{LD}}$, DACCLOCK, SDI and $\overline{\text{RST}}$, as will be later described with reference to FIG. 20.

Figure 18:
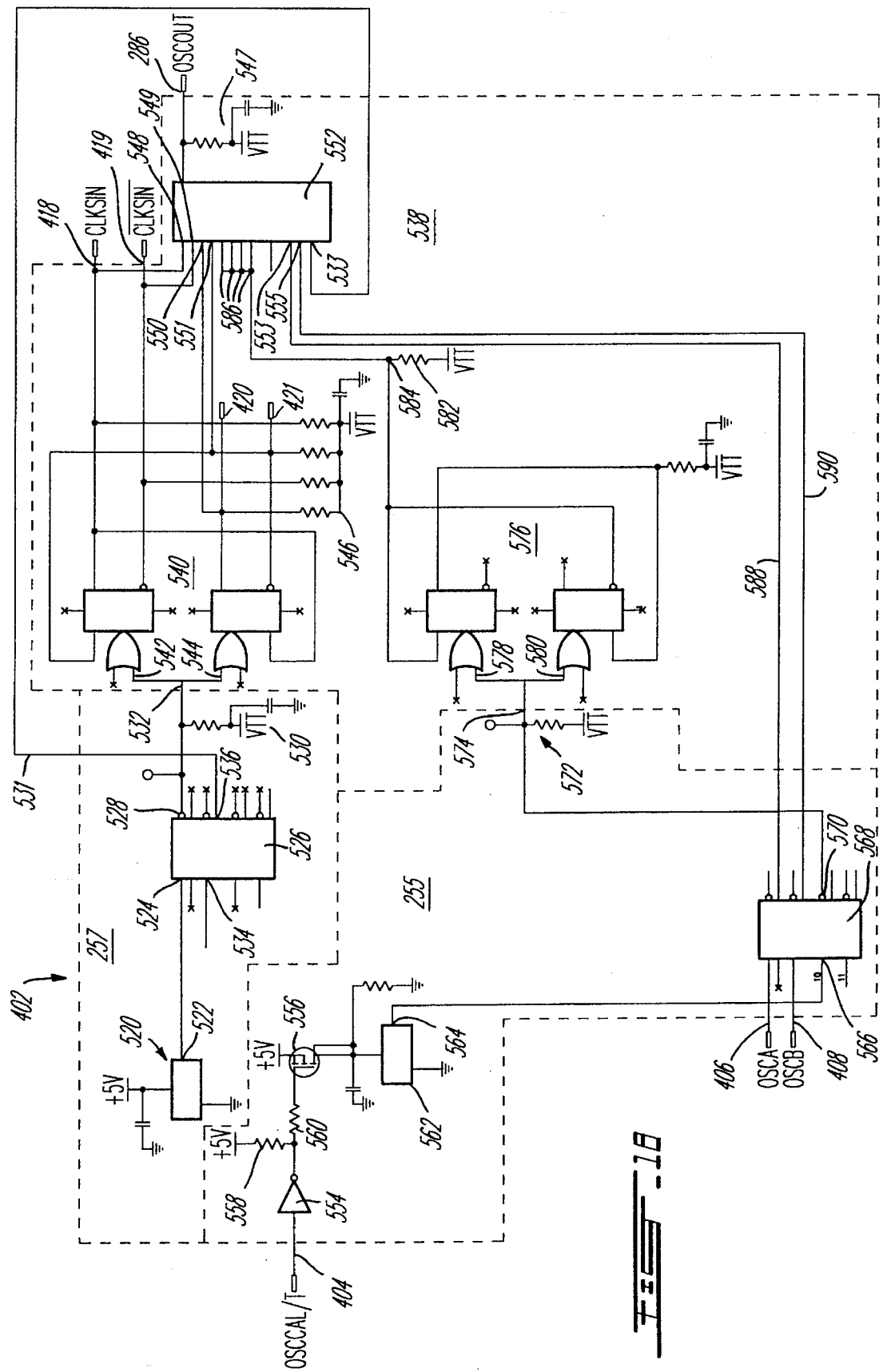
FIG. 18, is an electronic circuit diagram of the oscillators section of the circuit as shown in FIG. 17A.

Turning now to FIG. 18, the oscillator circuit section 402 comprises a main reference oscillator 257 having a crystal oscillator circuit 520 for producing at an output 522 thereof a high frequency TTL signal having a proposed frequency of 48 MHz, which is chosen to be a proper multiple of the desired ultrasonic operation frequency of 12 Mz, as will be hereunder explained. This TTL signal is then fed to an input 524 of a TTL/ECl connector 526 for obtaining at an output 528 thereof an high frequency ECL signal which directed following an ECL termination 530 toward an output 532 of the main reference oscillator 257. The TTL connector 526 receives at an input 534 from the corresponding output of the CPU bus, the OSCCAL/T control digital TTL signal for obtaining at an output 536 thereof a corresponding OSCCAL control digital ECL signal, whose function will be hereunder explained in detail. The main reference oscillator output 532 is connected to a square wave generator circuit 538 provided on the oscillator circuit section 402, which comprises at its input end a first dual type master/slave flip-flop circuit, generally designated at numeral 540, having both inputs 542 and 544 fed by the 48 MHz ECL signal as produced by the main reference oscillator 257. Following an ECL termination 546, pairs of 12 MHz square wave clock signals CLKSIN, $\overline{\text{CLKSIN}}$ and CLKCOS, $\overline{\text{CLKCOS}}$ are produced respectively at the outputs 418 to 421 of the oscillator circuit section 402. The square wave clock signals CLKSIN, $\overline{\text{CLKSIN}}$ and CLKCOS, $\overline{\text{CLKCOS}}$ are also directed respectively toward inputs 548 to 551 of a multiplexer switch 552, whose function will be hereunder explained. The oscillator circuit section 402 further comprises a calibration reference oscillator 255 also receiving at the input 404 from the corresponding output of the CPU bus, the OSCCAL/T control digital TTL signal, which is fed to an on/off switching circuit comprised of an inverter 554 coupled to a transistor 556 through resistors 558 and 560. Whenever the OSCCAL/T control digital TTL is given a value representing a "on" command, a crystal oscillator circuit 562 is accordingly activated for producing at an output 564 thereof a high frequency TTL asynchronous calibration signal having a proposed frequency distant from the 48 MHz of the main reference oscillator 257 by a few hundred hertz, as well known in the art of circuit calibration. This TTL asynchronous calibration signal is then fed to an input 566 of a TTL/ECl connector 568 for obtaining at an output 570 thereof a high frequency ECL asynchronous calibration signal which is directed following an ECL termination 572 toward an output 574 of the calibration reference oscillator 255. The TTL/ECl connector 568 also receives respectively through inputs the 406 and 408 provided on the oscillator circuit section 402, the digital control signals OSCA and OSCB, which are sent, following TTC to ECL conversion through lines 588 and 590, to inputs 553 and 555 provided on multiplexer switch 552 for activation thereof, as hereunder explained. The calibration reference oscillator output 574 connected to the square wave generator circuit 538 provided on the oscillator circuit section 402, which further comprises at its input end a second dual type master/slave flip-flop circuit, generally designated at numeral 576, having both inputs 578 and 580 fed by the high frequency ECL calibration signal as produced by the calibration reference oscillator 255. Following an ECL termination 582, a square wave calibration signal having a frequency near 12 MHz is produced at an output 584, which signal is sent to inputs 586 of the multiplexer switch 552. The OSCCAL control digital ECL signal as produced at the output 536 of the TTL/ECL connector 526 is sent through a line 531 to an input 533 provided on the multiplexer switch 552. Depending upon values given by the computer to the digital control signals OSCCAL, OSCA and OSCB, the signal characteristics of the driving reference signal OSCOUT as produced at the third output 286 provided on the reference signals generator 254 can be selected. In the calibration mode, an enable OSCCAL signal causes the multiplexer switch 532 to produce at the output 286 following an ECL termination 547 a reference calibration signal OSCOUT corresponding to the high frequency ECL asynchronous calibration signal entering at multiplexer inputs 586, while a disable OSCCAL signal either in a calibration or ultrasonic image acquisition mode causes the multiplexer switch 532 to produce at its output 286 a reference calibration signal or driving reference signal OSCOUT corresponding either to square wave clock signals CLKSIN (in-phase), $\overline{\text{CLKSIN}}$ (180° phased) CLKCOS (quadrature phased) or $\overline{\text{CLKCOS}}$ (270° phased), depending upon values given by the computer to the digital control signals OSCA and OSCB. For practical purposes, in an image acquisition mode, anyone of these square wave clock signals can be selected for producing the driving reference signal OSCOUT.

Figure 19:
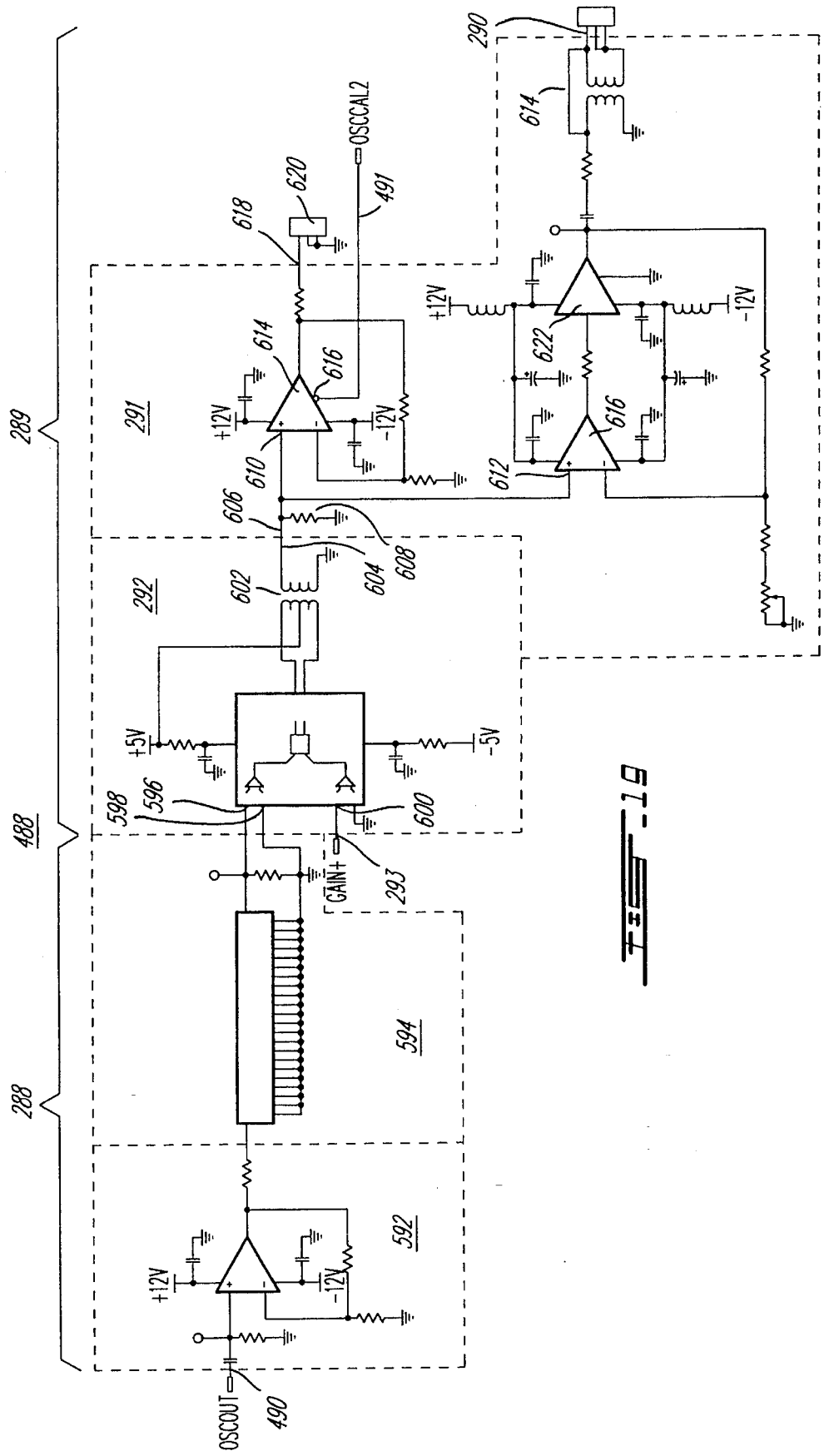
FIG. 19 is an electronic circuit diagram of the oscillator output section of the circuit as shown in FIG. 17A.
Figure 20:
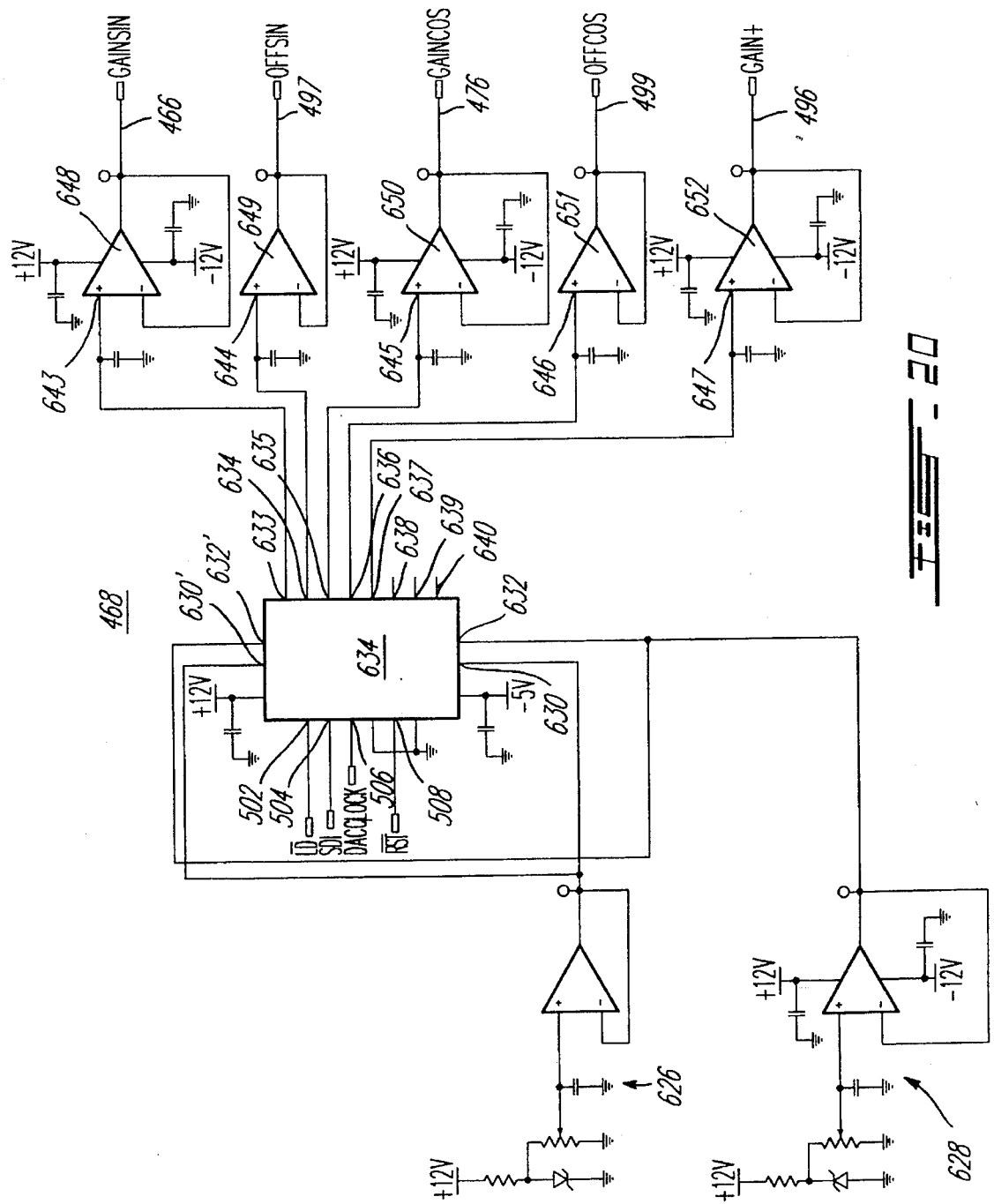
FIG. 20 is an electronic circuit diagram of the DC controls section of the circuit as shown in FIG. 17, which DC controls section is part of the computer provided in the present invention.

Turning now to FIG. 19, there is shown the oscillator output circuit section 488 of the main circuit as shown in FIG. 17A. The amplifier section 289 is coupled to the third reference output 286 provided on the reference signal generator 254 as shown in FIG. 17A, through a preamplifying and bandpass filtering section 288 comprised of a preamplifier stage 592 in series with a bandpass filter 594. The preamplifier stage 592 receives at an input 490 provided on the oscillator output circuit section 488, either the reference calibration signal or the driving reference signal OSCOUT, for feeding to the bandpass filter 594 a preamplified reference calibration signal or preamplified driving reference signal to the bandpass filter 594, which has a bandwidth of 1 MHz being centered at 12 MHz in the proposed circuit embodiment. The resulting filtered signal, which is essentially sinusoidal, is directed to main and complementary input ports 596 and 598 of a first input provided on the multiplier 292 comprised in the amplifier circuit section 289, which multiplier 292 receives at a main input port 600 of its second input 293, the gain control signal GAIN+ coming from the output 496 provided on the DC Control circuit section 468 as shown in FIG. 17A and 20. A resulting signal, whose amplitude has been set depending upon the value given to the gain control signal GAIN+ by the computer, is produced at an unbalanced output of a transformer 602, which resulting signal is fed, through a common input line 606 and resistor termination 608, to both inputs 610 and 612 of calibration signal input circuit 352 receiving a calibration signal provided in the power amplifier 291. The differential amplifier 614 receives at an input 616 provided thereon and from the input 491 provided on the oscillator output circuit section 488, the digital control signal OSCCAL2 derived form the initial digital control signal $\overline{\text{OSCCAL2}}$ produced by the CPU bus output 358, as shown in FIG. 17A. Simultaneously to a calibration mode activation of the switch 350 provided on the input amplifier 248 as shown in FIG. 17A, the differential amplifier 614 is activated whenever the digital control signal OSCCAL2 is given an activating value by the computer, thereby switching the power amplifier 291 to a calibration mode, to produce at a calibration output 618 and connector 620 a calibration signal which is sent to connector 354 of the calibration signal input circuit 352 as shown in FIG. 17A. The differential amplifier 616, as part of a preamplifyng stage, is coupled to a third differential amplifier 622 used as part of a power amplifier stage. Following an isolation transformer 624, an amplified driving reference signal is produced at the output 290 of the power amplifier 291 provided on the amplifier section 289, which signal is directed to the ultrasonic emitter transducer 184 as shown in FIG. 15.

Referring now to FIG. 20, the DC controls section 468 of the circuit as shown in FIG. 17, which DC controls section is part of the computer provided in the present invention, will be described. Voltage supply circuits 626 and 628 respectively provide low and high reference voltage signals to inputs 630, 630' and 632, 632' provided on a digital to analog converter 634 having outputs 633 to 640. The digital to analog converter 634 further receives at the inputs 502, 504, 506 and 508 digital control signals $\overline{\text{LD}}$, SDI, DAC-CLOCK and $\overline{\text{RST}}$ from corresponding outputs 512, 516, 514 and 518 provided on the CPU bus 356 as shown in FIG. 17A. The operation of the digital to analog converter 634 ca be generally described as follows. A clock signal DAC-CLOCK is continuously provided to synchronize the operation of the digital to analog converter 634. The computer initially sends an inverted reset digital signal $\overline{\text{RST}}$ to the digital to analog converter 634 so as to clear all data previously contained therein. The reset signal is then followed by a serial data input digital signal SDI, which basically comprises control bits identifying, for following data, an output address associated with one of the digital to analog outputs 633 to 638. The digital data is then converted to a corresponding analog control signal which is produced at one of the outputs 633 to 640 according to the address contained in the control bits. In the present circuit embodiment, only outputs 633 to 637 are required, which are respectively coupled to inputs 643 to 647 of amplifier buffers 648 to 65, which are essentially provided for signals impedance matching. Depending upon the data contained in the serial data input digital signal SDI, one of the control signals GAINSIN, GAINCOS, OFFSIN, OFFCOS or GAIN+ is produced at a corresponding one of outputs 466, 497, 476, 499, and 496 of the DC controls circuit section 468. Prior to send any following signal data, a load indicating digital control signal $\overline{\text{LD}}$ is sent by the computer to the input 502 of the analog to digital converter 634, for indicating thereto an end of data.

Referring now to FIG. 21, the first (SIN) synchronous detection circuit section 396 as shown in FIG. 17A will be described. The amplified electrical signals as produced at the output 394 provided on the input amplifier 248 as shown in FIG. 17A, are sent through the input 244 of the first (SIN) detection circuit section 396 to the main input port 654 of a first input provided on a multiplier 656 as part of a multiplier section 240. A precalibration offset reference signal is produced by a first variable resistor circuit 658 and directed to the complementary input port 660 of the multiplier first input. The in-phase and 180° phased reference signals as respectively produced at outputs 478 and 479 of the reference signals generator 254 as shown in FIG. 17A, are sent through inputs 483 and 484 provided on the first (SIN) synchronous detection circuit section 396, are coupled to main and complementary inputs ports 665 and 667 of a second input provided on the multiplier 656, respectively through a first high-pass filter 662 connected to a resistor termination 664 and a second high-pass filter 666 connected to a second variable resistor circuit 668. As extensively explained in a previous part of the present specification regarding synchronous detection technique, the first signal vector component signals corresponding to electrical signals coming from the ultrasonic detectors array 186 as shown in FIG. 15, are produced at outputs 670 and 672 provided on the multiplier 656, in the form of pairs of complementary signals directed to respective main inputs 674 and 676 of first and second amplifiers 678 and 680, which amplifiers being part of the intermediate amplifier section 267 further comprising a third amplifier 682 having a main input 688 coupled to an output 679 of the amplifier 678 through a resistor 684 connected to a resistor termination 686. The third amplifier 682 has a complementary input 690 coupled to an output 692 of the second amplifier 680 through a first resistor 694, and further has an output 696 being coupled to the output 694 through the first resistor 694 and a second resistor 698. The first signal vector component signals amplified at a proper level are fed through the intermediary amplifier section output 696 and through an ECL termination 700 to a lowpass filter 710 as part of the lowpass filter circuit section 270 having a cutoff frequency of 5 MHz in the proposed circuit embodiment. After filtering, the first signal vector component signals are fed to a main input 714 of a differential amplifier 716 as part of the output amplifier section 274, which further has a complementary input 718 and an output 717 being coupled through a resistors circuit 716 to the control signal OFFSIN produced at the output 497 provided on the DC control circuit section 468 as shown in FIGS. 17A and 20, for enabling the computer to apply an offset compensation according to the calibration step as earlier discussed, by varying the gain of the amplifier 716. A variable resistor 718 is provided on the resistors circuit 716 for pre-calibration purposes. Following an output resistor 720, the first signal vector component signals corresponding to the electrical signals coming from ultrasonic detectors 192 are produced at the amplifier section output 278, and directed through a connector 719 to the first analog to digital converter, as shown in FIG. 15.

Referring now to FIG. 22, the second quadrature phased (COS) synchronous detection circuit section 398 as shown in FIG. 17A will be described. It is pointed out that this circuit is identical to the first (SIN) synchronous detection circuit section 396, and therefore, hereabove description of the first (SIN) circuit section applies to the second quadrature phased circuit section 398, except for the nature of input and output signals. The amplified electrical signals as produced at the output 394 provided on the input amplifier 248 as shown in FIG. 17A, are sent through the input 246 of the second quadrature phased (COS) detection circuit section 398 to the main input port 724 of a first input provided on a multiplier 726 as part of a multiplier section 242. A precalibration offset reference signal is produced by a first variable resistor circuit 722 and directed to the complementary input port 730 of the multiplier first input. The quadrature phased and 270° phased reference signals as respectively produced at outputs 480 and 481 of the reference signals generator 254 as shown in FIG. 17A, are sent through inputs 485 and 486 provided on the second quadrature phased (COS) synchronous detection circuit section 398, to main and complementary inputs ports 732 and 734 of a second input provided on the multiplier 726, respectively through a first high-pass filter 736 connected to a resistor termination 738 and a second high-pass filter 740 connected to a second variable resistor circuit 742. As extensively explained in a previous part of the present specification regarding synchronous detection technique, the second signal vector component signals corresponding to electrical signals coming from the ultrasonic detectors array 186 as shown in FIG. 15, are produced at outputs 746 and 748 provided on the multiplier 726, in the form of pairs of complementary signals directed to respective main inputs 750 and 752 of first and second amplifiers 754 and 756, which amplifiers being part of the intermediate amplifier section 269, which is essentially identical to the intermediate amplifier section 267 of the first (SIN) synchronous detection circuit section 396. The second signal vector component signals amplified at a proper level are fed through the intermediary amplifier section output 758 and through an ECL termination 760 to a lowpass filter 762 as part of the lowpass filter circuit section 272 having a cutoff frequency of 5 MHz in the proposed circuit embodiment. After filtering, the second signal vector component signals are fed to a main input 764 of a differential amplifier 766 as part of the output amplifier section 276, which further has a complementary input 768 and an output 770 being coupled through a resistors circuit 772 to the control signal OFFCOS produced at the output 499 provided on the DC Control circuit section 468 as shown in FIGS. 17A and 20, for enabling the computer to apply an offset compensation according to the calibration step as earlier discussed, by varying the gain of the amplifier 766. A variable resistor 774 is provided on the resistors circuit 772 for pre-calibration purposes. Following an output resistor 776, the first signal vector component signals corresponding to the electrical signals coming from ultrasonic detectors 192 are produced at the amplifier section output 280, and directed through a connector 778 to the first analog to digital converter, as shown in FIG. 15.

Referring now to FIGS. 23 to 26, a fish fillet ultrasonic imaging apparatus embodying the present invention will be described. Turning to FIG. 23, 24 and 26, the fish fillet ultrasonic imaging apparatus generally designated at numeral 780 comprises a frame, generally designated at numeral 782, supporting through a connecting member 761 provided with a pivot 763 as shown in FIG. 26, a pivoting holder comprised of a pivoting square 781 adjustably connected to a mounting block 783 provided with an adjustment U-shaped square 779. To the block 783 is connected an ultrasonic unit comprised of an electronic enclosure 784 having a cover 785, an ultrasonic detectors array head 858, and an ultrasonic emitter head 857, as shown in FIG. 25. Relative position adjustment of the ultrasonic emitter head 857 and ultrasonic detectors array head 858 is provided through a sliding emitter support member 767 having a lower end being secured to the ultrasonic emitter head 857, as shown in FIG. 25, and an upper end secured to a first protruding threaded rod ended with a first adjustment button 885, which threaded rod extending through a first bore provided in the mounting block 783, as shown in FIG. 26. Position adjustment of the ultrasonic emitter head and ultrasonic detectors array head relative to the pivoting square 781 is provided through rotation of a second adjustment button provided at an upper end of a second threaded rod extending through a second threaded bore provided in the mounting block 783 and abutting against upon an upper surface provided on the pivoting square 781, as shown in FIG. 26. Following position adjustment operations, the ultrasonic unit head and ultrasonic detectors array head are maintained in a stationary position within the main tank 788. The apparatus further comprises a fish fillet transport unit generally designated at numeral 786, and a main tank 788 secured to the frame 782 by attaching members 793, which main tank is filled through an inlet 753 provided thereon with a non-toxic liquid, such as water, to serve as a coupling means for the ultrasonic waves traversing a detection zone 790 which can be seen through a porthole 792 provided in a front wall 794 of the main tank 786, as shown in FIG. 23. At the bottom of the main tank 786 is connected a drain outlet 789 provided with a valve 791. The fish fillet transport unit 786 has an input end 796 bordered by respective first ends of opposed front and rear plates 798 and 798' provided on the fish fillet transport unit 786 and mounted on the frame 782. The rear plate 798' is provided with a bore 800 trough which a shaft end 802 of a driving motor reducer 813 protrudes, as respectively shown in FIGS. 23 an 24. A transmission chain or belt 804 coupled to the shaft end 802 drives respective driving shafts 771, 773, 775 and 777 of chain conveyers 803, 805, 807 and 809 provided in the transport unit 786, as shown in FIG. 24, whose function will be explained in more detail with reference to FIG. 25. The conveyer 803 is cleaned either continuously or periodically by water jets produced by a pipe 795 connected to a plurality of nozzles 797 provided thereon, as shown in FIG. 24. The water flow is controlled through a solenoid valve 799 connected to a fresh water supply means (not shown). A pair of input opposed guide plates 806 are provided to ensure proper alignment of an incoming fish fillet 811 to be inspected which is directed to the inspection zone 790. A driving motor reducer support member 808 being generally U-shaped has a front end being secured to the front plate 798 by bolt and nut assemblies 812, as shown in FIG. 23. The lower portion of the support member 808 is coupled to the frame 782 by a fluid absorber 810 through bolt and nut hinge assemblies 812 and 815, as shown in FIGS. 23 and 26. The fish fillet transport unit 786 has an output end 814 bordered by respective second ends of opposed front and rear plates 798 and 798' provided on the fish fillet transport unit 786 and mounted on the frame 782. A filtration tank 816 mounted on a holding base 817 is positioned next to the frame 782 at the output end 814 of the fish fillet transport unit 786. Alternately, the filtration tank can be directly mounted on the frame 782. The filtration tank 816 is in fluid communication with an outlet 787 provided on the main tank 788 to receive the water flowing out thereof, as shown in FIG. 24. The filtration tank is provided with a filter 818, such as a mesh, for collecting particles and the like in suspension in the water, an overflow outlet 819 and a rear outlet 820 connected to an output pipe 828 as shown in FIG. 24, through which filtered water is flowing toward a pumping unit comprising a pump 822 having an inlet 824 coupled to the pipe 828 and an outlet 826 coupled through an outlet pipe 830 coupled to a manifold inlet block 834 of a manifold generally designated at numeral 832 in FIG. 24. The pump 822 is driven by an electric motor 823, or by any other suitable driving power supply means, which is mounted on the frame 782 with attaching members 831 provided with an electrical junction box 827 and a capacitance block 829. The manifold 832 is provided with an outlets block 836 having a plurality of outlets 838 connected to a plurality of water feeding pipes 840 through sanitary couplings 842. The water flow through the water feeding pipes 840 can be controlled by a plurality of valves 844 mounted on a valve support member 846 secured at both ends to the frame 782 by attaching plates 847 and 847'. As better shown in FIG. 26, each of the manual valves 844 comprises an handle 843 activating a pushing rod 845 whenever a downward pressure is applied on the handle 843, locally squeezing the corresponding water feeding pipe 840 between the rod end and the bottom portion 841 of the valve support member 846, so as to adjust the water flow therethrough, the water feeding pipes being preferably made of resilient material such as rubber. Obviously, any other equivalent sanitary valve device, such as rotating handle valve, with any other proper water feeding pipe types, such as rigid plastic pipes, can be used. The water feeding pipes 840 are coupled to respective inlets 848 provided on the main tank 788 through respective sanitary couplings 850, which inlets are connected to respective first ends of water feeding conduits tranversely extending through the main tank 788 and front and rear plates 798 and 798', and abutting at second ends thereof against inner surface of the front wall 794 of the main tank 788. The function of the water feeding conduits will be later explained in more detail with reference to FIG. 25. To insure proper sealing at first and second conduit ends, the main tank 788 is laterally compressed by two sets of clamp assemblies 851 having pushing ends 853 respectively in abutment with front wall 794 and rear wall (not shown) of the main tank 788. Turning now to FIG. 25, the mode of operation and further elements of the fish fillet transport unit 786 will be described. The main purpose of the fish fillet transport unit 786 consists in immersing a fish fillet to be inspected in the water contained in the main tank 788 toward the detecting zone 790 and then bringing the inspected fish fillet out of the water toward the output end 814 provided on the fish fillet transport unit 786. For an ultrasonic unit using a scanning linear detectors array as earlier described, the transport unit further has the purpose of creating a scanning relative movement between a fish fillet 855 to be inspected, which is surrounded by a mass of water, and an ultrasonic unit comprised of an ultrasonic emitter head 857 and a scanning ultrasonic detectors array head 858 comprised in an electronic unit as generally designated at numeral 859. The fish fillet transport unit 786 comprises a first conveyer unit mounted at its first end 796, which comprises a feeding conveyer 803 adapted to receive a fish fillet. 811 to be inspected entering the first conveyer unit input end 796, for carrying the fish fillet 811 to an output end 860 provided on the feeding conveyer 803 over the main tank 788 and toward the water mass 862 filling the main tank 788. The feeding conveyer 803 has a driving shaft 771 provided with a pair of gears 864 secured thereon at proximity of both ends thereof for driving a conveyer chain 866 provided on the feeding conveyer 803. The feeding conveyer 803 further has driven shafts 868 and 870 provided with respective pairs of gears 872 and 874 secured thereon at proximity of both ends thereof. The ends of driving shaft 771 and driven shafts 868 and 870 are mounted for rotation thereof through corresponding pairs of circular recesses or holes 801 provided on front and rear plates 798 and 798', as shown in FIG. 23. The first conveyer unit further comprises an immersing conveyer 805 mounted in the main tank 788 along the guide plates 806 for receiving the fish fillet 811 from the feeding conveyer 803. The immersing conveyer 805 is preferably totally immersed in the water mass 862 so as to prevent air bubbles formation which may otherwise occurs. When carried within the detecting zone 790, such air bubbles may cause imaging interferences. The immersing conveyer 805 is provided for immersing a fish fillet 876 in the water mass 862 and for carrying the fish fillet 876 toward an output end 878 of the first conveyer unit. The immersing conveyer 805 has a driving shaft 773 provided with a pair of gears 884 secured thereon at proximity of both ends thereof for driving a conveyer chain 886 provided on the immersing conveyer 805. The immersing conveyer 805 further has a driven shaft 888 provided with a pair of gears 890 secured thereon at proximity of both ends thereof. The ends of the driving shaft 773 and driven shaft 888 are mounted for rotation thereof through corresponding pairs of circular recesses or holes (not shown) provided on front and rear plates 798 and 798'. The fish fillet transport unit 786 further comprises a second conveyer unit consisting in a conveyer 807 mounted in the main tank 788 and substantially immersed in the water mass 862, and having a first end 880 extending over the first conveyer unit output end 878 and an output end 882. The conveyer 807 has a driving shaft 775 provided with a pair of gears 701 secured thereon at proximity of both ends thereof for driving a conveyer chain 703 provided on the conveyer 807. The conveyer 807 further has driven shafts 705 and 707 provided with respective pairs of gears 709 and 711 secured thereon at proximity of both ends thereof. The ends of the driving shaft 775 and driven shafts 705 and 707 are mounted for rotation thereof through corresponding pairs of circular recesses or holes (not shown) provided on the front and rear plates 798 and 798'. The main tank 788 is provided with a plurality of first water feeding conduits 892 tranversely extending through the main tank 788 and openings 900 provided in front and rear plates 798 and 798' and abutting at second ends thereof against inner surface of the front wall 794 of the main tank 788, which first water feeding conduits 892 are disposed from the first conveyer unit output end 878 and under the second conveyer 807. The first water feeding conduits 892 have first nozzles 894 projecting series of water jets toward the fish fillet 876 to move thereof from the vicinity of the first conveyer unit output end 878 to an underside surface 896 of the second conveyer 807. The main tank 788 is further provided with at least one second water feeding conduit 898 tranversely extending therethrough under the second conveyer output end 882, and having at least one second nozzle 902 projecting series of water jets toward the fish fillet 855 to propel thereof from the vicinity of the second conveyer output end 882 toward an upper guide plate 901 in the detecting zone 790, and through an output conduit 903 formed by upper and lower guide walls 905 and 907 and opposed side walls 909, which upper guide plate 901 is mounted under the scanning ultrasonic detectors array head 858. The fish fillet transport unit 786 further comprises a third conveyer unit consisting in a conveyer 809 mounted at the second end 814 of the fish fillet transport unit 786, and having an input end 904 for receiving an inspected fish fillet 906 as it comes out of the output conduit 903, to bring the inspected fish fillet 906 out of the water mass 862 toward the transport unit output 814. The conveyer 809 has a driving shaft 775 provided with a pair of gears 908 secured thereon at proximity of both ends thereof for driving a conveyer chain 910 provided on the conveyer 809. The conveyer 809 further has driven shafts 910, 912 and 914 provided with respective pairs of gears 916, 918 and 920 secured thereon at proximity of both ends thereof. The ends of the driving shaft 775 and driven shafts 912, 913 and 914 are mounted for rotation thereof through corresponding pairs of circular recesses or holes 922 provided on front and rear plates 798 and 798', as shown in FIG. 23. It is pointed out that the conveyer chains 866, 886, 703 and 910 are preferably provided at their external periphery with gripping means such as series of teeth (not shown) to avoid slipping of the fish fillet thereon.

It is within the ambit of the present invention to cover any obvious modifications in the proposed apparatus and method, and any applications thereof, provided such modifications and applications fall within the scope of the appended claims.

We claim:

1. An ultrasonic transmission imaging apparatus comprising:

ultrasonic emitter means for producing substantially continuous coherent ultrasonic waves toward an object to be inspected positioned in a detecting zone;

ultrasonic coupling means in contact with said object on opposed sides thereof, for providing transmission of said ultrasonic waves thereto, transfer of said ultrasonic waves therethrough, and transmission of object traversing ultrasonic waves out of said object;

scanning ultrasonic detectors array means comprising a plurality of ultrasonic detectors adapted to receive said object traversing ultrasonic waves for producing a plurality of successive series of electrical signals coming from said ultrasonic detectors, said electrical signals characterizing transmission of said ultrasonic waves through said object;

means for creating a scanning relative movement between said object to be inspected and said ultrasonic emitter means and scanning ultrasonic detectors array means, whereby said series of electrical signals respectively characterizes transmission of said ultrasonic waves through said object in a plurality of transmission planes substantially defined by said scanning ultrasonic detectors array means and a direction perpendicular thereto and to said emitter means as said object to be inspected is being displaced relative to said ultrasonic emitter means and scanning ultrasonic detectors array means, said series of electrical signals being respectively associated with a series of image elements;

dynamic focusing means for producing focused image element data from said series of electrical signals and associated with each one of said ultrasonic detectors, said focusing means phase shifting each one of said series of electrical signals in accordance with each location within said object to be imaged in focus for producing a composite image element.

2. An ultrasonic transmission imaging apparatus as claimed in claim 1, wherein said dynamic focusing means comprise:

signal vector components detector means adapted to receive said electrical signals, said signal vector components detector means detecting signal vector components for each of said electrical signals, to produce pairs of first and second signal vector component signals corresponding to said electrical signals;

computer means for controlling said apparatus and adapted to receive said pairs of first and second signal vector component signals, said computer having memory means for storing said pairs of first and second signal vector component signals and for storing focusing function data establishing, for each image element comprised in a focusing aperture comprising a plurality of juxtaposed image elements of said series of image elements, a phase displacement value relative to a reference phase value associated with a focal line passing through a focus point and a center of said aperture, said computer means using said focusing function data to produce corresponding pairs of first and second resulting signal vector component signals forming a focused image representation of said object traversing ultrasonic waves.

3. An ultrasonic transmission imaging apparatus as claimed in claim 2, wherein said signal vector component detector means include analog-to-digital converter means adapted to receive said pairs of first and second signal vector component signals for producing corresponding pairs of first and second signal vector component digital signals.

4. An ultrasonic transmission imaging apparatus as claimed in claim 3, wherein said computer means resulting amplitude signals corresponding to said pairs of first and second resulting signal vector component digital signals, said apparatus further comprising display means adapted to receive said resulting amplitude signals to produce a visual display of said focused digital image representation of said object traversing ultrasonic waves.

5. An ultrasonic transmission imaging apparatus as claimed in claim 3, further comprising multiplexer means coupling said ultrasonic detector means with said signal vector components detector means, said computer means being connected to said multiplexer means for control thereof, said multiplexer means having a plurality of inputs respectively fed by each one of said electrical signals, said multiplexer means further having output through which each one of said electrical signals is sequentially transferred to said signal vector components detector means.

6. An ultrasonic transmission imaging apparatus as claimed in claim 5, wherein said multiplexer means is provided with preamplifier means for amplifying each one of said electrical signals prior transferring thereof to said signal vector components detector means.

7. An ultrasonic transmission imaging apparatus as claimed in claim 5, wherein said signal vector components detector means is a synchronous detector circuit comprising first and second multipliers having respective signal inputs coupled to said multiplexer means output and having respective reference inputs means, said synchronous detector circuit further comprising a reference signals generator means having first and second outputs means respectively connected to said respective reference inputs means provided on said first and second multipliers to respectively sent thereto a first reference signal and a second reference signal in phase quadrature with said first reference signal at a common operating frequency, said computer means being connected to said reference signals generator for control thereof, said first and second multiplier means further having respective outputs for respectively producing a first signal comprising a primary signal vector component and a second signal comprising a secondary quadrature phased signal vector component, said synchronous detector circuit further comprising first and second lowpass filters respectively coupled to said multiplier outputs and in series with respective first and second output amplifiers for producing at first and second outputs thereof said pairs of first and second signal vector component signals corresponding to said electrical signals, said computer means being connected to said output amplifiers for control thereof, said apparatus further comprising amplifier means coupled to a third output means provided on said reference signals generator means for receiving a driving reference signal to produce at an output thereof an amplified driving reference signal at said common operating frequency, said computer means being connected to said amplifier means for control thereof, said ultrasonic emitter means receiving said amplified driving reference signal at an input thereof for producing said continuous coherent ultrasonic waves.

8. An ultrasonic transmission imaging apparatus as claimed in claim 7, wherein said synchronous detector circuit further comprises an input amplifier coupling said first and second multipliers signal inputs with said multiplexer means output, said computer means being connected to said input amplifier means for control thereof, said input amplifier amplifying each one of said electrical signals prior sending thereof to said first and second multipliers signal inputs, said synchronous detector circuit further comprising first and second intermediate amplifier means for coupling said first and second lowpass filters respectively to said multiplier outputs.

9. An ultrasonic transmission imaging apparatus as claimed in claim 7, wherein said first and second reference signals are square wave reference signals, said apparatus further comprising a preamplifier in series with a bandpass filter for coupling said amplifier means to said third output means provided on said reference signals generator means.

10. An ultrasonic transmission imaging apparatus as claimed in claim 3, wherein said computer means detects the presence of said object to be inspected apparently moving in said detecting zone prior producing said corresponding pairs of first and second resulting signal vector component digital signals forming said focused digital image representation of said object traversing ultrasonic waves.

11. An ultrasonic transmission imaging apparatus as claimed in claim 10, wherein said computer means detects the presence of said apparently moving object to be inspected in said detecting zone by deriving a mean intensity value for consecutive ones of said pairs of first and second signal vector component digital signals corresponding with at least one of said series of electrical signals coming from said ultrasonic detectors and by comparing said mean intensity value with a predetermined presence threshold value.

12. An ultrasonic transmission imaging apparatus as claimed in claim 3, wherein said first and second signal vector component digital signals are respectively associated with a real component value and an imaginary component value, said computer means multiplying said component values of said first and second signal vector component digital signals with respective real component value and imaginary component value of a correction parameter prior using said focusing function data to produce a corrected signal vector, said correction parameter and said corrected signal vector being defined according to the following mathematical expressions:

$$A_k = AI_k + iAQ_k = \frac{T}{M_k} \quad (4)$$

$$M_k = \frac{i}{j} \sum_{j=0}^{J-1} S_{j,k} \quad (5)$$

$$S_{j,k} = SI_{j,k} + iSQ_{j,k} \quad (6)$$

$$C_{k,l} = A_k B_{k,l} = CI_{k,l} + iCO_{k,l} \quad (7)$$

$$B_{k,l} = BI_{k,l} + iBQ_{k,l} \quad (8)$$

wherein k and l are primary coordinates according to first and second axis X and Y of a cartesian reference system for the ultrasonic detector array and associated image elements, with k=0,K−1 and l=0,L−1;

$A_k$ is the correction parameter associated with one of the image elements having coordinate k, this correction parameter compensating for detector sensibility variation among corresponding ones of the ultrasonic detectors;

$AI_k$ is the real component value of the correction parameter associated with one of the image elements having coordinate k;

$AQ_k$ is the imaginary component value of the correction parameter associated with one of the image elements having coordinate k;

T is a target parameter being characterized by a target uniform amplitude and phase values corresponding to a reference target image;

$M_k$ is a mean value of sample pairs of first and second signal vector component signals associated with one of the image elements having coordinate k, prior detecting the presence of an object apparently moving in the detecting zone;

J is a predetermined number of said sample pairs of first and second signal vector component signals;

$S_{j,k}$ is the signal vector of a sample j associated with one of said image elements having coordinate k;

$SI_{j,k}$ is a real component value associated with said first signal vector component digital signals and corresponds to the real component value of said signal vector of a sample j associated with one of said image elements having coordinate k;

$SQ_{j,k}$ is an imaginary component associated with said second signal vector component digital signals and corresponds to the imaginary component value of said signal vector of a sample j associated with one of said image elements having coordinate k;

$C_{k,l}$ is a corrected signal vector associated with one of said image elements having coordinates k and l;

$CI_{k,l}$ is a real component value associated with said first corrected signal vector component digital signals and corresponds to a real component value of said corrected signal vector associated with one of said image elements having coordinates k and l;

$CQ_{k,l}$ is an imaginary component value associated with said second corrected signal vector component digital signals and corresponds to an imaginary component value of said corrected signal vector associated with one of the image elements having coordinates k and l;

$B_{k,l}$ is the signal vector associated with one of said image elements having coordinates k and l;

$BI_{k,l}$ is a real component value associated with said first signal vector component digital signals and corresponds to the real component value of said signal vector associated with one of said image elements having coordinates k and l;

$BQ_{k,l}$ is an imaginary component value associated with said second signal vector component digital signals and corresponds to the imaginary component value of said signal vector associated with one of said image elements having coordinates k and l.

13. An ultrasonic transmission imaging apparatus as claimed in claim 12, wherein said computer means compares values of said correction parameter with a predetermined threshold value to detect corresponding unusable ones of said ultrasonic detectors, said computer means substitute for corresponding ones of said pairs of first and second signal vector component signals respective first and second signal vector component signals corresponding to proximate usable ones of said ultrasonic detectors.

14. An ultrasonic transmission imaging apparatus as claimed in claim 12, wherein said computer means applies a convolution technique to produce corresponding pairs of first and second resulting signal vector component digital signals forming said focused digital image representation of said object traversing ultrasonic waves according to the following mathematical expressions:

$$D_{k,l} = \sum_{m=-M}^{M} \sum_{n=-N}^{N} C_{k-m,l-n} L_{m,n} = DI_{k,l} + iDQ_{k,l} \quad (9)$$

$$C_{k-m,l-n} = A_{k-m} B_{k-m,l-n} \quad (10)$$

$$B_{k-m,l-n} = BI_{k-m,l-n} + iBQ_{k-m,l-n} \quad (11)$$

$$L_{m,n} = \frac{F_{m,n}}{L_{norm}} = LI_{m,n} + iLQ_{m,n} \quad (12)$$

$$F_{m,n} = FI_{m,n} + iFQ_{m,n} \quad (13)$$

$$L_{norm} = LI_{norm} + iLQ_{nor} \quad (14)$$

wherein:

m and n are secondary coordinates according to first and second axis X and Y of the cartesian reference system for said ultrasonic detector array and associated image elements, with m=−M,M and n=−N,N, the size of said focusing function data being equal to (2M+1)(2N+1);

$D_{k,l}$ is the resulting signal vector associated with one of said image elements having coordinates k and l;

$DI_{k,l}$ is a real component value of said first resulting signal vector component digital signals and corresponds to a real component value of said resulting signal vector associated with one of said image elements having coordinates k and l;

$DQ_{k,l}$ is an imaginary component value of said second resulting signal vector component digital signals and corresponds to an imaginary component value of said resulting signal vector associated with one of said image elements having coordinates k and l;

$C_{k-m,l-n}$ is the corrected signal vector associated with one of said image elements having coordinates k-m and l-n;

$A_{k-m}$ is the correction parameter associated with one of said image elements having coordinate k-m;

$B_{k-m,l-n}$ is the signal vector associated with one of said image elements having coordinates k-m and l-n;

$BI_{k-m,l-n}$ is a real component value associated with said first signal vector component digital signals and corresponds to the real component value of said signal vector associated with one of said image elements having coordinates k-m and l-n;

$BQ_{k-m,l-n}$ is an imaginary component value associated with said second signal vector component digital signals and corresponds to the imaginary component value of said signal vector associated with one of said image elements having coordinates k-m and l-n;

$L_{m,n}$ is a normalized focusing function data corresponding to one of said image elements having coordinates m and n;

$LI_{m,n}$ is a real component value of said normalized focusing function data corresponding to one of said image elements having coordinates m and n;

$LQ_{m,n}$ is an imaginary component value of said normalized focusing function data corresponding to one of said image elements having coordinates m and n;

$L_{norm}$ is a focusing function normalization parameter;

$LI_{norm}$ is a real component value of said focusing function normalization parameter;

$LQ_{norm}$ is an imaginary component value of said focusing function normalization parameter;

$F_{m,n}$ is the focusing function data corresponding to one of said image elements having coordinates m and n;

$FI_{m,n}$ is a real component value of said focusing function data corresponding to one of said image elements having coordinates m and n;

$FQ_{m,n}$ is an imaginary component value of said focusing function data corresponding to one of said image elements having coordinates m and n.

15. An ultrasonic transmission imaging apparatus as claimed in claim 14, wherein said normalization parameter $L_{norm}$ can be derived according to the following mathematical expression:

$$L_{norm} = \sqrt{\sum_{m=-M}^{M} \sum_{n=-N}^{N} (F_{m,n} F_{m,n})} \quad (15)$$

16. An ultrasonic transmission imaging apparatus as claimed in claim 14, wherein said focusing function data further establishes, for each image element comprised in said focusing aperture, an amplitude displacement value relative to a reference amplitude value associated with said focal line, said focusing function data $F_{m,n}$ being derived according to the following mathematical expressions:

$$FI_{m,n} = FI(x_m,y_n,\omega,\lambda z) = \quad (17)$$

$$e^{-(x_m^2+y_n^2)K(\omega,\lambda,z)} \cos\left[\frac{\lambda z}{\pi \omega^2} (x_m^2 + y_n^2)K(\omega,\lambda,z)\right]$$

$$FI_{m,n} = FI(x_m,y_n,\omega,\lambda z) = \quad (18)$$

$$e^{-(x_m^2+y_n^2)K(\omega,\lambda,z)} \sin\left[\frac{\lambda z}{\pi \omega^2} (x_m^2 + y_n^2)K(\omega,\lambda,z)\right]$$

$$K(\omega,\lambda,z) = \frac{\pi^2 \omega^2}{\lambda^2 z^2 + \pi^2 \omega^2} \quad (19)$$

$$x_m = m\, dx \quad (20)$$

$$y_m = n\, dy \quad (21)$$

wherein:

$x_m$ and $y_n$ are physical position coordinates according to first and second axis X and Y of the cartesian reference system for said ultrasonic detectors array and associated image elements, and associated with one of said image elements having coordinates m and n;

$K(w\lambda,z)$ is a wave propagation damping factor;

dx is physical dimension along X axis of said image elements dy is physical dimension along Y axis of said image elements w is a desired image resolution;

$\lambda$ is the wavelength of the ultrasonic waves;

z is the distance between said focus point and a nearest one of said ultrasonic detectors.

17. An ultrasonic transmission imaging apparatus as claimed in claim 12, wherein said computer means derives a normalized focusing function data according to the following mathematical expressions:

$$L_{m,n} = \frac{F_{m,n}}{L_{norm}} = LI_{m,n} + iLQ_{m,n} \quad (12)$$

$$F_{m,n} = FI_{m,n} + iFQ_{m,n} \quad (13)$$

$$L_{norm} = LI_{norm} + iLQ_{norm} \quad (14)$$

wherein:

m and n are secondary coordinates according to first and second axis X and Y of the cartesian reference system for said ultrasonic detector array and associated image elements, with m=−M,M and n=−N,N, the size of said focusing function data being equal to (2M+1)(2N+1);

$L_{m,n}$ is a normalized focusing function data corresponding to one of said image elements having coordinates m and n;

$LI_{m,n}$ is a real component value of said normalized focusing function data corresponding to one of said image elements having coordinates m and n;

$LQ_{m,n}$ is an imaginary component value of said normalized focusing function data corresponding to one of said image elements having coordinates m and n;

$L_{norm}$ is a focusing function normalization parameter;

$LI_{norm}$ is a real component value of said focusing function normalization parameter;

$LQ_{norm}$ is an imaginary component value of said focusing function normalization parameter;

$F_{m,n}$ is the focusing function data corresponding to one of said image elements having coordinates m and n;

$FI_{m,n}$ is a real value of said focusing function data corresponding to one of said image elements having coordinates m and n;

$FQ_{m,n}$ is an imaginary component value of said focusing function data corresponding to one of said image elements having coordinates m and n; said computer further applies a first Fourier transform operation on said normalized focusing function data $L_{m,n}$ according to said coordinates k or l to produce transformed focusing function data in a spatial frequency domain, a second Fourier transform operation to values of said pairs of first and second corrected signal vector component digital signals according to said coordinates k or l to produce transformed signal vector component values in the spatial frequency domain, a multiplication of corresponding values of said transformed focusing function data and said transformed signal vector component values followed by an inverse Fourier Transform operation on the result thereof to produce said corresponding pairs of first and second resulting signal vector component digital signals forming said focused digital image representation of said object traversing ultrasonic waves according to the following mathematical expression:

$$D_{k,l} = DI_{k,l} + iDQ_{k,l} \quad (16)$$

wherein:

$D_{k,l}$ is a resulting signal vector associated with one of said image elements having coordinates k and l;

$DI_{k,l}$ is a real component value of said first resulting signal vector component digital signals and corresponds to a real component value of said resulting signal vector associated with one of said image elements having coordinates k and l;

$DQ_{k,l}$ is an imaginary value of said second resulting signal vector component digital signals and corresponds to an imaginary component value of said resulting signal vector associated with one of said image elements having coordinates k and l.

18. An ultrasonic transmission imaging apparatus as claimed in claim 17, wherein said normalization parameter $L_{norm}$ can be derived according to the following mathematical expression:

$$L_{norm} = \sqrt{\sum_{m=-M}^{M} \sum_{n=-N}^{N} (F_{m,n} F_{m,n})} \quad (15)$$

19. An ultrasonic transmission imaging apparatus as claimed in claim 17, wherein said focusing function data further establishes, for each image element comprised in said focusing aperture, an amplitude displacement value relative to a reference amplitude value associated with said focal line, said focusing function data $F_{m,n}$ being derived according to the following mathematical expressions:

$$FI_{m,n} = FI(x_m,y_n,\omega,\lambda z) = \quad (17)$$

$$e^{-(x_m^2+y_n^2)K(\omega,\lambda,z)} \cos\left[\frac{\lambda z}{\pi \omega^2} (x_m^2 + y_m^2)K(\omega,\lambda,z)\right]$$

-continued $$FI_{m,n} = FI(x_m, y_n, \omega, \lambda, z) = \quad (18)$$

$$e^{-(x_m^2 + y_n^2)K(\omega,\lambda,z)} \sin\left[\frac{\lambda z}{\pi \omega^2} (x_m^2 + y_n^2) K(\omega,\lambda,z)\right]$$

$$K(\omega,\lambda,z) = \frac{\pi^2 \omega^2}{\lambda^2 z^2 + \pi^2 \omega^2} \quad (19)$$

$$x_m = m\, dx \quad (20)$$

$$y_m = n\, dy \quad (21)$$

wherein:

$x_m$ and $y_n$ are physical position coordinates according to first and second axis X and Y of the cartesian reference system for said ultrasonic detectors array and associated image elements, and associated with one of said image elements having coordinates m and n;

$K(w,\lambda,z)$ is a wave propagation damping factor;

dx is physical dimension along X axis of said image elements dy is physical dimension along Y axis of said image elements w is a desired image resolution;

$\lambda$ is the wavelength of the ultrasonic waves;

z is the distance between said focus point and a nearest one of said ultrasonic detectors.

20. An ultrasonic transmission imaging apparatus as claimed in claim 3, further comprising a plurality of multiplexers coupling said ultrasonic detector means output with said signal vector components detector means, said computer means being connected to said multiplexers for control thereof, each of said multiplexers having a plurality of inputs respectively fed by a plurality of said electrical signals, each of said multiplexers further having respective output through which each one of said plurality of said electrical signals is sequentially transferred to said signal vector components detector means.

21. An ultrasonic transmission imaging apparatus as claimed in claim 20, wherein each of said multiplexers is provided with preamplifier means for amplifying each one of said plurality of said electrical signals prior transferring thereof to said signal vector components detector means.

22. An ultrasonic transmission imaging apparatus as claimed in claim 20, wherein said signal vector components detector means comprises a plurality of synchronous detector circuits comprising first and second multipliers having respective signal inputs coupled to respective ones of said multiplexer outputs and having respective reference inputs means, said signal vector components detector means further comprising a reference signals generator means having first and second outputs means respectively connected to said reference inputs means provided on said first and second multipliers to respectively sent thereto an first reference signal and a second reference signal in phase quadrature with said first reference signal and at a common operating frequency, said computer means being connected to said reference signals generator means for control thereof, said first and second multiplier means further having respective outputs for respectively producing a first signal comprising a primary signal vector component and a second signal comprising a secondary quadrature phased signal vector component, each of said synchronous detector circuits further comprising first and second lowpass filters respectively coupled to said multiplier outputs and in series with first and second output amplifiers for producing at first and second outputs thereof said pairs of first and second signal vector component signals associated with a corresponding one of said plurality of said electrical signals, said computer means being connected to said output amplifiers for control thereof, said apparatus further comprising amplifier means coupled to a third output means provided on said reference signals generator means for receiving a driving reference signal to produce at an output thereof an amplified driving reference signal at said common operating frequency, said computer means being connected to said amplifier means for control thereof, said ultrasonic emitter means receiving said reference signal at an input thereof for producing said continuous coherent ultrasonic waves.

23. An ultrasonic transmission imaging apparatus as claimed in claim 20, wherein each of said synchronous detector circuits further comprises an input amplifier coupling said first and second multipliers signal inputs with a corresponding one of said multiplexer outputs, said computer means being connected to said input amplifier means for control thereof, said input amplifier means amplifying each one of said plurality of said electrical signals prior sending thereof to said first and second multipliers signal inputs, each of said synchronous detector circuits further comprising first and second intermediate amplifier means for coupling said first and second lowpass filters respectively to said multiplier outputs.

24. An ultrasonic transmission imaging apparatus as claimed in claim 20, wherein said first and second reference signals are square wave reference signals, said apparatus further comprising a preamplifier in series with a bandpass filter for coupling said amplifier means to either of said first or second reference generator outputs.

25. An ultrasonic transmission imaging apparatus as claimed in claim 3, wherein said scanning ultrasonic detectors array means is a scanning ultrasonic detectors linear array.

26. An ultrasonic transmission imaging apparatus as claimed in claim 3, wherein said scanning ultrasonic detectors array means is comprised of a plurality of scanning ultrasonic detectors arrays covering respective complementary portions of said detection zone.

27. An ultrasonic transmission imaging apparatus as claimed in claim 3, wherein said apparatus is used as a fish fillet imaging apparatus, said object being a fish fillet, said coupling means is a mass of water traversing said detecting zone and surrounding said fish fillet to be inspected, said means for creating a scanning relative movement between said object to be inspected and said ultrasonic emitter means and scanning ultrasonic detectors array means is a fish fillet transport unit for immersing said fish fillet to be inspected in said water mass and in said detecting zone and for bringing an inspected fish fillet out of said water mass toward an output provided on said transport unit, and wherein said apparatus further comprises:

a frame on which are mounted said ultrasonic emitter means, said scanning ultrasonic detectors array means and said fish fillet transport unit;

a main tank mounted on said frame containing said detecting zone and filled with said water mass, said ultrasonic emitter means and said scanning ultrasonic detectors array means being immersed in said water mass and being adjustably secured to said frame so as to be maintained in a stationary positioned within said main tank.

28. An ultrasonic imaging apparatus as claimed in claim 27, wherein said fish fillet transport unit comprises:

first conveyer means mounted at a first end of said fish fillet transport unit, said first conveyer means having an input end for receiving said fish fillet to be inspected, said first conveyer means immersing said fish fillet in said water mass and carrying said fish fillet toward an output end provided on said first conveyer means;

second conveyer means mounted in said main tank and totally immersed in said water mass, said second conveyer means having a first end extending over said first conveyer means output end and an output end, said main tank being provided with a plurality of first water feeding means tranversely extending therethrough and disposed from said first conveyer means output end and under said second conveyer means, said first water feeding means having first nozzle means projecting series of water jets toward said fish fillet to be inspected to move thereof from the vicinity of said first conveyer means output end to an underside surface of said second conveyer means, said main tank being provided with at least one second water feeding means tranversely extending therethrough under said second conveyer means output end, said second water feeding means having at least one second nozzle for projecting series of water jets toward said fish fillet to be inspected to propel thereof from the vicinity of said second conveyer means output end toward said detecting zone;

third conveyer means mounted at a second end of said fish fillet transport unit, said third conveyer means having an input end for receiving an inspected fish fillet as it comes out of said detecting zone, to bring said inspected fish fillet out of said water mass toward said transport unit output;

conveyer driving motor means coupled to said first, second and third conveyer means for driving thereof;

water supply means coupled to said first and second water feeding means for supplying under pressure said water thereto.

29. An ultrasonic imaging apparatus as claimed in claim 28, wherein said second conveyer means is a chain conveyer having an upper portion and a lower portion, said main tank is further provided with at least one third water feeding means tranversely extending therethrough between said upper portion and said lower portion in the vicinity of said second conveyer means output, said third water feeding means having at least one third nozzle means projecting series of water jets toward said fish fillet to be inspected to remove thereof from the underside surface of said second conveyer means at the vicinity of said output end thereof, said water supply means being coupled to said at least one third water feeding means for supplying under pressure said water thereto.

30. An ultrasonic imaging apparatus as claimed in claim 29, wherein said second water feeding means is further provided with respective valve means to control flow of said water therethrough.

31. An ultrasonic imaging apparatus as claimed in claim 28, wherein said fish fillet transport unit further comprises:

a filtration tank positioned at said fish fillet transport unit second end and under said third conveyer means output end, said filtration tank being in fluid communication with an outlet provided on said main tank to receive said water flowing out of said main tank, said filtration tank being provided with filter means to filter said water received from said main tank, said filtration tank having an outlet through which filtered water is flowing;

wherein said water supply means is a pump having an inlet coupled to said filtration tank outlet and an outlet coupled to said first, second and third water feeding means for supplying thereof with said filtered water.

32. An ultrasonic imaging apparatus as claimed in claim 28, wherein said first conveyer means comprises:

a feeding conveyer adapted to receive said fish fillet to be inspected at said first conveyer means input end for carrying said fish fillet to an output end provided on said feeding conveyer over said main tank and toward said water mass;

an immersing conveyer mounted in said main tank for receiving said fish fillet from said feeding conveyer, said immersing conveyer being totally immersed in said water mass to immerse said fish fillet therein and carrying said fish fillet toward an output end provided on said first conveyer means.

33. An ultrasonic imaging apparatus as claimed in claim 28, wherein said first water feeding means is further provided with respective valve means to control flow of said water therethrough.

34. An ultrasonic transmission imaging apparatus comprising:

ultrasonic emitter means for producing substantially continuous coherent ultrasonic waves toward an object to be inspected positioned in a detecting zone;

ultrasonic coupling means in contact with said object on opposed sides thereof, for providing transmission of said ultrasonic waves thereto, transfer of said ultrasonic waves therethrough, and transmission of object traversing ultrasonic waves out of said object;

a two-dimensional ultrasonic detectors array means comprising a plurality of rows of ultrasonic detectors disposed in a parallel relationship and adapted to receive said object traversing ultrasonic waves for producing a plurality of corresponding series of electrical signals coming from said ultrasonic detectors, said series of electrical signals respectively characterizing transmission of said ultrasonic waves through said object in a plurality of transmission planes substantially defined by said plurality of rows of ultrasonic detectors and a direction perpendicular thereto and to said emitter means, said series of electrical signals being respectively associated with series of image elements;

dynamic focusing means for producing focused image element data from said series of electrical signals and associated with each one of said ultrasonic detectors, said focusing means phase shifting each one of said series of electrical signals in accordance with each location within said object to be imaged in focus for producing a composite image.

35. An ultrasonic transmission imaging apparatus as claimed in claim 34, wherein said dynamic focusing means comprise:

signal vector components detector means adapted to receive said electrical signals, said signal vector components detector means detecting signal vector components for each of said electrical signals, to produce pairs of first and second signal vector component signals corresponding to said electrical signals;

computer means for controlling said apparatus and adapted to receive said pairs of first and second signal vector component signals, said computer having memory means for storing said pairs of first and second signal vector component signals and for storing focusing function data establishing, for each image element comprised in a focusing aperture comprising a plurality of juxtaposed image elements of said series of image elements, a phase displacement value relative to a reference phase value associated with a focal line passing through a focus point and a center of said aperture, said computer means using said focusing function data to produce corresponding pairs of first and second resulting signal vector component signals forming a focused image representation of said object traversing ultrasonic waves.

36. An ultrasonic transmission imaging apparatus as claimed in claim 35, wherein said signal vector component detector means include analog-to-digital converter means adapted to receive said pairs of first and second signal vector component signals for producing corresponding pairs of first and second signal vector component digital signals.

37. An ultrasonic transmission imaging apparatus as claimed in claim 36, wherein said computer means resulting amplitude signals corresponding to said pairs of first and second resulting signal vector component digital signals, said apparatus further comprising display means adapted to receive said resulting amplitude signals and to produce a visual display of said digital image representation of said object traversing ultrasonic waves.

38. An ultrasonic transmission imaging apparatus as claimed in claim 36, further comprising multiplexer means coupling said ultrasonic detector means output with said signal vector components detector means, said computer means being connected to said multiplexer means for control thereof, said multiplexer means having a plurality of inputs respectively fed by each one of said electrical signals, said multiplexer means further having output through which each one of said electrical signals is sequentially transferred to said signal vector components detector means.

39. An ultrasonic transmission imaging apparatus as claimed in claim 38, wherein said multiplexer means is provided with preamplifier means for amplifying each one of said electrical signals prior transferring thereof to said signal vector components detector means.

40. An ultrasonic transmission imaging apparatus as claimed in claim 38, wherein said signal vector component detector means is a synchronous detector circuit comprising first and second multipliers having respective signal inputs coupled to said multiplexer means output and respective reference inputs means, said synchronous detector circuit further comprising a reference signals generator means having first and second output means respectively connected to said reference input means provided on said first and second multipliers to respectively sent thereto a first reference signal and a second reference signal in phase quadrature with said first reference signal at a common operating frequency, said computer means being connected to said reference signals generator for control thereof, said first and second multiplier means further having respective outputs for respectively producing a first signal comprising an primary signal vector component and a second signal comprising a secondary quadrature phased signal vector component, said synchronous detector circuit further comprises first and second lowpass filters respectively coupled to said multiplier outputs and in series with respective first and second output amplifiers for producing at first and second outputs thereof said pairs of first and second signal vector component signals corresponding to said electrical signals, said computer means being connected to said output amplifiers for control thereof, said apparatus further comprising amplifier means coupled to a third output means provided on said reference signals generator means for receiving a driving reference signal to produce at an output thereof an amplified driving reference signal at said common operating frequency, said computer means being connected to said amplifier means for control thereof, said ultrasonic emitter means receiving said amplified driving reference signal at an input thereof for producing said continuous coherent ultrasonic waves.

41. An ultrasonic transmission imaging apparatus as claimed in claim 40, wherein said synchronous detector circuit further comprises an input amplifier coupling said first and second multipliers signal inputs with said multiplexer means output, said computer means being connected to said input amplifier means for control thereof, said input amplifier means amplifying each one of said electrical signals prior sending thereof to said first and second multipliers signal inputs, said synchronous detector circuit further comprising first and second intermediate amplifier means for coupling said first and second lowpass filters respectively to said multiplier outputs.

42. An ultrasonic transmission imaging apparatus as claimed in claim 40, wherein said first and second reference signals are square wave reference signals, said apparatus further comprising a preamplifier in series with a bandpass filter for coupling said amplifier means to said third output means provided on said reference signals generator means.

43. An ultrasonic transmission imaging apparatus as claimed in claim 36, wherein said computer means detects the presence of said object to be inspected in said detecting zone prior producing said corresponding pairs of first and second resulting signal vector component digital signals forming said digital image representation of said object traversing ultrasonic waves.

44. An ultrasonic transmission imaging apparatus as claimed in claim 43, wherein said computer means detect the presence of an object to be inspected in said detecting zone by deriving a mean intensity value for a plurality of said pairs of first and second signal vector component digital signals corresponding with a plurality of said electrical signals coming from said ultrasonic detectors and by comparing said mean intensity value with a predetermined presence threshold value.

45. An ultrasonic transmission imaging apparatus as claimed in claim 36, wherein said first and second signal vector component digital signals are respectively associated with a real component value and an imaginary component value, said computer means multiplying said components values of said first and second signal vector component digital signals with respective real component value and imaginary component value of a correction parameter prior using said focusing function data to produce a corrected signal vector, said correction parameter and said corrected signal vector being defined according to the following mathematical expressions:

$$A_{k,l} = AI_{k,l} + iAQ_{k,l} = \frac{T}{M_{k,l}} \tag{4}$$

$$M_{k,l} = \frac{i}{J} \sum_{j=0}^{J-1} S_{j,k,l} \tag{5}$$

$$S_{j,k,l} = SI_{j,k,l} + iSQ_{j,k,l} \tag{6}$$

$$C_{k,l} = A_{k,l}B_{k,l} = CI_{k,l} + iCQ^{-k,l} \tag{7}$$

$$B_{k,l} = BI_{k,l} + iBQ_{k,l} \tag{8}$$

wherein k and l are primary coordinates according to first and second axis X and Y of a cartesian reference system for the ultrasonic detector array and associated image elements, with k=0,K−1 and l=0,L−1;

$A_{k,l}$ is the correction parameter associated with one of the image elements having coordinates k and l, this correction parameter compensating for detector sensibility variation among corresponding ones of the ultrasonic detectors;

$AI_{k,l}$ is the real component value of the correction parameter associated with one of the image elements having coordinate k;

$AQ_k$ is the imaginary component value of the correction parameter associated with one of the image elements having coordinates k and l;

T is a target parameter being characterized by a target uniform amplitude and phase values corresponding to a reference target image;

$M_{k,l}$ is a mean value of sample pairs of first and second signal vector component signals associated with one of the image elements having coordinates k and l, prior detecting the presence of an object apparently moving in the detecting zone;

J is a predetermined number of said sample pairs of first and second signal vector component signals;

$S_{j,k,l}$ is the signal vector of a sample j associated with one of said image elements having coordinates k and l;

$SI_{j,k,l}$ is a real component value associated with said first signal vector component digital signals and corresponds to the real component value of said signal vector of a sample j associated with one of said image elements having coordinates k and l;

$SQ_{j,k,l}$ is an imaginary component associated with said second signal vector component digital signals and corresponds to the imaginary component value of said signal vector of a sample j associated with one of said image elements having coordinates k and l;

$C_{k,l}$ is a corrected signal vector associated with one of said image elements having coordinates k and l;

$CI_{k,l}$ is a real component value associated with said first corrected signal vector component digital signals and corresponds to a real component value of said corrected signal vector associated with one of said image elements having coordinates k and l;

$CQ_{k,l}$ is an imaginary component value associated with said second corrected signal vector component digital signals and corresponds to an imaginary component value of said corrected signal vector associated with one of the image elements having coordinates k and l;

$B_{k,l}$ is the signal vector associated with one of said image elements having coordinates k and l;

$BI_{k,l}$ is a real component value associated with said first signal vector component digital signals and corresponds to the real component value of said signal vector associated with one of said image elements having coordinates k and l;

$BQ_{k,l}$ is an imaginary component value associated with said second signal vector component digital signals and corresponds to the imaginary component value of said signal vector associated with one of said image elements having coordinates k and l.

46. An ultrasonic transmission imaging apparatus as claimed in claim 45, wherein said computer means compares values of said correction parameter with a predetermined correction threshold value to detect corresponding unusable ones of said ultrasonic detectors, said computer means substitute for corresponding ones of said pairs of first and second signal vector component signals respective first and second signal vector component signals corresponding to proximate usable ones of said ultrasonic detectors.

47. An ultrasonic transmission imaging apparatus as claimed in claim 46, wherein said computer means applies a convolution technique to produce corresponding pairs of first and second resulting signal vector component digital signals forming said focused digital image representation of said object traversing ultrasonic waves according to the following mathematical expressions:

$$D_{k,l} = \sum_{m=-M}^{M} \sum_{n=-N}^{N} C_{k-m,l-n} L_{m,n} = DI_{k,l} + iDQ_{k,l} \quad (9)$$

$$C_{k-m,l-n} = A_{k-m} B_{k-m,l-n} \quad (10)$$

$$B_{k-m,l-n} = BI_{k-m,l-n} + iBQ_{k-m,l-n} \quad (11)$$

$$L_{m,n} = \frac{F_{m,n}}{L_{norm}} = LI_{m,n} + iLQ_{m,n} \quad (12)$$

$$F_{m,n} = FI_{m,n} + iFQ_{m,n} \quad (13)$$

$$L_{norm} = LI_{norm} + iLQ_{norm} \quad (14)$$

wherein:

m and n are secondary coordinates according to first and second axis X and Y of the cartesian reference system for said ultrasonic detector array and associated image elements, with m=−M,M and n=−N,N, the size of said focusing function data being equal to (2M+1)(2N+1);

$D_{k,l}$ is a resulting signal vector associated with one of said image elements having coordinates k and l;

$DI_{k,l}$ is a real component value of said first resulting signal vector component digital signals and corresponds to a real component value of said resulting signal vector associated with one of said image elements having coordinates k and l;

$DQ_{k,l}$ is an imaginary component value of said second resulting signal vector component digital signals and corresponds to an imaginary component value of said resulting signal vector associated with one of said image elements having coordinates k and l;

$C_{k-m,l-n}$ is the corrected signal vector associated with one of said image elements having coordinates k-m and l-n;

$A_{k-m}$ is the correction parameter associated with one of said image elements having coordinate k-m;

$B_{k-m,l-n}$ is the signal vector associated with one of said image elements having coordinates k-m and l-n;

$BI_{k-m,l-n}$ is a real component value associated with said first signal vector component digital signals and corresponds to the real component value of said signal vector associated with one of said image elements having coordinates k-m and l-n;

$BQ_{k-m,l-n}$ is an imaginary component value associated with said second signal vector component digital signals and corresponds to the imaginary component value of said signal vector associated with one of said image elements having coordinates k-m and l-n;

$L_{m,n}$ is a normalized focusing function data corresponding to one of said image elements having coordinates m and n;

$LI_{m,n}$ is a real component value of said normalized focusing function data corresponding to one of said image elements having coordinates m and n;

$LQ_{m,n}$ is an imaginary component value of said normalized focusing function data corresponding to one of said image elements having coordinates m and n;

$L_{norm}$ is a focusing function normalization parameter;

$LI_{norm}$ is a real component value of said focusing function normalization parameter;

$LQ_{norm}$ is an imaginary component value of said focusing function normalization parameter;

$F_{m,n}$ is the focusing function data corresponding to one of said image elements having coordinates m and n;

$FI_{m,n}$ is a real component value of said focusing function data corresponding to one of said image elements having coordinates m and n;

$FQ_{m,n}$ is an imaginary component value of said focusing function data corresponding to one of said image elements having coordinates m and n;

48. An ultrasonic transmission imaging apparatus as claimed in claim 47, wherein said normalization parameter $L_{norm}$ can be derived according to the following mathematical expression:

$$L_{norm} = \sqrt{\sum_{m=-M}^{M} \sum_{n=-N}^{N} (F_{m,n} F_{m,n})} \qquad (15)$$

49. An ultrasonic transmission imaging apparatus as claimed in claim 47, wherein said focusing function data further establishes, for each image element comprised in said focusing aperture, an amplitude displacement value relative to a reference amplitude value associated with said focal line, said focusing function data $F_{m,n}$ being derived according to the following mathematical expressions:

$$FI_{m,n} = FI(x_m, y_n, \omega, \lambda z) = \qquad (17)$$

$$e^{-(x_m^2 + y_n^2)K(\omega,\lambda,z)} \cos\left[\frac{\lambda z}{\pi \omega^2}(x_m^2 + y_m^2)K(\omega,\lambda,z)\right]$$

$$FI_{m,n} = FI(x_m, y_n, \omega, \lambda z) = \qquad (18)$$

$$e^{-(x_m^2 + y_n^2)K(\omega,\lambda,z)} \sin\left[\frac{\lambda z}{\pi \omega^2}(x_m^2 + y_n^2)K(\omega,\lambda,z)\right]$$

$$K(\omega,\lambda,z) = \frac{\pi^2 \omega^2}{\lambda^2 z^2 + \pi^2 \omega^2} \qquad (19)$$

$$x_m = m\, dx \qquad (20)$$

$$y_m = n\, dy \qquad (21)$$

wherein:

$x_m$ and $y_n$ are physical position coordinates according to first and second axis X and Y of the cartesian reference system for said ultrasonic detectors array and associated image elements, and associated with one of said image elements having coordinates m and n;

$K(w,\lambda,z)$ is a wave propagation damping factor;

dx is physical dimension along X axis of said image elements dy is physical dimension along Y axis of said image elements w is a desired image resolution;

$\lambda$ is the wavelength of the ultrasonic waves;

z is the distance between said focus point and a nearest one of said ultrasonic detectors.

50. An ultrasonic transmission imaging apparatus as claimed in claim 45, wherein said computer means derives a normalized focusing function data according to the following mathematical expressions:

$$L_{m,n} = \frac{F_{m,n}}{L_{norm}} = LI_{m,n} + iLQ_{m,n} \qquad (12)$$

$$F_{m,n} = FI_{m,n} + iFQ_{m,n} \qquad (13)$$

$$L_{norm} = LI_{norm} + iLQ_{norm} \qquad (14)$$

wherein:

m and n are secondary coordinates according to first and second axis X and Y of the cartesian reference system for said ultrasonic detector array and associated image elements, with m=−M,M and n=−N,N, the size of said focusing function data being equal to (2M+1)(2N+1);

$L_{m,n}$ is a normalized focusing function data corresponding to one of said image elements having coordinates m and n;

$LI_{m,n}$ is a real component value of said normalized focusing function data corresponding to one of said image elements having coordinates m and n;

$LQ_{m,n}$ is an imaginary component value of said normalized focusing function data corresponding to one of said image elements having coordinates m and n;

$L_{norm}$ is a focusing function normalization parameter;

$LI_{norm}$ is a real component value of said focusing function normalization parameter;

$LQ_{norm}$ is an imaginary component value of said focusing function normalization parameter;

$F_{m,n}$ is the focusing function data corresponding to one of said image elements having coordinates m and n;

$FI_{m,n}$ is a real component value of said focusing function data corresponding to one of said image elements having coordinates m and n;

$FQ_{m,n}$ is an imaginary component value of said focusing function data corresponding to one of said image elements having coordinates m and n; said computer further applies a first Fourier transform operation on said normalized focusing function data $L_{m,n}$ according to said coordinates k or l to produce transformed focusing function data in a spatial frequency domain, a second Fourier transform operation to values of said pairs of first and second corrected signal vector component digital signals according to said coordinates k or l to produce transformed signal vector component values in the spatial frequency domain, a multiplication of corresponding values of said transformed focusing function data and said transformed signal vector component values followed by an inverse Fourier Transform operation on the result thereof to produce said corresponding pairs of first and second resulting signal vector component digital signals forming said focused digital image representation of said object traversing ultrasonic waves according to the following mathematical expression:

$$D_{k,l} = DI_{k,l} + iDQ_{k,l} \qquad (16)$$

wherein:

$D_{k,l}$ is a resulting signal vector associated with one of said image elements having coordinates k and l;

$DI_{k,l}$ is a real component value of said first resulting signal vector component digital signals and corresponds to a real component value of said resulting signal vector associated with one of said image elements having coordinates k and l;

$DQ_{k,l}$ is an imaginary value of said second resulting signal vector component digital signals and corresponds to an imaginary component value of said resulting signal vector associated with one of said image elements having coordinates k and l.

51. An ultrasonic transmission imaging apparatus as claimed in claim 50, when said normalization parameter $L_{norm}$ can be derived according to the following mathematical expression:

$$L_{norm} = \sqrt{\sum_{m=-M}^{M} \sum_{n=-N}^{N} (F_{m,n} F_{m,n})} \quad (15)$$

52. An ultrasonic transmission imaging apparatus as claimed in claim 50, wherein said focusing function data further establishes, for each image element comprised in said focusing aperture, an amplitude displacement value relative to a reference amplitude value associated with said focal line, said focusing function data $F_{m,n}$ being derived according to the following mathematical expressions:

$$FI_{m,n} = FI(x_m, y_n, \omega, \lambda, z) = \quad (17)$$

$$e^{-(x_m^2 + y_n^2) K(\omega, \lambda, z)} \cos\left[ \frac{\lambda z}{\pi \omega^2} (x_m^2 + y_{-n}^2) K(\omega, \lambda, z) \right]$$

$$FI_{m,n} = FI(x_m, y_n, \omega, \lambda, z) = \quad (18)$$

$$e^{-(x_m^2 + y_n^2) K(\omega, \lambda, z)} \sin\left[ \frac{\lambda z}{\pi \omega^2} (x_m^2 + y_n^2) K(\omega, \lambda, z) \right]$$

$$K(\omega, \lambda, z) = \frac{\pi^2 \omega^2}{\lambda^2 z^2 + \pi^2 \omega^2} \quad (19)$$

$$x_m = m \, dx \quad (20)$$

$$y_m = n \, dy \quad (21)$$

wherein:

$x_m$ and $y_n$ are physical position coordinates according to first and second axis X and Y of the cartesian reference system for said ultrasonic detectors array and associated image elements, and associated with one of said image elements having coordinates m and n;

$K(w, \lambda, z)$ is a wave propagation damping factor;

dx is physical dimension along X axis of said image elements dy is physical dimension along Y axis of said image elements w is a desired image resolution;

$\lambda$ is the wavelength of the ultrasonic waves;

z is the distance between said focus point and a nearest one of said ultrasonic detectors.

53. An ultrasonic transmission imaging apparatus as claimed in claim 36, further comprising a plurality of multiplexers coupling said ultrasonic detector means output with said signal vector components detector means, said computer means being connected to said multiplexers for control thereof, each of said multiplexers having a plurality of inputs respectively fed by a plurality of said electrical signals, each of said multiplexers further having respective output through which each one of said plurality of said electrical signals is sequentially transferred to said signal vector components detector means.

54. An ultrasonic transmission imaging apparatus as claimed in claim 53, wherein each of said multiplexers is provided with preamplifier means for amplifying each one of said plurality of said electrical signals prior transferring thereof to said signal vector components detector means.

55. An ultrasonic transmission imaging apparatus as claimed in claim 53, wherein said signal vector components detector means comprises a plurality of synchronous detector circuits comprising first and second multipliers having respective signal inputs coupled to respective ones of said multiplexer outputs and having respective reference inputs means, said signal vector components detector means further comprising a reference signals generator means having first and second output means respectively connected to said reference inputs provided on said first and second multipliers to respectively sent thereto a first reference signal and a second reference signal in phase quadrature with said first reference signal at a common operating frequency, said computer means being connected to said reference signals generator means for control thereof, said first and second multiplier means further having respective outputs for respectively producing a first signal comprising a primary signal vector component and a second signal comprising a secondary quadrature phased signal vector component, each of said synchronous detector circuits further comprising first and second lowpass filters respectively coupled to said multiplier outputs and in series with first and second output amplifiers for producing at first and second outputs thereof said pairs of first and second signal vector component signals associated with a corresponding one of said plurality of said electrical signals, said computer means being connected to said output amplifiers for control thereof, said apparatus further comprising amplifier means coupled to a third output means provided on said reference signals generator means for receiving a driving reference signal to produce at an output thereof an amplified driving reference signal at said common operating frequency, said ultrasonic emitter means receiving said amplified driving reference signal at an input thereof for producing said continuous coherent ultrasonic waves.

56. An ultrasonic transmission imaging apparatus as claimed in claim 55, wherein each of said synchronous detector circuits further comprises an input amplifier coupling said first and second multipliers signal inputs with a corresponding one of said multiplexer outputs, said computer means being connected to said input amplifier means for control thereof, said input amplifier means amplifying each one of said plurality of said electrical signals prior sending thereof to said first and second multipliers signal inputs, each of said synchronous detector circuits further comprising first and second intermediate amplifier means for coupling said first and second lowpass filters respectively to said multiplier outputs.

57. An ultrasonic transmission imaging apparatus as claimed in claim 55, wherein said first and second reference signals are square wave reference signals, said apparatus further comprising a preamplifier in series with a bandpass filter for coupling said amplifier means to either of said first or second reference generator outputs.

58. An ultrasonic transmission imaging apparatus as claimed in claim 36, wherein said two-dimensional ultrasonic detectors array means is comprised of a plurality of two-dimensional ultrasonic detectors arrays covering respective complementary portions of said detection zone.

59. An ultrasonic transmission imaging method comprising steps of:

(i) producing substantially continuous coherent ultrasonic waves toward an object to be inspected positioned in a detecting zone;

(ii) providing transmission of said ultrasonic waves to said object to be inspected, transfer of said ultrasonic waves therethrough, and transmission of object traversing ultrasonic waves out of said object;

(iii) receiving said object traversing ultrasonic waves and producing a plurality of series of electrical signals characterizing transmission of said ultrasonic waves through said object in a plurality of transmission planes, said series of electrical signals being respectively associated with series of image elements;

(iv) detecting signal vector components for each of said electrical signals and producing pairs of first and second signal vector component signals corresponding to said electrical signals;

(v) digitally converting said pairs of first and second signal vector component signals and producing corresponding pairs of first and second signal vector component digital signals;

(vi) providing focusing function data establishing, for each image element comprised in a focusing aperture comprising a plurality of juxtaposed image elements of said series of image elements, a phase displacement value relative to a reference phase value associated with a focal line passing through a focus point and a center of said aperture; and (vii) using said focusing function data to produce corresponding pairs of first and second resulting signal vector component digital signals forming focused digital image elements representative of said object.

60. An ultrasonic transmission imaging method as claimed in claim 59, wherein after said step (vii) there are provided steps of:

(a) producing resulting amplitude signals corresponding to said pairs of first and second resulting signal vector component digital signals; and (b) producing a visual display of said digital image representation of said object traversing ultrasonic waves.

61. An ultrasonic transmission imaging method as claimed in claim 59, wherein after said step (v) there is provided a step of:

(a) detecting the presence of said object to be inspected apparently moving in said detecting zone.

62. An ultrasonic transmission imaging method as claimed in claim 61 wherein said step (a) is carried out by deriving a mean intensity value for consecutive ones of said pairs of first and second signal vector component digital signals corresponding with said electrical signals and by comparing said mean intensity value with a predetermined presence threshold value.

63. An ultrasonic transmission method as claimed in claim 61, wherein said first and second signal vector component digital signals are respectively associated with a real component value and an imaginary component value and wherein after said step (a) there is provided steps of:

(b) providing a correction parameter defined according to the following mathematical expressions:

$$A_{k,l} = AI_{k,l} + iAQ_{k,l} = \frac{T}{M_{k,l}} \quad (4)$$

$$M_{k,l} = \frac{i}{J} \sum_{j=0}^{J-1} S_{j,k,l} \quad (5)$$

$$S_{j,k,l} = SI_{j,k,l} + iSQ_{j,k,l} \quad (6)$$

wherein k and l are primary coordinates according to first and second axis X and Y of a cartesian reference system for the ultrasonic detector array and associated image elements, with k=0,K−1 and l=0,L−1;

$A_{k,l}$ is the correction parameter associated with one of the image elements having coordinates k and l, this correction parameter compensating for detector sensibility variation among corresponding ones of the ultrasonic detectors;

$AI_{k,l}$ is the real component value of the correction parameter associated with one of the image elements having coordinates k and l;

$AQ_{k,l}$ is the imaginary component value of the correction parameter associated with one of the image elements having coordinates k and l;

T is a target parameter being characterized by a target uniform amplitude and phase values corresponding to a reference target image;

$M_{k,l}$ is a mean value of sample pairs of first and second signal vector component signals associated with one of the image elements having coordinates k and l, prior detecting the presence of an object apparently moving in the detecting zone;

J is a predetermined number of said sample pairs of first and second signal vector component signals;

$S_{j,k,l}$ is the signal vector of a sample j associated with one of said image elements having coordinates k and l;

$SI_{j,k,l}$ is a real component value associated with said first signal vector component digital signals and corresponds to the real component value of said signal vector of a sample j associated with one of said image elements having coordinates k and l;

$SQ_{j,k,l}$ is an imaginary component associated with said second signal vector component digital signals and corresponds to the imaginary component value of said signal vector of a sample j associated with one of said image elements having coordinates k and l; and (c) multiplying said component values of said first and second signal vector component digital signals with respective real component value and imaginary component value of said correction parameter to produce a corrected signal vector according to the following mathematical expressions:

$$C_{k,l} = A_{k,l} B_{k,l} = CI_{k,l} + iCQ_{CQk,l} \quad (7)$$

$$B_{k,l} = BI_{k,l} + iBQ_{k,l} \quad (8)$$

wherein $C_{k,l}$ is the corrected signal vector associated with one of said image elements having coordinates k and l;

$CI_{k,l}$ is a real component value associated with said first corrected signal vector component digital signals and corresponds to a real component value of said corrected signal vector associated with one of said image elements having coordinates k and l;

$CQ_{k,l}$ is an imaginary component value associated with said second corrected signal vector component digital signals and corresponds to an imaginary component value of said corrected signal vector associated with one of the image elements having coordinates k and l;

$B_{k,l}$ is the signal vector associated with one of said image elements having coordinates k and l;

$BI_{k,l}$ is a real component value associated with said first signal vector component digital signals and corresponds to the real component value of said signal vector associated with one of said image elements having coordinates k and l; and BQ$_{k,l}$ is an imaginary component value associated with said second signal vector component digital signals and corresponds to the imaginary component value of said signal vector associated with one of said image elements having coordinates k and l.

64. An ultrasonic transmission imaging method as claimed in claim 63, wherein after said step (b) there is provided the step of:

(d) comparing values of said correction parameter with a predetermined correction threshold value to detect corresponding unusable ones of said electrical signals; and (e) substituting for corresponding ones of said pairs of first and second signal vector component signals respective first and second signal vector component signals corresponding to proximate usable ones of said ultrasonic detectors.

65. An ultrasonic transmission imaging method as claimed in claim 63, wherein said step (vii) is carried out by applying a convolution technique to produce corresponding pairs of first and second resulting signal vector component digital signals forming said focused digital image representation of said object traversing ultrasonic waves according to the following mathematical expressions:

$$D_{k,l} = \sum_{m=-M}^{M} \sum_{n=-N}^{N} C_{k-m,l-n} L_{m,n} = DI_{k,l} + iDQ_{k,l} \quad (9)$$

$$C_{k-m,l-n} = A_{k-m,l-n} B_{k-m,l-n} \quad (10)$$

$$B_{k-m,l-n} = BI_{k-m,l-n} + iBQ_{k-m,l-n} \quad (11)$$

$$L_{m,n} = \frac{F_{m,n}}{L_{norm}} = LI_{m,n} + iLQ_{m,n} \quad (12)$$

$$F_{m,n} = FI_{m,n} + iFQ_{m,n} \quad (13)$$

$$L_{norm} = LI_{norm} + iLQ_{norm} \quad (14)$$

wherein:

m and n are secondary coordinates according to first and second axis X and Y of the cartesian reference system for said ultrasonic detector array and associated image elements, with m=–M,M and n=–N,N, the size of said focusing function data being equal to (2M+1)(2N+1);

$D_{k,l}$ is the resulting signal vector associated with one of said image elements having coordinates k and l;

$DI_{k,l}$ is a real component value of said first resulting signal vector component digital signals and corresponds to a real component value of said resulting signal vector associated with one of said image elements having coordinates k and l;

$DQ_{k,l}$ is an imaginary component value of said second resulting signal vector component digital signals and corresponds to an imaginary component value of said resulting signal vector associated with one of said image elements having coordinates k and l;

$C_{k-m,l-n}$ is the corrected signal vector associated with one of said image elements having coordinates k-m and l-n;

$A_{k-m,l-n}$ is the correction parameter associated with one of said image elements having coordinates k-m and l-n;

$B_{k-m,l-n}$ is the signal vector associated with one of said image elements having coordinates k-m and l-n;

$BI_{k-m,l-n}$ is a real component value associated with said first signal vector component digital signals and corresponds to the real component value of said signal vector associated with one of said image elements having coordinates k-m and l-n;

$BQ_{k-m,l-n}$ is an imaginary component value associated with said second signal vector component digital signals and corresponds to the imaginary component value of said signal vector associated with one of said image elements having coordinates k-m and l-n;

$L_{m,n}$ is a normalized focusing function data corresponding to one of said image elements having coordinates m and n;

$LI_{m,n}$ is a real component value of said normalized focusing function data corresponding to one of said image elements having coordinates m and n;

$LQ_{m,n}$ is an imaginary component value of said normalized focusing function data corresponding to one of said image elements having coordinates m and n;

$L_{norm}$ is a focusing function normalization parameter;

$LI_{norm}$ is a real component value of said focusing function normalization parameter;

$LQ_{norm}$ is an imaginary component value of said focusing function normalization parameter;

$F_{m,n}$ is the focusing function data corresponding to one of said image elements having coordinates m and n;

$FI_{m,n}$ is a real component value of said focusing function data corresponding to one of said image elements having coordinates m and n;

$FQ_{m,n}$ is an imaginary component value of said focusing function data corresponding to one of said image elements having coordinates m and n.

66. An ultrasonic transmission imaging method as claimed in claim 65, wherein said normalization parameter $L_{norm}$ can be derived according to the following mathematical expression:

$$L_{norm} = \sqrt{\sum_{m=-M}^{M} \sum_{n=-N}^{N} (F_{m,n} F_{m,n})} \quad (15)$$

67. An ultrasonic transmission imaging method as claimed in claim 65, wherein said focusing function data further establishes, for each image element comprised in said focusing aperture, an amplitude displacement value relative to a reference amplitude value associated with said focal line, said focusing function data $F_{m,n}$ being derived according to the following mathematical expressions:

$$FI_{m,n} = FI(x_m, y_n, \omega, \lambda, z) = \quad (17)$$

$$e^{-(x_m^2 + y_n^2)K(\omega,\lambda,z)} \cos\left[\frac{\lambda z}{\pi \omega^2}(x_m^2 + y_n^2)K(\omega,\lambda,z)\right]$$

$$FI_{m,n} = FI(x_m, y_n, \omega, \lambda, z) = \quad (18)$$

$$e^{-(x_m^2 + y_n^2)K(\omega,\lambda,z)} \sin\left[\frac{\lambda z}{\pi \omega^2}(x_m^2 + y_n^2)K(\omega,\lambda,z)\right]$$

$$K(\omega,\lambda,z) = \frac{\pi^2 \omega^2}{\lambda^2 z^2 + \pi^2 \omega^2} \quad (19)$$

$$x_m = m\, dx \quad (20)$$

$$y_m = n\, dy \quad (21)$$

wherein:

$x_m$ and $y_n$ are physical position coordinates according to first and second axis X and Y of the cartesian reference system for said ultrasonic detectors array and associated image elements, and associated with one of said image elements having coordinates m and n;

$K(w,\lambda,z)$ is a wave propagation damping factor;

dx is physical dimension along X axis of said image elements dy is physical dimension along Y axis of said image elements w is a desired image resolution;

$\lambda$ is the wavelength of the ultrasonic waves;

z is the distance between said focus point and a nearest one of said ultrasonic detectors.

68. An ultrasonic transmission imaging method as claimed in claim 63, wherein after said step (vi) there are provided the steps of:

(c) providing a normalized focusing function data according to the following mathematical expressions:

$$L_{m,n} = \frac{F_{m,n}}{L_{norm}} = LI_{m,n} + iLQ_{m,n}^- \qquad (12)$$

$$F_{m,n} = FI_{m,n} + iFQ_{m,n} \qquad (13)$$

$$L_{norm} = LI_{norm} + iLQ_{norm} \qquad (14)$$

wherein:

m and n are secondary coordinates according to first and second axis X and Y of the cartesian reference system for said ultrasonic detector array and associated image elements, with m=–M,M and n=–N,N, the size of said focusing function data being equal to (2M+1)(2N+1);

$L_{m,n}$ is a normalized focusing function data corresponding to one of said image elements having coordinates m and n;

$LI_{m,n}$ is a real component value of said normalized focusing function data corresponding to one of said image elements having coordinates m and n;

$LQ_{m,n}$ is an imaginary component value of said normalized focusing function data corresponding to one of said image elements having coordinates m and n;

$L_{norm}$ is a focusing function normalization parameter;

$LI_{norm}$ is a real component value of said focusing function normalization parameter;

$LQ_{norm}$ is an imaginary component value of said focusing function normalization parameter;

$F_{m,n}$ is the focusing function data corresponding to one of said image elements having coordinates m and n;

$FI_{m,n}$ is a real component value of said focusing function data corresponding to one of said image elements having coordinates m and n;

$FQ_{m,n}$ is an imaginary component value of said focusing function data corresponding to one of said image elements having coordinates m and n; and wherein said step (vii) is carried out by steps of:

(d) applying a first Fourier transform operation on said normalized focusing function data $L_{m,n}$ according to said coordinates k or l to produce transformed focusing function data in a spatial frequency domain;

(e) applying a second Fourier transform operation to values of said pairs of first and second corrected signal vector component digital signals according to said coordinates k or l to produce transformed signal vector component values in the spatial frequency domain;

(f) multiplying corresponding values of said transformed focusing function data by said transformed signal vector component values;

(g) applying an inverse Fourier Transform operation on the result of said multiplication step (f) to produce said corresponding pairs of first and second resulting signal vector component digital signals forming said focused digital image representation of said object traversing ultrasonic waves according to the following mathematical expression:

$$D_{k,l} = DI_{k,l} + iDQ_{k,l} \qquad (16)$$

wherein:

$D_{k,l}$ is a resulting signal vector associated with one of said image elements having coordinates k and l;

$DI_{k,l}$ is a real component value of said first resulting signal vector component digital signals and corresponds to a real component value of said resulting signal vector associated with one of said image elements having coordinates k and l;

$DQ_{k,l}$ is an imaginary value of said second resulting signal vector component digital signals and corresponds to an imaginary component value of said resulting signal vector associated with one of said image elements having coordinates k and l.

69. An ultrasonic transmission imaging method as claimed in claim 68, wherein said normalization parameter $L_{norm}$ can be derived according to the following mathematical expression:

$$L_{norm} = \sqrt{\sum_{m=-M}^{M} \sum_{n=-N}^{N} (F_{m,n} F_{m,n})} \qquad (15)$$

70. An ultrasonic transmission imaging method as claimed in claim 68, wherein said focusing function data further establishes, for each image element comprised in said focusing aperture, an amplitude displacement value relative to a reference amplitude value associated with said focal line, said focusing function data $F_{m,n}$ being derived according to the following mathematical expressions:

$$FI_{m,n} = FI(x_m, y_n, \omega, \lambda, z) = \qquad (17)$$
$$e^{-(x_m^2 + y_n^2)K(\omega,\lambda,z)} \cos\left[\frac{\lambda z}{\pi \omega^2} (x_m^2 + y_n^2)K(\omega,\lambda,z)\right]$$

$$FI_{m,n} = FI(x_m, y_n, \omega, \lambda, z) = \qquad (18)$$
$$e^{-(x_m^2 + y_n^2)K(\omega,\lambda,z)} \sin\left[\frac{\lambda z}{\pi \omega^2} (x_m^2 + y_n^2)K(\omega,\lambda,z)\right]$$

$$K(\omega,\lambda,z) = \frac{\pi^2 \omega^2}{\lambda^2 z^2 + \pi^2 \omega^2} \qquad (19)$$

$$x_m = m \, dx \qquad (20)$$

$$y_m = n \, dy \qquad (21)$$

wherein:

$x_m$ and $y_n$ are physical position coordinates according to first and second axis X and Y of the cartesian reference system for said ultrasonic detectors array and associated image elements, and associated with one of said image elements having coordinates m and n;

$K(w,\lambda,z)$ is a wave propagation damping factor;

dx is physical dimension along X axis of said image elements dy is physical dimension along Y axis of said image elements
w is a desired image resolution;
λ is the wavelength of the ultrasonic waves;

z is the distance between said focus point and a nearest one of said ultrasonic detectors.

* * * * *